US 8,268,784 B2

(12) United States Patent
Conde-Knape et al.

(10) Patent No.: US 8,268,784 B2
(45) Date of Patent: Sep. 18, 2012

(54) NEUROPEPTIDE-2 RECEPTOR (Y-2R) AGONISTS AND USES THEREOF

(75) Inventors: Karin Conde-Knape, Englewood, NJ (US); Waleed Danho, Wayne, NJ (US); George Ehrlich, New York, NY (US); Nader Fotouhi, Basking Ridge, NJ (US); David Charles Fry, Langhorne, PA (US); Wajiha Khan, East Hanover, NJ (US); Anish Konkar, Guttenberg, NJ (US); Cristina Martha Rondinone, West Milford, NJ (US); Joseph Swistok, Nutley, NJ (US); Rebecca Anne Taub, Villanova, PA (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 384 days.

(21) Appl. No.: 12/536,688

(22) Filed: Aug. 6, 2009

(65) Prior Publication Data

US 2010/0137223 A1 Jun. 3, 2010

Related U.S. Application Data

(63) Continuation of application No. 11/607,230, filed on Dec. 1, 2006, now Pat. No. 7,642,244.

(60) Provisional application No. 60/748,071, filed on Dec. 7, 2005, provisional application No. 60/855,249, filed on Oct. 30, 2006.

(51) Int. Cl.
*A61K 38/10* (2006.01)
*C07K 7/08* (2006.01)

(52) U.S. Cl. ........ 514/18.1; 514/5.2; 514/6.9; 514/21.5; 530/326; 930/20; 930/30

(58) Field of Classification Search .................. None
See application file for complete search history.

(56) References Cited

U.S. PATENT DOCUMENTS

| 5,283,317 | A | 2/1994 | Saifer et al. |
| 5,468,478 | A | 11/1995 | Saifer et al. |
| 6,235,718 | B1 | 5/2001 | Balasubramanium et al. |
| 7,410,949 | B2 | 8/2008 | Danho et al. |
| 7,642,244 | B2 * | 1/2010 | Conde-Knape et al. ....... 514/1.1 |
| 2006/0160742 | A1 | 7/2006 | Danho et al. |

FOREIGN PATENT DOCUMENTS

| EP | 0907658 | 4/1999 |
| WO | 97/46579 | 12/1997 |
| WO | WO 2004/066966 A2 | 8/2004 |
| WO | WO 2004/089280 | 10/2004 |
| WO | 2005/053726 | 6/2005 |
| WO | WO 2005/080424 | 9/2005 |
| WO | WO 2006/091505 | 8/2006 |
| WO | 2007/085887 | 8/2007 |

OTHER PUBLICATIONS

Translation of Japanese Office Action No. 2008-543768 dated May 31, 2011.
Translation of Russian Office Action dated Jul. 26, 2010 in Corresponding Appl. 2008127265.
Translation of Israeli Office Action dated in Corresponding Appl. 191636 dated Jul. 20, 2010.
(Australian Office Action in Corres. Appl. AU 2006324076 Sep. 7, 2011).
Chilean Office Action Nov. 11, 2010.
Potter, EK, et. al., Eur J Pharmac 267 (1994) 253-262.
Batterham, S, et. al., Nature V.418 (2002) 650-654.
Krstenansky, et. al., Peptides, Proceedings of the 12$^{th}$ American Peptide Symposium, J. Smith and J. Rivier Editors, ESCOM, Leiden p. 136-137, (1992).
Somack, R (1991) Free Rad Res Commun 12-13, 553-562.
Saifer, MGP, et. al., Polym Preprints (1997) 576-577.
Sherman, MR, et. al,(1997) in JM Harris et al (Eds) Poly(ethylene glycol) Chemistry and Biological Applications. ACS Symposium Series 680 p. 155-169 Washington DC. Am Chem Soc.
Kaga T et al., Peptides 22: 501-506 (2001).
King PJ et al., Eur J Pharmacol 396: R1-3 (2000).
Batterham RL et al., Nature 418: 650-654 (2002).
Batterham RL et al., New Engl J Med 349: 941-948 (2003).
Korner et al., J Clin Endocrinol Metabol 90: 359-365 (2005).
Chan JL et al., Obesity 14: 194-198 (2006).
Stratis C et al., Obes Surg 16: 752-758 (2006).
Borg CM et al., Br J Surg 93: 210-215 (2006).
Pittner RA et al., Int J Obes 28: 963-971 (2004).
H. Ansel et. al., Pharmaceutical Dosage Forms and Drug Delivery Systems (6th Ed. 1995) at pp. 196 and 1456-1457.
H. Ansel et. al., Pharmaceutical Dosage Forms and Drug Delivery Systems (6th Ed. 1995) at pp. 108-109.
Krogsgaard-Larsen, et. al., Textbook of Drug Design and Development (2d Ed. 1996) at pp. 152-191.
Merrifield, R. B., J. Amer. Chem. Soc. 85, 2149-2154 (1963).
J. Hutchinson et. al, J .Med. Chem. 1996, 39, 4583-4591.
Kaiser et at. Anal.Biochem.34, 595-598 (1970).
Shechter, Y., et al., FEBS Letters, vol. 579, No. 11, pp. 2439-2444 (2005), XP005390209.
Boggiano, M.M., et al., Obesity Reviews, Blackwell Science, GB, vol. 6, No. 4, pp. 307-322 (2005), XP002376517.
Krstenansky, J.L., et al., Proceedings of the National Academy of Sciences of USA, vol. 86, No. 12, pp. 4377-4381 (1989), XP002376516.
Beck-Sickinger, A.G., et al., Eur. J. Biochem., vol. 194, No. 2, pp. 449-456 (1990), XP002376459.
Kirby, D.A., et al., Journal of Medicinal Chemistry, vol. 36, No. 3, pp. 385-393 (1993), XP002333099.
Kirby, D.A., et al., Journal of Medicinal Chemistry, vol. 38, No. 22, pp. 4579-4586 (1995), XP002306036.

* cited by examiner

*Primary Examiner* — Jeffrey E Russel
(74) *Attorney, Agent, or Firm* — George W. Johnston; Dennis P. Tramaloni; Patricia S. Rocha-Tramaloni

(57) ABSTRACT

Provided herein are neuropeptide-2 receptor agonists of the formula (I):

$$Y-R_1-R_2-X-R_3-R_4-R_5-R_6-R_7-R_8-R_9-R_{10}-R_{11}-R_{12}-R_{13}-R_{14}-NH_2,$$

with $Y'$ attached to $R_2$, as well as pharmaceutically acceptable salts, derivatives and fragments thereof, wherein the substituents are as those disclosed in the specification. X is 4-oxo-6-(1-piperazinyl)-3(4H)-quinazoline-acetic acid (Pqa). These compounds, and the pharmaceutical compositions containing them, are useful for the treatment of diseases such as, for example, obesity and diabetes.

3 Claims, 25 Drawing Sheets

US 8,268,784 B2

NEUROPEPTIDE-2 RECEPTOR (Y-2R) AGONISTS AND USES THEREOF

PRIORITY TO RELATED APPLICATION

This application is a continuation of U.S. application Ser. No. 11/607,230, filed Dec. 1, 2006, now pending, which claims the benefit of U.S. Provisional Application No. 60/748,071, filed Dec. 7, 2005, and U.S. Provisional Application No. 60/855,249, filed Oct. 30, 2006. The entire contents of the above-identified applications are hereby expressly incorporated by reference.

FIELD OF THE INVENTION

The invention relates to truncated analogs of $PYY_{3-36}$. The analogs are agonists of neuropeptide-2 receptor and are useful for the treatment of metabolic diseases and disorders, such as, for example, obesity, type 2 diabetes, metabolic syndrome, insulin resistance and dyslipidemia.

All documents cited herein are hereby expressly incorporated herein by reference.

BACKGROUND OF THE INVENTION

Metabolic diseases and disorders are widely recognized as serious health problems for developed countries, having reached epidemic levels in the United States. According to recent studies on obesity, for example, more than 50% of the U.S. population is considered overweight, with more than 25% diagnosed as clinically obese and at considerable risk for heart disease, type 2 diabetes, and certain cancers. This epidemic presents a significant burden on the health care system as projected obesity treatment costs of more than $70 billion annually are expected in the U.S. alone. Strategies for treating obesity include reduction of food intake and enhancing the expenditure of energy.

Neuropeptide Y (NPY), a 36 amino acid peptide neurotransmitter, is a member of the pancreatic polypeptide class of neurotransmitters/neurohormones which has been shown to be present in both the periphery and central nervous system. NPY is one of the most potent orexigenic agents known and has been shown to play a major role in the regulation of food intake in animals, including humans.

Six neuropeptide Y receptors (NPY), the Y1-, Y2-, Y3-, Y4, and Y5- and Y6-subtypes, have been cloned, which belong to the rhodopsin-like G-protein-coupled 7-transmembrane spanning receptors (GPCR). The NPY Y2 receptor (Y2R) is a 381 amino-acid receptor which inhibits the activation of adenyl cyclase via $G_i$ while displaying low homology with other known NPY receptors. There is a high degree of conservation between rat and human Y2 receptors with 98% amino acid identity.

The Y2R receptor is widely distributed within the central nervous system in both rodents and humans. In the hypothalamus, Y2 mRNA is localized in the arcuate nucleus, preoptic nucleus, and dorsomedial nucleus. In the human brain, Y2R is the predominant Y receptor subtype. Within the arcuate nucleus, over 80% of the NPY neurons co-express Y2R mRNA. Application of a Y2-selective agonist has been shown to reduce the release of NPY from hypothalamic slices in vitro, whereas the Y2 non-peptide antagonist BIIE0246 increases NPY release. These findings support the role of Y2R as a presynaptic autoreceptor that regulates the NPY release and hence may be involved in the regulation of feeding. (Kaga T et al., Peptides 22: 501-506 (2001) and King P J et al., Eur J Pharmacol 396: R1-3 (2000)).

Peptide $YY_{3-36}$ ($PYY_{3-36}$) is a 34 amino acid linear peptide having neuropeptide Y2 (NPY2R) agonist activity. It has been demonstrated that Intra-arcuate (IC) or Intra-peritoneal (IP) injection of $PYY_{3-36}$ reduced feeding in rats and, as a chronic treatment, reduced body weight gain. Intra-venous (IV) infusion (0.8 pmol/kg/min) for 90 min of $PYY_{3-36}$ reduced food intake in obese and normal human subjects over 24 hours. These finding suggest that the PYY system may be a therapeutic target for the treatment of obesity. (Batterham R L et al., Nature 418: 650-654 (2002); Batterham R L et al., New Engl J Med 349: 941-948 (2003)). Further, a $Cys^2$-$(D)Cys^{27}$-cyclized version of PYY, in which residues 5-24 were replaced by a methylene-chain of 5 to 8 carbons in length, showed activation of the intestinal PYY receptor, as evidenced by reduced current across voltage-clamped mucosal preparations of rat jejunum. (Krstenansky, et al. in Peptides, Proceedings of the Twelfth American Peptide Symposium. J. Smith and J. Rivier Editors, ESCOM. Leiden Page 136-137).

Further, covalent modification of proteins with poly (ethylene glycol) or poly (ethylene oxide) (both referred to as PEG), was demonstrated with superoxide dismutase (Somack, R, et al., (1991) Free Rad Res Commun 12-13:553-562; U.S. Pat. Nos. 5,283,317 and 5,468,478) and for other types of proteins, e.g., cytokines (Saifer, M G P, et al., (1997) Polym Preprints 38:576-577; Sherman, M R, et al., (1997) in J M Harris, et al., (Eds.), Poly(ethylene glycol) Chemistry and Biological Applications. ACS Symposium Series 680 (pp. 155-169) Washington, D.C.: American Chemical Society).

In addition, recent data have shown that gastric bypass patients have an early and exaggerated increase in PYY levels that may be partly responsible for the early glycemic control and long term weight maintenance demonstrating the importance of this peptide in the pathogenesis of metabolic diseases. Other known actions of PYY include: reduced gastric emptying and delayed gastrointestinal transit that is responsible for improved postprandial glycemic control. Indices of hyperglycaemia such as $HbA_{1c}$ and fructosamine show a dose-dependent reduction after peripheral administration of $PYY_{3-36}$ in animal models of type 2 diabetes. Thus, these results indicate that $PYY_{3-36}$, or pharmaceutically related agonists, may offer a long term therapeutic approach to glycemic and weight control. (Korner et al., J Clin Endocrinol Metabol 90: 359-365 (2005); Chan J L et al., Obesity 14: 194-198 (2006); Stratis C et al., Obes Surg 16: 752-758 (2006); Borg C M et al., Br J Surg 93: 210-215 (2006); and Pittner R A et al., Int J Obes 28: 963-971 (2004)).

A need exists, however, for novel engineered analogs of PYY having lower molecular weight, while possessing equal or better potency and selectivity against Y1, Y4 and Y5 receptors, pharmacokinetic properties and pharmacological properties. Preferably, a need exists for compounds having greater duration of activity than those previously available. A need also exists for pegylated analogs of PYY in order to, for example, increase protein half-life and reduce immunogenicity in subjects in need of such agonists.

SUMMARY OF THE INVENTION

In an embodiment of the present invention, provided is a neuropeptide-2 receptor agonist of the formula (I):

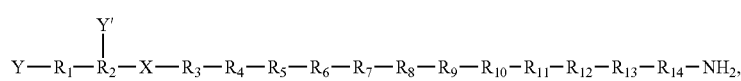

(I)

wherein:

X is 4-oxo-6-(1-piperazinyl)-3(4H)-quinazoline-acetic acid (Pqa),

Y is H, an acyl moiety, a substituted or unsubstituted alkyl, a substituted or unsubstituted lower alkyl, a substituted or unsubstituted aryl, a substituted or unsubstituted heteroaryl, a substituted or unsubstituted alkoxy, a poly(ethylene) glycol moiety, $PEG_m$-SSA, $PEG_m$-β-SBA, $PEG_m$-SPA or $PEG_m$-BTC, Y' is H, a poly(ethylene) glycol moiety, $PEG_m$-SSA, $PEG_m$-β-SBA, $PEG_m$-SPA or $PEG_m$-BTC, $R_1$ is Ile, Ala, (D) Ile, N-methyl Ile, Aib, 1-1Aic, 2-2 Aic, Ach or Acp, $R_2$ is Lys, Ala, (D) Lys, NMelys, Nle or (Lys-Gly), $R_3$ is Arg, Ala, (D)Arg, N-methyl Arg, Phe, 3,4,5-Trifluoro Phe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D) Tyr, N-methyl Tyr, Trp, Tic, Bip, Dip, (1)Nal, (2)Nal, 3,4,5-Trifluoro Phe or 2,3,4,5,6-Pentafluoro Phe, $R_6$ is Leu, Ala, (D)Leu or N-methyl Leu, $R_7$ is Asn, Ala or (D)Asn, $R_8$ is Leu or Trp, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, $R_{14}$ is Tyr, (D) Tyr or N-methyl Tyr, modified-Tyr, Phe, modified-Phe or Trp, and m is 1 to 60 KDa, or a pharmaceutically acceptable salt thereof.

In another embodiment of the present invention, provided is a pharmaceutical composition, comprising a therapeutically effective amount of a neuropeptide-2 agonist of the formula (I):

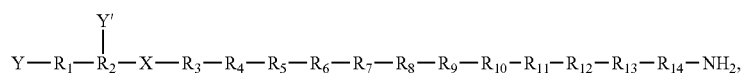

(I)

wherein:

X is 4-oxo-6-(1-piperazinyl)-3(4H)-quinazoline-acetic acid (Pqa),

Y is H, an acyl moiety, a substituted or unsubstituted alkyl, a substituted or unsubstituted lower alkyl, a substituted or unsubstituted aryl, a substituted or unsubstituted heteroaryl, a substituted or unsubstituted alkoxy, a poly(ethylene) glycol moiety, $PEG_m$-SSA, $PEG_m$-β-SBA, $PEG_m$-SPA or $PEG_m$-BTC, Y' is H, a poly(ethylene) glycol moiety, $PEG_m$-SSA, $PEG_m$-β-SBA, $PEG_m$-SPA or $PEG_m$-BTC, $R_1$ is Ile, Ala, (D) Ile, N-methyl Ile, Aib, 1-1Aic, 2-2 Aic, Ach or Acp, $R_2$ is Lys, Ala, (D) Lys, NMelys, Nle or (Lys-Gly), $R_3$ is Arg, Ala, (D)Arg, N-methyl Arg, Phe, 3,4,5-Trifluoro Phe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D) Tyr, N-methyl Tyr, Trp, Tic, Bip, Dip, (1)Nal, (2)Nal, 3,4,5-TrifluoroPhe or 2,3,4,5,6-Pentafluoro Phe, $R_6$ is Leu, Ala, (D)Leu or N-methyl Leu, $R_7$ is Asn, Ala or (D)Asn, $R_8$ is Leu or Trp, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, $R_{14}$ is Tyr, (D) Tyr or N-methyl Tyr, modified-Tyr, Phe, modified-Phe or Trp, and m is 1 to 60 KDa, or a pharmaceutically acceptable salt thereof, and a pharmaceutically acceptable carrier.

In a further embodiment of the present invention, provided is a method of treating a metabolic disease or disorder, comprising administering to a patient in need of said treatment a therapeutically effective amount of a neuropeptide-2 receptor agonist of the formula (I):

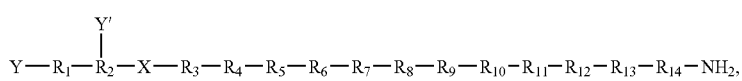

(I)

wherein:

X is 4-oxo-6-(1-piperazinyl)-3(4H)-quinazoline-acetic acid (Pqa),

Y is H, an acyl moiety, a substituted or unsubstituted alkyl, a substituted or unsubstituted lower alkyl, a substituted or unsubstituted aryl, a substituted or unsubstituted heteroaryl, a substituted or unsubstituted alkoxy, a poly(ethylene) glycol moiety, $PEG_m$-SSA, $PEG_m$-β-SBA, $PEG_m$-SPA or $PEG_m$-BTC, Y' is H, a poly(ethylene) glycol moiety, $PEG_m$-SSA, $PEG_m$-β-SBA, $PEG_m$-SPA or $PEG_m$-BTC, $R_1$ is Ile, Ala, (D) Ile, N-methyl Ile, Aib, 1-1Aic, 2-2 Aic, Ach or Acp, $R_2$ is Lys, Ala, (D) Lys, NMelys, Nle or (Lys-Gly), $R_3$ is Arg, Ala, (D)Arg, N-methyl Arg, Phe, 3,4,5-Trifluoro Phe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D) Tyr, N-methyl Tyr, Trp, Tic, Bip, Dip, (1)Nal, (2)Nal, 3,4,5-TrifluoroPhe or 2,3,4,5,6-Pentafluoro Phe, $R_6$ is Leu, Ala, (D)Leu or N-methyl Leu, $R_7$ is Asn, Ala or (D)Asn, $R_8$ is Leu or Trp, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, $R_{14}$ is Tyr, (D) Tyr or N-methyl Tyr, modified-Tyr, Phe, modified-Phe or Trp, and m is 1 to 60 KDa, or a pharmaceutically acceptable salt thereof.

DETAILED DESCRIPTION OF THE INVENTION

Figure 1:
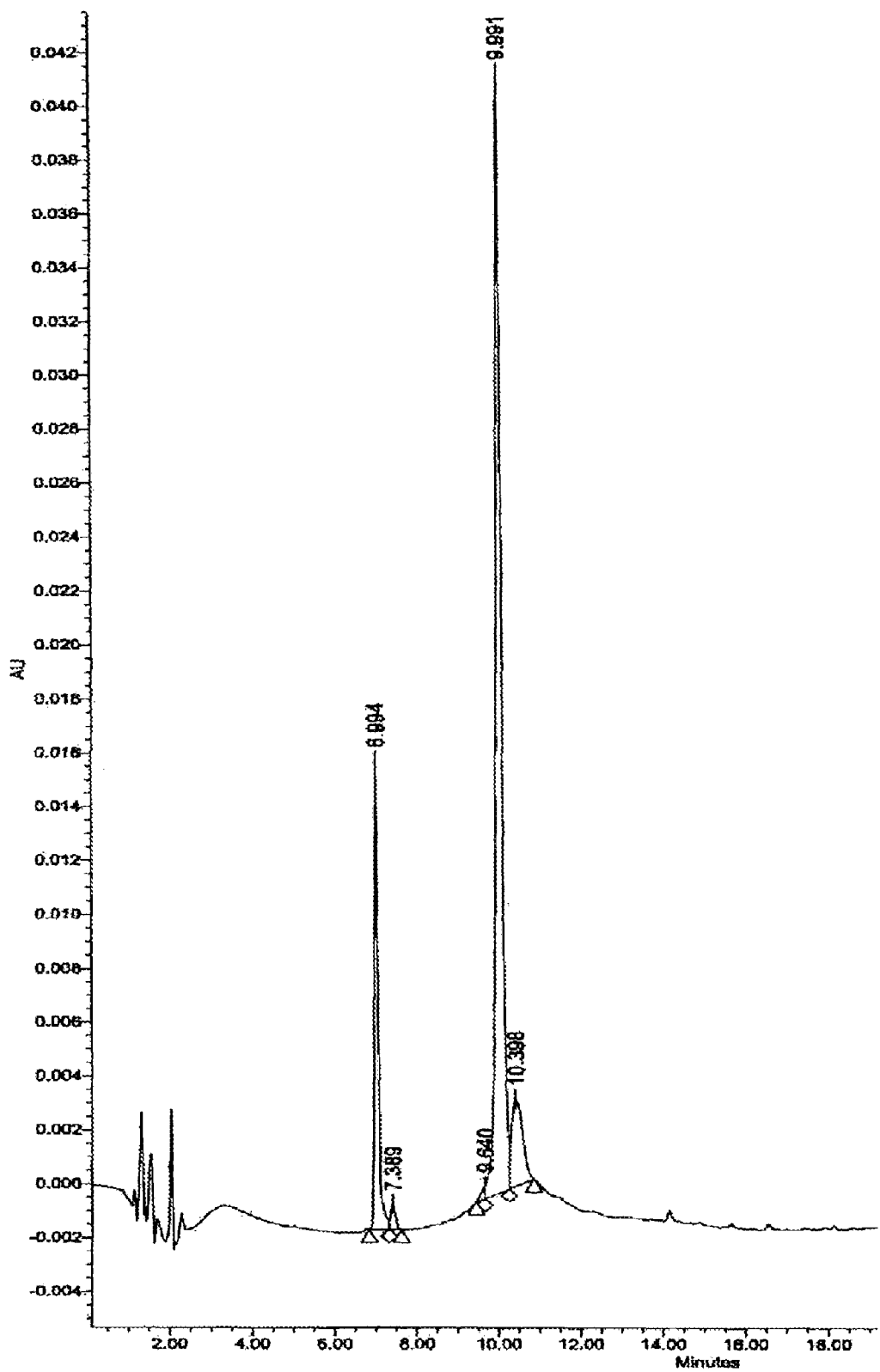
FIG. 1 shows an HPLC chromatogram of a reaction mixture containing a compound (example 34) of the present invention.

The compounds of the invention are advantageous because, for example, they are truncated versions of the $PYY_{3-36}$. The shorter peptides, for example, not only facilitate easier synthesis and purification of the compounds, but also improve and reduce manufacturing procedures and expenses. Moreover, the compounds of the invention will interact preferably with Y2-receptors and not with homologous receptors such as NPY Y1, Y4 and Y5. Unwanted agonist or antagonist side reactions are, thereby, minimized.

The compounds of the invention are preferably useful for treating metabolic diseases and disorders. Such metabolic diseases and disorders include, for example, obesity, diabetes, preferably type 2 diabetes, metabolic syndrome (also known as Syndrome X), insulin resistance, dyslipidemia, impaired fasting glucose and impaired glucose tolerance.

It is to be understood that the invention is not limited to the particular embodiments of the invention described herein, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Although any methods, devices and materials similar or equivalent to those described herein can be used in the practice or testing of the invention, the preferred methods, devices and materials are now described.

All peptide sequences mentioned herein are written according to the usual convention whereby the N-terminal amino acid is on the left and the C-terminal amino acid is on the right, unless noted otherwise. A short line between two amino acid residues indicates a peptide bond. Where the amino acid has isomeric forms, it is the L form of the amino acid that is represented unless otherwise expressly indicated. For convenience in describing this invention, the conventional and nonconventional abbreviations for the various amino acids are used. These abbreviations are familiar to those skilled in the art, but for clarity are listed below:

Asp=D=Aspartic Acid; Ala=A=Alanine; Arg=R=Arginine; Asn=N=Asparagine; Gly=G=Glycine; Glu=E=Glutamic Acid; Gln=Q=Glutamine; His=H=Histidine; Ile=I=Isoleucine; Leu=L=Leucine; Lys=K=Lysine; Met=M=Methionine; Phe=F=Phenylalanine; Pro=P=Proline; Ser=S=Serine; Thr=T=Threonine; Trp=W=Tryptophan; Tyr=Y=Tyrosine; Cys=C=Cysteine; and Val=V=Valine.

Also for convenience, the following abbreviations or symbols are used to represent the moieties, reagents and the like used in this invention:

Aib alpha-aminoisobutyric acid;
1-1-Aic 1-aminoindane-1-carboxylic acid;
2-2-Aic 2-aminoindane-2-carboxylic acid;
Ach alpha-aminocyclohexane-carboxylic acid;
Acp alpha-aminocyclopentane-carboxylic acid;
Tic alpha-amino-1,2,3,4, tetrahydroisoquinoline-3-carboxylic acid;
3-Pal alpha-amino-3-pyridylalanine-carboxylic acid;
4-Pal alpha-amino-4-pyridylalanine-carboxylic acid;
4-MeO-Apc 1-amino-4-(4-methoxyphenyl)-cyclohexane-1-carboxylic acid;
Bip 4-phenyl-phenylalanine-caroxylic acid;
Dip 3,3-diphenylalanine-carboxylic acid;
Pqa 4-oxo-6-(1-piperazinyl)-3(4H)-quinazoline-acetic acid (CAS 889958-08-1);
3,4,5, F3-Phe 3,4,5 Trifluoro phenylalanine;
2,3,4,5,6, F5-Phe 2,3,4,5,6-Pentafluoro phenylalanine;
Cha Cyclohexyl Alanine;
(1) Nal 1-Naphthyl Alanine;
(2) Nal 2-Naphthyl Alanine;
Fmoc 9-Fluorenylmethyloxycarbonyl;
Mtt 4-Methyltrityl;
2Pip 2-Phenylisopropyl ester;
Pmc 2,2,5,7,8-Pentamethylchroman-6-sulfonyl;
$CH_2Cl_2$ Methylene chloride;
A2O Acetic anhydride;
$CH_3CN$ Acetonitrile;
DMAc Dimethylacetamide;
DMF Dimethylformamide;
DIPEA N,N-Diisopropylethylamine;
TFA Trifluoroacetic acid;
HOBT N-Hydroxybenzotriazole;
DIC N,N'-Diisopropylcarbodiimide;
BOP Benzotriazol-1-yloxy-tris-(dimethylamino)phosphonium-Hexafluorophosphate;
HBTU 2-(1H-Benzotriazole-1-yl)-1,1,3,3-tetramethyluronium-Hexafluorophosphate;
NMP 1-methyl 2-Pyrolidenone;
SSA succinimidyl succinamide;
β-SBA succinimidyl beta-butanoic acid;
SPA succinimidyl proprionic acid;
BTC benzotriazole carbonate;
MALDI-TOF Matrix assisted laser desorption ionization-time of flight;
FAB-MS Fast atom bombardment mass spectrometry;
ES-MS Electro spray mass spectrometry;
$PEG_m$-SSA $PEG_m$-$CH_2CH_2NHCOCH_2CH_2CO$—;
$PEG_m$-β-SBA $PEG_m$-$CH(CH_3)CH_2CO$—;
$PEG_m$-SPA $PEG_m$-$CH_2CH_2CO$—;
$PEG_m$-BTC $PEG_m$-CO—; and
m is greater than 1 KDa.

In a preferred embodiment, m is 1 to 60 KDa. More preferably, m is 20 to 40 KDa. Most preferably, m is 30 KDa.

As used herein, the term "alkyl" means a branched or unbranched, cyclic or acyclic, saturated or unsaturated hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means a branched or unbranched, cyclic or acyclic, saturated or unsaturated hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl and cycloloweralkenyl.

As used herein, the term "acyl" means an optionally substituted alkyl, cycloalkyl, heterocyclic, aryl or heteroaryl group bound via a carbonyl group and includes groups such as acetyl, propionyl, benzoyl, 3-pyridinylcarbonyl, 2-morpholinocarbonyl, 4-hydroxybutanoyl, 4-fluorobenzoyl, 2-naphthoyl, 2-phenylacetyl, 2-methoxyacetyl and the like.

As used herein, the term "aryl" means a substituted or unsubstituted carbocyclic aromatic group, such as phenyl or naphthyl.

The term "heteroaryl", alone or in combination with other groups, means a monocyclic or bicyclic radical of 5 to 12 ring atoms having at least one aromatic ring containing one, two, or three ring heteroatoms selected from N, O, and S, the remaining ring atoms being C, with the understanding that the attachment point of the heteroaryl radical will be on an aromatic ring. One or two ring carbon atoms of the heteroaryl group may be replaced with a carbonyl group.

The alkyl, aryl and heteroaryl groups may be substituted or unsubstituted. Where substituted, there will generally be 1 to 3 substituents present, preferably 1 substituent. Substituents may include: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), alkoxy, aryloxy, alkoxyalkyl, aryloxyalkyl, acyl, acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, peperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be 1 to 3 substitutents present, preferably 1 substituent. Substituents include the substituent groups listed above other than alkyl, aryl and arylalkyl.

As used herein, the term "alkoxy" means alkyl-O— and "alkanoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical, and more preferably a fluorine or chlorine radical.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as acetic acid, p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters may retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the cleaved hydrogen is replaced with -lower alkyl which is optionally substituted, e.g., with heterocycle, cycloalkyl, etc. Examples of substituted lower alkyl esters are those in which -lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —CONH$_2$ is also considered an ester, as the —NH$_2$ is cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191

The present representative compounds may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods. Such methods are disclosed in, for example, Merrifield, R. B., J. Amer. Chem. Soc. 85, 2149-2154 (1963); Barany et al., The Peptides, Analysis, Synthesis and Biology, Vol. 2, Gross, E. and Meienhofer, J., Eds. Academic Press 1-284 (1980), which are incorporated herein by reference.

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group on an amino acid or fragment while that entity reacts at the carboxyl group, followed by the selective removal of the alpha amino protecting group at allow a subsequent reaction to take place at that site. While specific protecting groups have been disclosed in regard to the solid phase synthesis method, it should be noted that each amino acid can be protected by a protective group conventionally used for the respective amino acid in solution phase synthesis.

Alpha amino groups may be protected by a suitable protecting group selected from aromatic urethane-type protecting groups, such as allyloxycarbonyl, benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropyloxycarbonyl, 9-fluorenylmethyloxycarbonyl (Fmoc) and p-methoxybenzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Herein, Fmoc is most preferred for alpha amino protection.

Guanidino groups may be protected by a suitable protecting group selected from nitro, p-toluenesulfonyl (Tos), (Z,) pentamethylchromanesulfonyl (Pmc), 4-Methoxy-2,3,6,-trimethylbenzenesulfonyl (Mtr), (Pmc), and (Mtr) are most preferred for arginine (Arg).

The ε-amino groups may be protected by a suitable protecting group selected from chloro benzyloxycarbonyl (2-Cl—Z), 2-Bromo benzyloxycarbonyl (2-Br—Z)- and t-butyloxycarbonyl (Boc). Boc is the most preferred for (Lys).

Hydroxyl groups (OH) may be protected by a suitable protecting group selected from benzyl (Bzl), 2, 6 dichlorobenzyl (2, 6 diCl-Bzl), and tert. Butyl (t-Bu), (tBu) is most preferred for (Tyr), (Ser) and (Thr).

The β- and γ-amide groups may be protected by a suitable protecting group selected from 4-methyltrityl (Mtt), 2,4,6-trimethoxybenzyl (Tmob), 4,4-DimethoxyditylBis-(4-methoxyphenyl)-methyl (Dod) and Trityl (Trt). Trt is the most preferred for (Asn) and (Gln).

The indole group may be protected by a suitable protecting group selected from formyl (For), Mesityl-2-sulfonyl (Mts) and t-butyloxycarbonyl (Boc). Boc is the most preferred for (Trp).

The imidazol group may be protected by a suitable protecting group selected from Benzyl (Bzl), -t-butyloxycarbonyl (Boc), and Trityl (Trt). Trt is the most preferred for (His).

The synthesis of the amino acid Pqa is described by J. Hutchinson et. al (J. Med. Chem. 1996, 39, 4583-4591). The Fmoc-Pqa derivative was purchased from NeoMPS, Inc. (San Diego Calif.)

All solvents, isopropanol (iPrOH), methylene chloride ($CH_2Cl_2$), dimethylformamide (DMF) and N-methylpyrrolinone (NMP) were purchased from Fisher or Burdick & Jackson and were used without additional distillation. Trifluoroacetic acid was purchased from Halocarbon or Fluka and used without further purification.

Diisopropylcarbodiimide (DIC) and diisopropylethylamine (DIPEA) was purchased from Fluka or Aldrich and used without further purification. Hydroxybenzotriazole (HOBT) dimethylsulfide (DMS) and 1,2-ethanedithiol (EDT) were purchased from Sigma Chemical Co. and used without further purification. Protected amino acids were generally of the L configuration and were obtained commercially from Bachem, or Neosystem. Purity of these reagents was confirmed by thin layer chromatography, NMR and melting point prior to use. Benzhydrylamine resin (BHA) was a copolymer of styrene—1% divinylbenzene (100-200 or 200-400 mesh) obtained from Bachem or Advanced Chemtech. Total nitrogen content of these resins were generally between 0.3-1.2 meq/g.

In a preferred embodiment, peptides were prepared using solid phase synthesis by the method generally described by Merrifield, (J. Amer. Chem. Soc., 85, 2149 (1963)), although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-((R,S)-α-(1-(9H-fluoren-9-yl)-methoxyformamido)-2,4-dimethyloxybenzyl)-phenoxyacetic acid (Rink linker) to a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

Typically, the amino acids or mimetic are coupled onto the Fmoc-Linker-BHA resin using the Fmoc protected form of amino acid or mimetic, with 2-5 equivalents of amino acid and a suitable coupling reagent. After couplings, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions. Piperidine, piperazine or morpholine (20-40% v/v) in DMF may be used for this purpose. Preferably 40% piperidine in DMF is utilized.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino) phosphonium hexafluorophosphate (BOP), Bromo-tris-pyrrolidino-phosphonium hexafluorophosphate (PyBroP) 2-(1H-Benzotriazole-1-yl)-1,1,3,3-tetramethyluronium hexafluorophosphate (HBTU), and diisopropylcarbodiimide (DIC). Preferred here are HBTU and DIC. Other activating agents are described by Barany and Merrifield (in The Peptides, Vol. 2, J. Meienhofer, ed., Academic Press, 1979, pp 1-284) and may be utilized. Various reagents such as 1 hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle is as follows:

Protocol 1

| Step | Reagent | Time |
|---|---|---|
| 1 | DMF | 2 × 30 sec. |
| 2 | 20% piperidine/DMF | 1 min. |
| 3 | 20% piperidine/DMF | 15 min. |
| 4 | DMF | 2 × 30 sec. |
| 5 | iPrOH | 2 × 30 sec. |
| 6 | DMF | 3 × 30 sec. |
| 7 | Coupling | 60 min-18 hours. |
| 8 | DMF | 2 × 30 sec. |
| 9 | iPrOH | 1 × 30 sec. |
| 10 | DMF | 1 × 30 sec. |
| 11 | $CH_2Cl_2$ | 2 × 30 sec. |

Solvents for all washings and couplings were measured to volumes of 10-20 ml/g resins. Coupling reactions throughout the synthesis were monitored by the Kaiser Ninhydrin test to determine extent of completion (Kaiser et at. Anal. Biochem. 34, 595-598 (1970)). Slow reaction kinetics was observed for Fmoc-Arg (Pmc) and for couplings to secondary amines by sterically hindered acids. Any incomplete coupling reactions were either recoupled with freshly prepared activated amino acid or capped by treating the peptide resin with acetic anhydride as described above. The fully assembled peptide-resins were dried in vacuum for several hours.

For most compounds, the blocking groups were removed and the peptide cleaved from the resin. For example, the peptide-resins were treated with 100 μL ethanedithiol, 100 μl dimethylsulfide, 300 μL anisole, and 9.5 mL trifluoroacetic acid, per gram of resin, at room temperature for 180 min. Or alternately the peptide-resins were treated with 1.0 mL triisopropyl silane and 9.5 mL trifluoroacetic acid, per gram of resin, at room temperature for 180 min. The resin was filtered off and the filtrates were precipitated in chilled ethyl ether. The precipitates were centrifuged and the ether layer was decanted. The residue was washed with two or three volumes of $Et_2O$ and recentrifuged. The crude products were dried under vacuum.

Purification of the crude peptides was performed on Shimadzu LC-8A system by high performance liquid chromatography (HPLC) on a reverse phase Vydac C-18 Column (50×250 mm. 300 A, 10-15 μm). The peptides were injected to the columns in a minimum volume of either 0.1 AcOH/H$_2$O or CH$_3$CH/H$_2$O. Gradient elution was generally started at 2% B buffer, 2%-70% B over 70 minutes, (buffer A: 0.1% TFA/H$_2$O, buffer B: 0.1% TFA/CH$_3$CN) at a flow rate of 50 ml/min. UV detection was made at 220/280 nm. The fractions containing the products were separated and their purity was judged on Shimadzu LC-10AT analytical system using reverse phase Ace C18 column (4.6×50 mm) at a flow rate of 2 ml/min., gradient (2-70%) over 10 min. (buffer A: 0.1% TFA/H$_2$O, buffer B: 0.1% TFA/CH$_3$CN)). Fractions judged to be of high purity were pooled and lyophilized.

Purity of the final products was checked by analytical HPLC on a reversed phase column as stated above. Purity of all products was judged to be approximately 95-99%. All final products were also subjected to fast atom bombardment mass spectrometry (FAB-MS) or electrospray mass spectrometry (ES-MS). All products yielded the expected parent M+H ions within acceptable limits.

The compounds of the present invention can be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. Any procedure for obtaining a pharmaceutically acceptable salt known to a skilled artisan can be used.

In the practice of the method of the present invention, an effective amount of any one of the peptides of this invention or a combination of any of the peptides of this invention or a pharmaceutically acceptable salt thereof, is administered via any of the usual and acceptable methods known in the art, either singly or in combination. Administration can be, for example, once a day, once every three days or once a week. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Thus, the method of the present invention is practiced when relief of symptoms is specifically required or perhaps imminent. Alternatively, the method of the present invention is effectively practiced as continuous or prophylactic treatment.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose for intranasal administration is typically in the range of about 0.001 to about 0.1 mg/kg body weight. In humans, the preferred subcutaneous dose based on peptide content is from about 0.001 mg to about 100 mg; preferably from about 0.1 mg to about 15 mg. For the API, it would range from about 0.015 mg to about 100 mg; preferably from about 1 mg to about 100 mg.

The invention will now be further described in the Examples which follow, which are intended as an illustration only and do not limit the scope of the invention.

EXAMPLES

Preparation of Reagent

Preparation of 30 kD Peg-SSA Reagent (5)
mPEG$_{30k}$-Mesylate

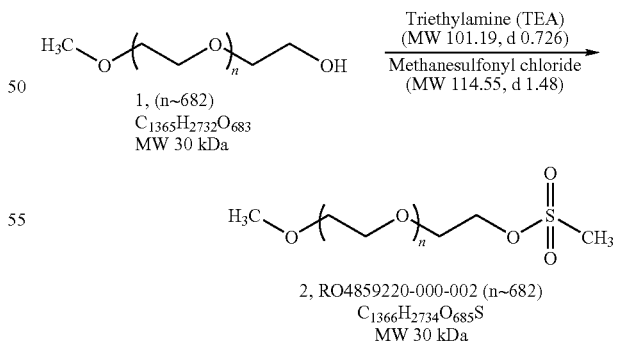

A 1 L round-bottom flask equipped with a magnetic stirrer, dean-stark trap, reflux condenser and argon (or nitrogen) inlet bubbler was charged with 100 g (3.34 mmol) of mPEG 30 kDa (obtained from Nippon Oil and Fat) and 500 mL of toluene. The PEG solution in toluene was azeotropically dried by distilling off 250 mL of toluene then the solution was cooled to room temperature. To the solution 200 mL of anhydrous dichloromethane was added, the solution was cooled to 0-5° C. and 0.67 mL (4.84 mmol) of triethylamine and 0.33 mL (4.34 mmol) of methanesulfonyl chloride were added dropwise using syringe through a rubber septa. The mixture was stirred for 2 hrs at ca. 4° C. and then stirred at room temperature overnight under argon gas.

The mixture was concentrated on a rotary evaporator and was filtered through a coarse glass frit to remove salts. (Caution: warm up the glass frit during the filtration to prevent the solution from solidifying). The product was precipitated by the addition of ca. 1800 ml of cold isopropyl alcohol and diethyl ether (30:70, v/v). The product was collected and dried under vacuum at room temperature overnight to give 90 g (90%) of a white solid.

Step 2. mPEG$_{30k}$-Amine

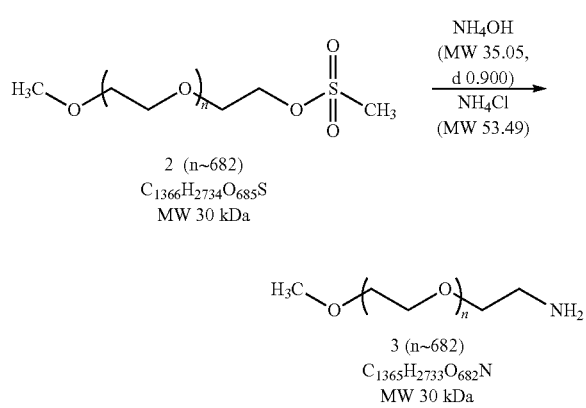

2 (n~682)
C$_{1366}$H$_{2734}$O$_{685}$S
MW 30 kDa 3 (n~682)
C$_{1365}$H$_{2733}$O$_{682}$N
MW 30 kDa

A 2-L, round-bottom flask equipped with a magnetic stirrer and argon (or nitrogen) inlet bubbler was charged with 90 g (3 mmol) of mPEG 30 kDa mesylate 2 prepared above and 1600 mL of ammonium hydroxide aqueous solution (30%, v/v). To this solution 160 g of ammonium chloride was added. The solution was warmed carefully to dissolve all of the PEG mesylate. The resulting solution was stirred at room temperature for 48 h while venting excess gases through a bubbler to prevent pressure buildup in the reaction flask.

After the reaction was complete, 160 g (10 wt %) of sodium chloride was added and the mixture was extracted with 3×200 mL=1200 mL of dichloromethane. The combined organic extracts were dried over anhydrous sodium sulfate for about 1 h, filtered and concentrated on a rotary evaporator. The product was precipitated by addition of 1800 mL of cold diethyl ether, filtered and dried under vacuum at room temperature overnight to give 85 g (94%) of 3 as a white solid.

Step 3. mPEG$_{30k}$-Succinamide Acid (SAA)

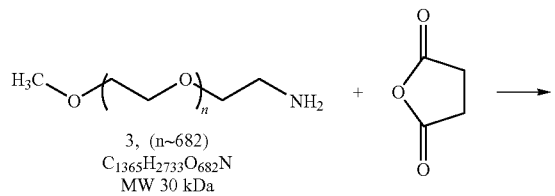

3, (n~682)
C$_{1365}$H$_{2733}$O$_{682}$N
MW 30 kDa

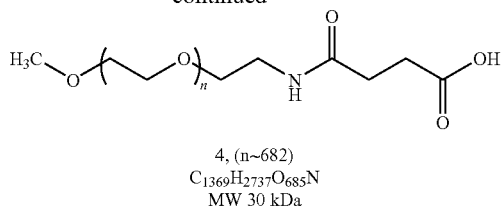

4, (n~682)
C$_{1369}$H$_{2737}$O$_{685}$N
MW 30 kDa

A 1 L, round-bottom flask equipped with a magnetic stirrer and argon inlet bubbler was charged with 60 g (2.00 mmol) of mPEG 30 kDa amine 3 and 500 mL of anhydrous acetonitrile. The solution was cooled down to ca. 4° C., then 2 g (20.00 mmol) of succinic anhydride in 50 mL of anhydrous acetonitrile was added slowly using addition funnel. The reaction mixture was stirred at room temperature overnight under an argon gas flow.

After the reaction was finished, the solvent was evaporated to dryness by rotary evaporator. Then, the product was dissolved in 400 mL of water. The pH of the solution was adjusted to 7.0 with 1 M NaOH solution and stirred for 1 h while maintaining pH at 7.0. To this solution 40 g (10 wt. %) of sodium chloride was added and adjusted the pH to ~4.2 with 6 N HCl solution. The resulting aqueous mixture was extracted with 200, 100, 50 mL=350 mL of dichloromethane. The combined organic extracts were dried over anhydrous sodium sulfate for about 1 h. Filter off the sodium sulfate and concentrate filtrate on a rotary evaporator. Precipitate the product in 1 L of cold diethyl ether. Collect the product and dry it under vacuum at room temperature overnight to give 56 g (93%) of 4 as a white solid.

Step 4. mPEG$_{30k}$-Succinimidyl Succinamide (SSA)

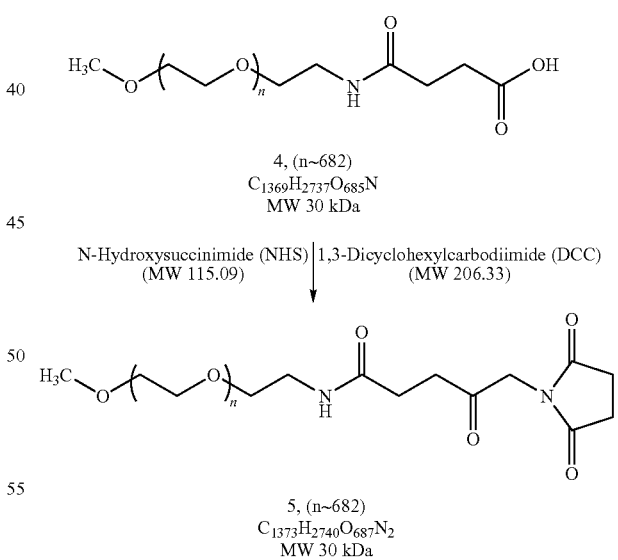

A 500-mL, round-bottom flask equipped with a magnetic stirrer and argon inlet bubbler was charged with 56 g (1.87 mmol) of mPEG 30 kDa Succinamide Acid 4 and 500 mL of anhydrous dichloromethane. To this solution 0.24 g (2.05 mmol) of N-hydroxysuccinimide and 0.46 g (2.24 mmol) of 1,3-dicyclohexylcarbodiimide were added slowly. The reaction mixture was stirred at room temperature overnight under argon gas flow.

After the reaction was complete, the mixture was evaporated to dryness on a rotary evaporator. Then, the product was dissolved in 200 mL of anhydrous toluene and the solution was filtered through a pre-warmed coarse glass frit laid with a pad of celite. The product was precipitated by addition of 1200 mL of cold anhydrous isopropyl alcohol and diethyl ether (30:70, v/v). The product was collected and dried under vacuum at room temperature overnight to give 20 g (80%) of 5 as a white solid.

Preparation of Preferred Compounds

Example 1

Preparation of Fmoc-Linker-BHA Resin

Benzhydrylamine copolystyrene-1% divinylbenzene cross-linked resin (10.0 g, 9.3 mequiv, 100-200 ASTM mesh, Advanced ChemTech) was swelled in 100 mL $CH_2Cl_2$, filtered and washed successively with 100 ml each of $CH_2Cl_2$, 6% DIPEA/$CH_2Cl_2$ (two times), $CH_2Cl_2$ (two times). The resin was treated with p-((R,S)-α-(1-(9H-fluoren-9-yl)-methoxyformamido)-2,4-dimethoxybenzyl)-phenoxyacetic acid (Fmoc-Linker) (7.01 g, 13.0 mmole), N-hydroxybenzotriazole (2.16 g, 16.0 mmole), and diisopropyl-carbodiimide (2.04 ml, 13.0 mmol) in 100 mL 25% DMF/$CH_2Cl_2$ for 24 hours at room temperature. The resin was filtered and washed successively with 100 ml each of $CH_2Cl_2$ (two times), isopropanol (two times), DMF, and $CH_2C_1$, (three times). A Kaiser Ninhydrin analysis was negative. The resin was dried under vacuum to yield 16.12 g of Fmoc-Linker-BHA resin. A portion of this resin (3.5 mg) was subjected to Fmoc deprotection and quantitative UV analysis which indicated a loading of 0.56 mmol/g.

Example 2

Protocol for the Synthesis of Peptides by Applied Biosystem 433A Synthesizer Using Fluorenylmethyloxycarbonyl (Fmoc) chemistry For a 0.25 mmol scale peptide synthesis by Applied Biosystem 433A synthesizer (Foster City, Calif.), the FastMoc 0.25 mmole cycles were used with either the resin sampling or non resin sampling, 41 mL reaction vessel. The Fmoc-amino acid resin was dissolved with 2.1 g NMP, 2 g of 0.45M HOBT/HBTU in DMF and 2M DIEA, then transferred to the reaction vessel. The basic FastMoc coupling cycle was represented by the module "BADEIFD," wherein each letter represents a module. For example:

B represents the module for Fmoc deprotection using 20% Piperidine/NMP and related washes and readings for 30 min (either UV monitoring or conductivity); A represents the module for activation of amino acid in cartridges with 0.45 M HBTU/HOBt and 2.0 M DIEA and mixing with $N_2$ bubbling; D represents the module for NMP washing of resin in the reaction vessel; E represents the module for transfer of the activated amino acid to the reaction vessel for coupling; I represents the module for a 10 minute waiting period with vortexing on and off of the reaction vessel; and F represents the module for cleaning cartridge, coupling for approximately 10 minutes and draining the reaction vessel. Couplings were typically extended by addition of module "I" once or multiple times. For example, double couplings were run by performing the procedure "BADEIIADEIFD." Other modules were available such as c for methylene chloride washes and "C" for capping with acetic anhydride. Individual modules were also modifiable by, for example, changing the timing of various functions, such as transfer time, in order to alter the amount of solvent or reagents transferred. The cycles above were typically used for coupling one amino acid. For synthesizing tetra peptides, however, the cycles were repeated and strung together. For example, BADEIIADEIFD was used to couple the first amino acid, followed by BADEI-IADEIFD to couple the second amino acid, followed by BADEIIADEIFD to couple the third amino acid, followed by BADEIIADEIFD to couple the fourth amino acid, followed by BIDDcc for final deprotection and washing.

Example 3

Preparation of H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-The-Arg-Gln-Arg-Tyr-$NH_2$ (SEQ ID NO: 1)($PYY_{3-36}$)

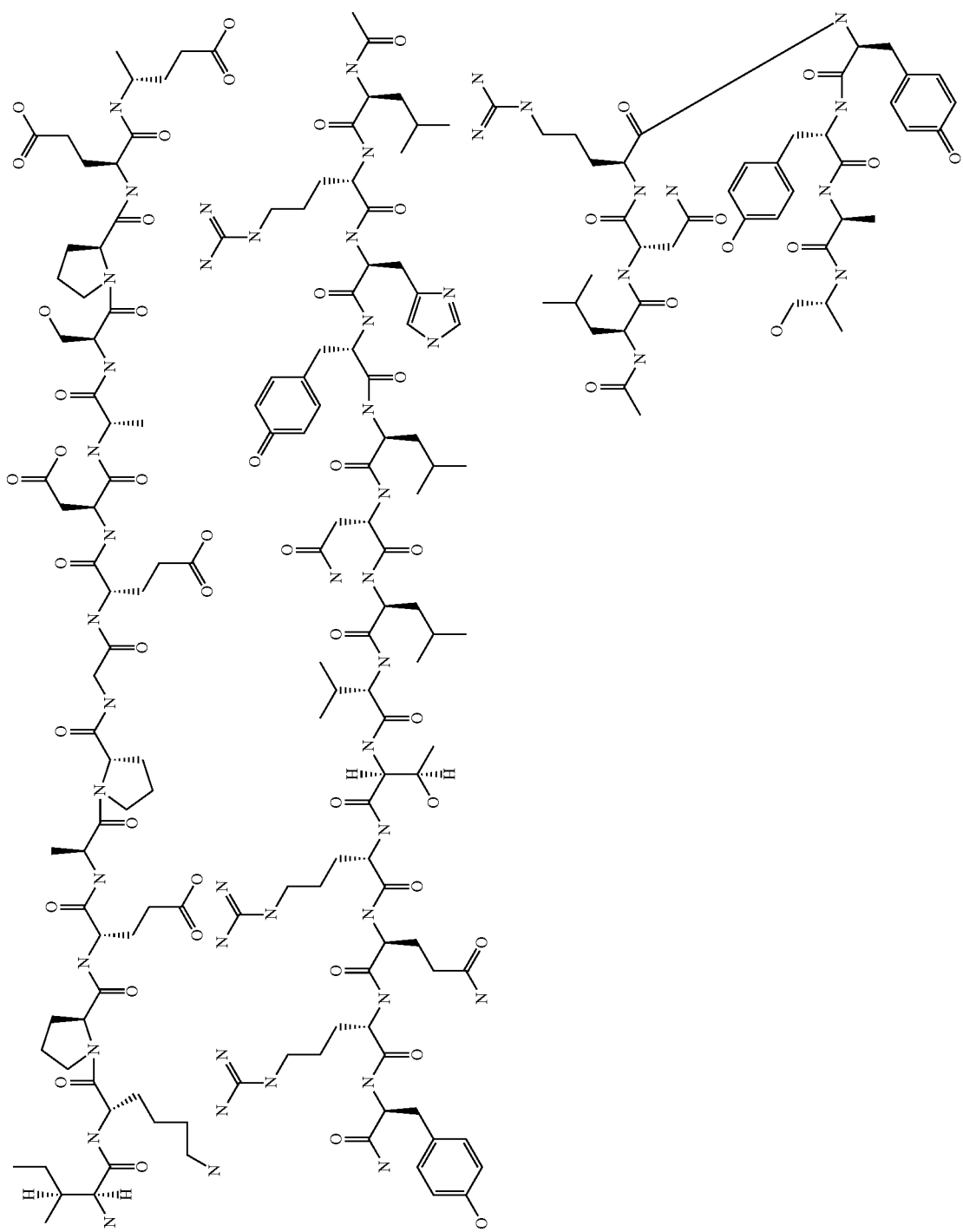

The above peptide was synthesized using Fmoc chemistry on an Applied Biosystem 433A synthesizer. The synthesizer was programmed for double coupling using the modules described in Example 2. The synthesis was carried out on a 0.25 mmol scale using the Fmoc-Linker-BHA resin (450 mg, 0.25 mmol) from Example 1. At the end of the synthesis, the resin was transferred to a reaction vessel on a shaker for cleavage. The peptide was cleaved from the resin using 13.5 mL 97% TFA/3% H2O and 1.5 mL triisopropylsilane for 180 minutes at room temperature. The deprotection solution was added to 100 mL cold $ET_2O$, and washed with 1 mL TFA and 30 mL cold $ET_2O$ to precipitate the peptide. The peptide was centrifuged 2×50 mL polypropylene tubes. The precipitates from the individual tubes were combined in a single tube and washed 3 times with cold $ET_2O$ and dried in a desiccator under house vacuum.

The crude material was purified by preparative HPLC on a Pursuit C18-Column (250×50 mm, 10 μm particle size) and eluted with a linear gradient of 2-70% B (buffer A: 0.1% TFA/$H_2O$; buffer B: 0.1% TFA/CH3CN) in 90 min., flow rate 60 mL/min, and detection 220/280 nm. The fractions were collected and were checked by analytical HPLC. Fractions containing pure product were combined and lyophilized to yield 151 mg (15%) of a white amorphous powder. (ES)+-LCMS m/e calculated ("calcd") for $C_{180}H_{279}N_{53}O_{54}$ 4049.55 found 4050.40

Example 4

Preparation of H-Ile-Lys-Pqa-Arg-His-Tyr-Leu-Asn-Leu-Val-Thr-Arg-Gln-Arg-Tyr-$NH_2$ (SEQ ID NO: 2)

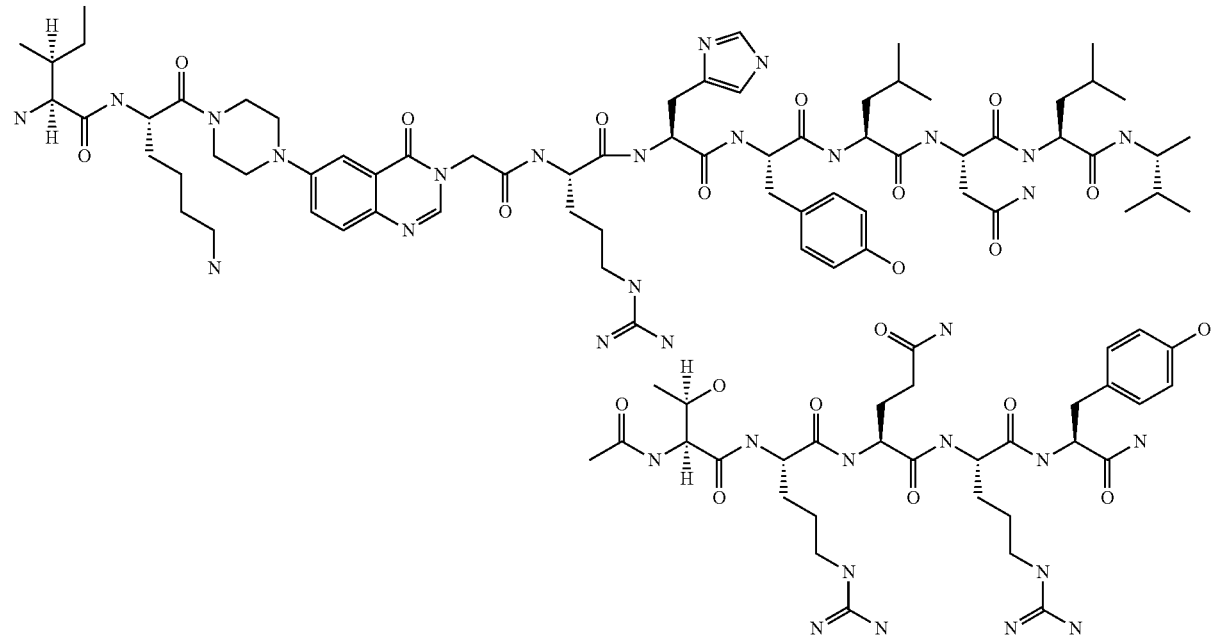

Fmoc-Linker-BHA resin (450 mg, 0.25 mmol) from Example 1 was subjected to solid phase synthesis and purification by following the procedure in Example 3 to yield 48 mg (9%) of white amorphous powder. (ES)+-LCMS m/e calcd for $C_{98}H_{155}N_{33}O_{21}$ 2131.53 found 2130.56.

Example 5

Preparation of H-Ile-Lys-Pqa-Arg-His-Tyr-Leu-Asn-Leu-Val-Thr-Arg-Gln-(NMe)Arg-Tyr-$NH_2$ (SEQ ID NO: 3)

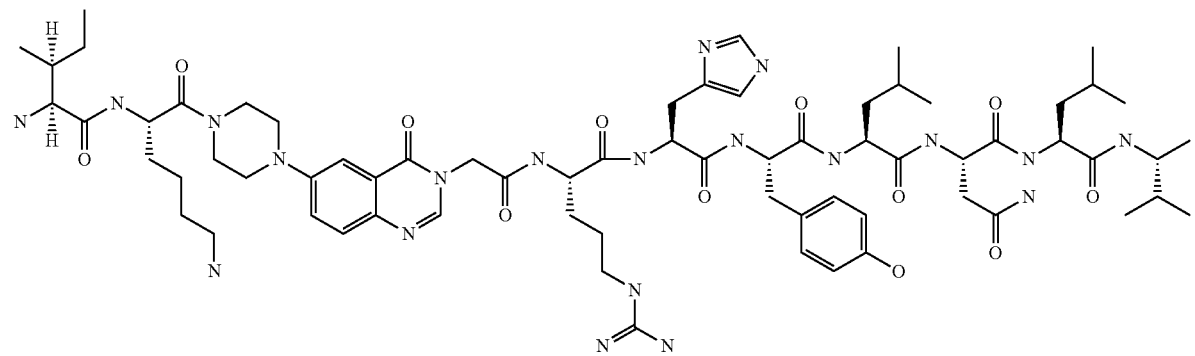

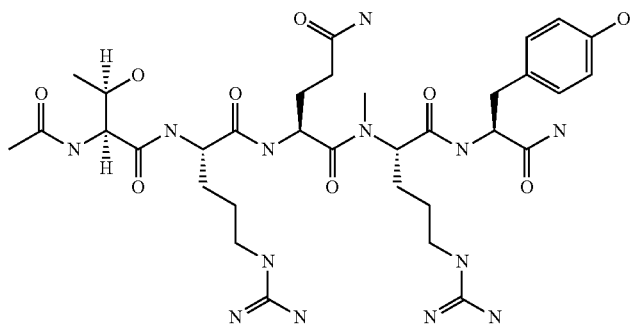

Fmoc-Linker-BHA resin (450 mg, 0.25 mmol) from Example 1 was subjected to solid phase synthesis (N-methyl Arg was inserted in position 35 of the sequence) and purification by following the procedure in Example 3 to yield 32 mg (6%) of white amorphous powder. (ES)+-LCMS m/e calcd for $C_{99}H_{155}N_{33}O_{21}$ 2143.56 found 2143.50

Example 6

Preparation of H-Ile-Lys-Pqa-Arg-His-Tyr-Leu-Asn-Leu-Val-Thr-Arg-Gln-(NMe)Arg-m-Tyr-NH$_2$ (SEQ ID NO: 4)

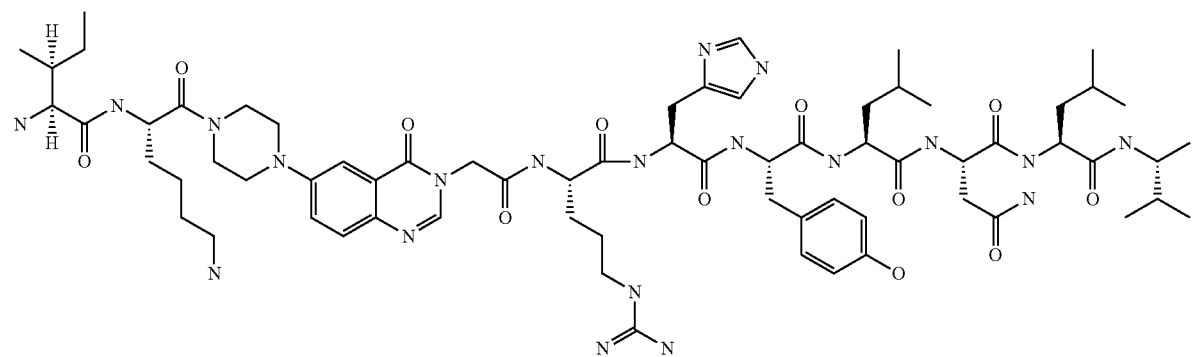

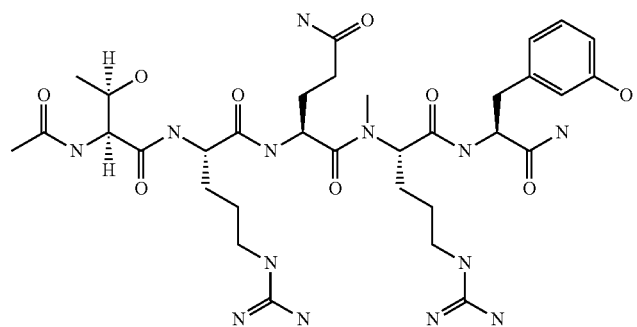

Fmoc-Linker-BHA resin (450 mg, 0.25 mmol) from Example 1 was subjected to solid phase synthesis and purification by following procedure in Example 3 to yield 38.5 mg (7%) of white amorphous powder. (ES)+-LCMS m/e calcd for C99H155N33O21 2143.5477 found 2143.50.

Example 7

Preparation of H-Ile-Lys-Pqa-Arg-His-Tyr-Leu-Asn-Leu-Val-Thr-Arg-Gln-(NMe)Arg-3-iodo-Tyr-NH$_2$
(SEQ ID NO: 5)

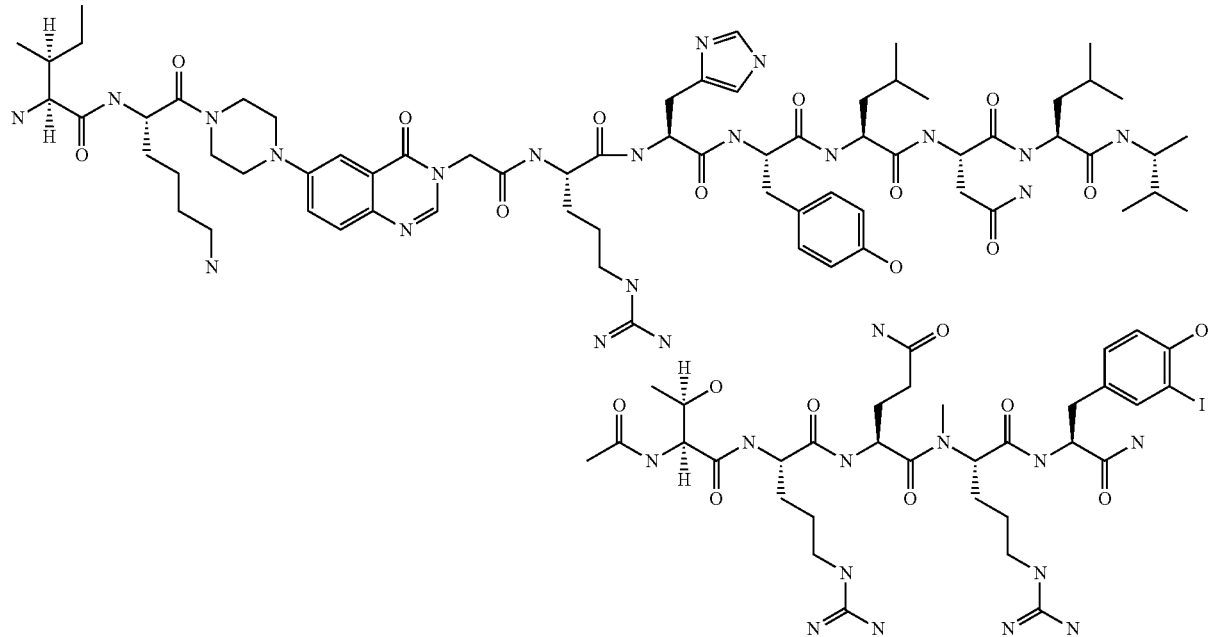

Fmoc-Linker-BHA resin (450 mg, 0.25 mmol) from Example 1 was subjected to solid phase synthesis and purification by following procedure in Example 3 to yield 41 mg (7%) of white amorphous powder. (ES)+-LCMS m/e calcd for C99H154IN33O21 2269.44 found 2269.20.

Example 8

Preparation of H-Ile-Lys-Pqa-Arg-His-Tyr-Leu-Asn-Leu-Val-Thr-Arg-Gln-(NMe)Arg-3,5 di F-Tyr-NH$_2$
(SEQ ID NO: 6)

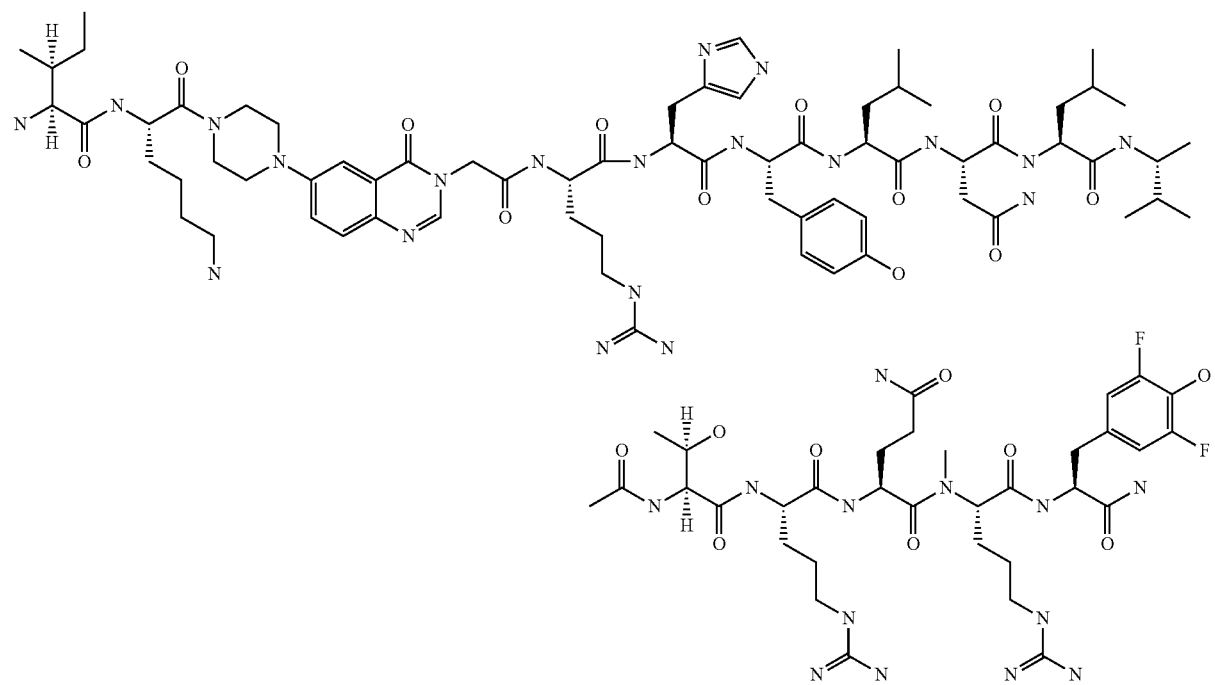

Fmoc-Linker-BHA resin (450 mg, 0.25 mmol) from Example 1 was subjected to solid phase synthesis and purification by following procedure in Example 3 to yield 28 mg (5%) of white amorphous powder. (ES)+-LCMS m/e calcd for C99H153F2N33O21 2179.52 found 2179.46.

Example 9

Preparation of H-Ile-Lys-Pqa-Arg-His-Tyr-Leu-Asn-Leu-Val-Thr-Arg-Gln-(NMe)Arg-2,6 di F-Tyr-NH$_2$
(SEQ ID NO: 7)

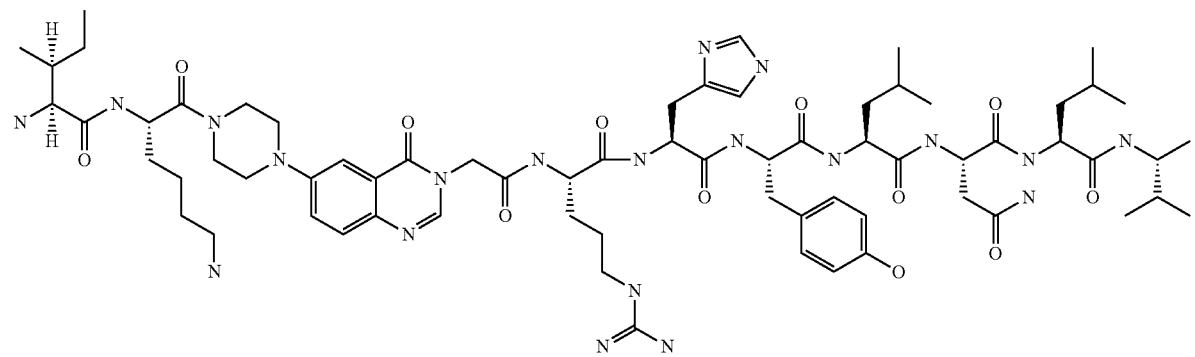

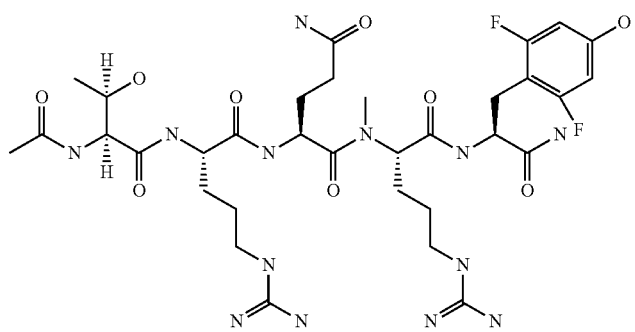

Fmoc-Linker-BHA resin (450 mg, 0.25 mmol) from Example 1 was subjected to solid phase synthesis and purification by following procedure in Example 3 to yield 49.3 mg (9%) of white amorphous powder. (ES)+-LCMS m/e calcd for C99H153F2N33O21 2179.53 found 2179.50.

Example 10

Preparation of H-Ile-Lys-Pqa-Arg-His-Tyr-Leu-Asn-Leu-Val-Thr-Arg-Gln-(NMe)Arg-2,6 di Me-Tyr-NH,
(SEQ ID NO:8)

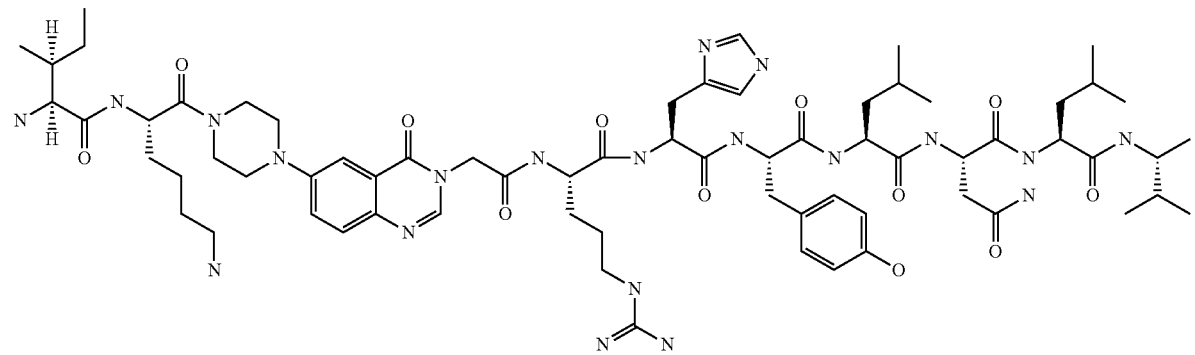

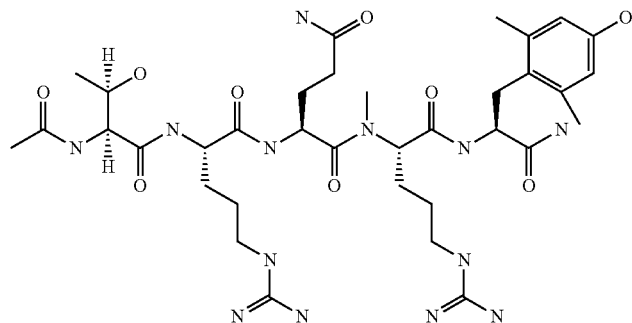

Fmoc-Linker-BHA resin (450 mg, 0.25 mmol) from Example 1 was subjected to solid phase synthesis and purification by following procedure in Example 3 to yield 13.5 mg (3%) of white amorphous powder. (ES)+-LCMS m/e calcd for C101H159N33O21 2171.60 found 2171.40.

Example 11

Preparation of H-Ile-Lys-Pqa-Arg-His-Tyr-Leu-Asn-Leu-Val-Thr-Arg-Gln-(NMe)Arg-4 Methoxy-Phe-NH$_2$ (SEQ ID NO: 9)

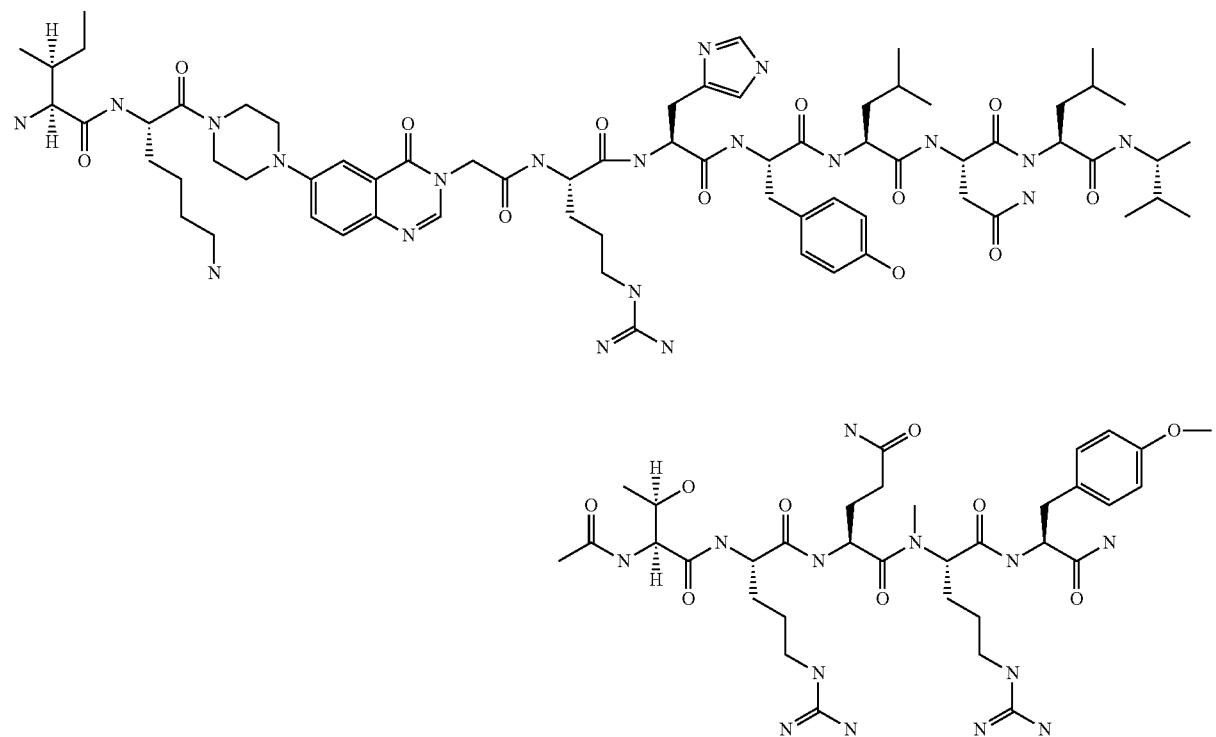

Fmoc-Linker-BHA resin (450 mg, 0.25 mmol) from Example 1 was subjected to solid phase synthesis and purification by following procedure in Example 3 to yield 72 mg (13%) of white amorphous powder. (ES)+-LCMS m/e calcd for C100H157N33O21 2157.57 found 2157.58.

Example 12

Preparation of H-Ile-Lys-Pqa-Arg-His-Tyr-Leu-Asn-Leu-Val-Thr-Arg-Gln-(NMe)Arg-Phe-NH$_2$ (SEQ ID NO: 10)

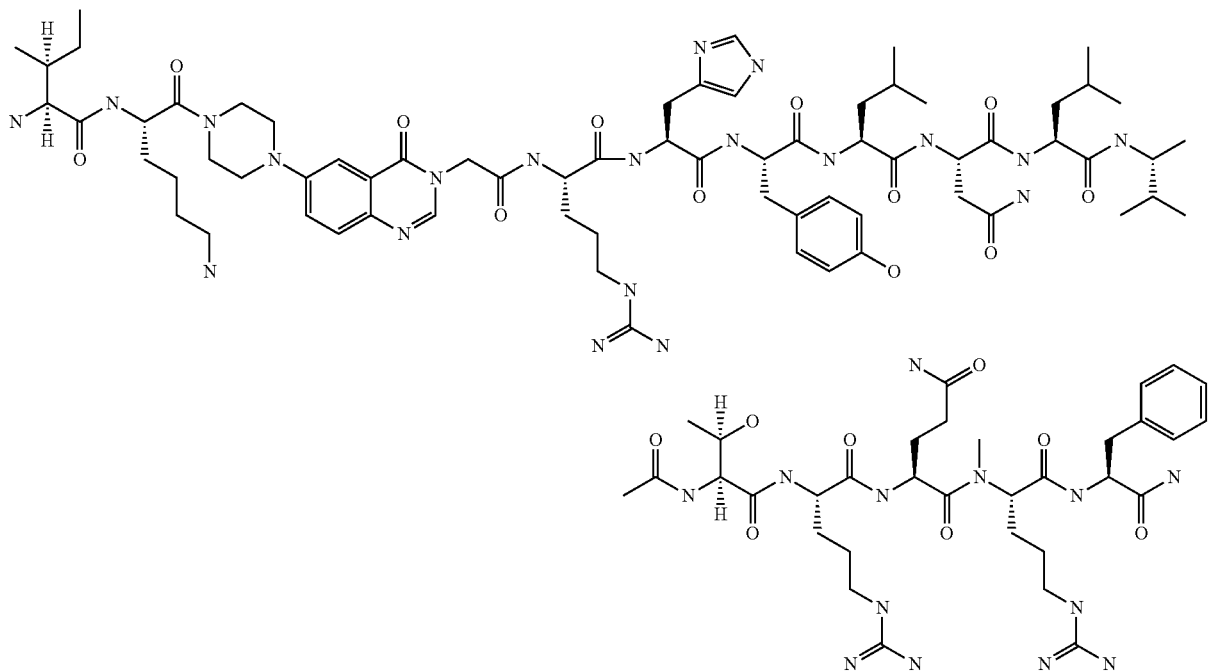

Fmoc-Linker-BHA resin (450 mg, 0.25 mmol) from Example 1 was subjected to solid phase synthesis and purification by following procedure in Example 3 to yield 85.3 mg (16%) of white amorphous powder. (ES)+-LCMS m/e calcd for C99H155N33O20 2127.55 found 2127.53.

Example 13

Preparation of H-Ile-Lys-Pqa-Arg-His-Tyr-Leu-Asn-Leu-Val-Thr-Arg-Gln-(NMe)Arg-4 amino-Phe-NH$_2$ (SEQ ID NO: 11)

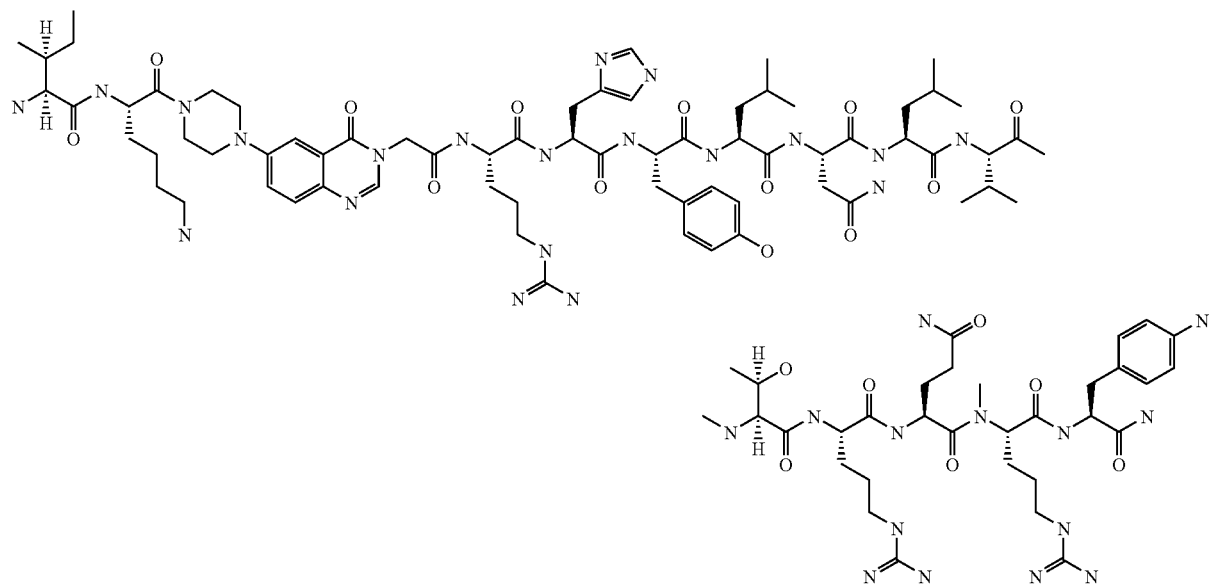

Fmoc-Linker-BHA resin (450 mg, 0.25 mmol) from Example 1 was subjected to solid phase synthesis and purification by following procedure in Example 3 to yield 51.4 mg (10%) of white amorphous powder. (ES)+-LCMS m/e calcd for C99H156N34O20 2142.56 found 2142.55.

Example 14

Preparation of H-Ile-Lys-Pqa-Arg-His-Tyr-Leu-Asn-Leu-Val-Thr-Arg-Gln-(NMe)Arg-4 F-Phe-NH₂ (SEQ ID NO: 12)

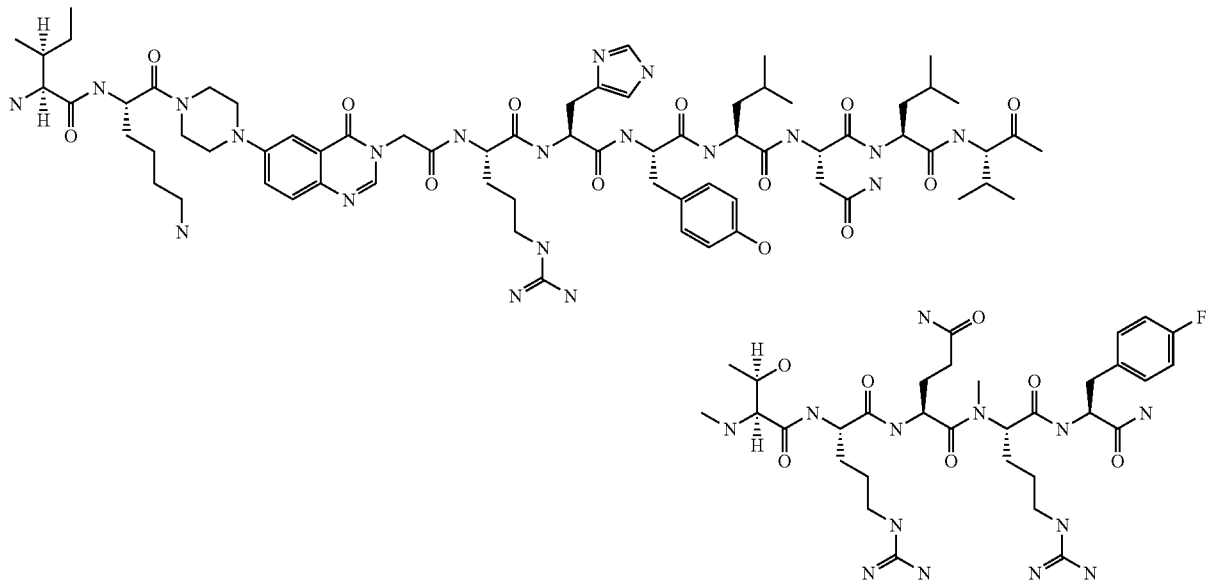

Fmoc-Linker-BHA resin (450 mg, 0.25 mmol) from Example 1 was subjected to solid phase synthesis and purification by following procedure in Example 3 to yield 35 mg (7%) of white amorphous powder. (ES)+-LCMS m/e calcd for C99H154FN33O20 2145.54 found 2145.51.

Example 15

Preparation of H-Ile-Lys-Pqa-Arg-His-Tyr-Leu-Asn-Leu-Val-Thr-Arg-Gln-(NMe)Arg-4-(CH2OH)-Phe-NH₂ (SEQ ID NO: 13)

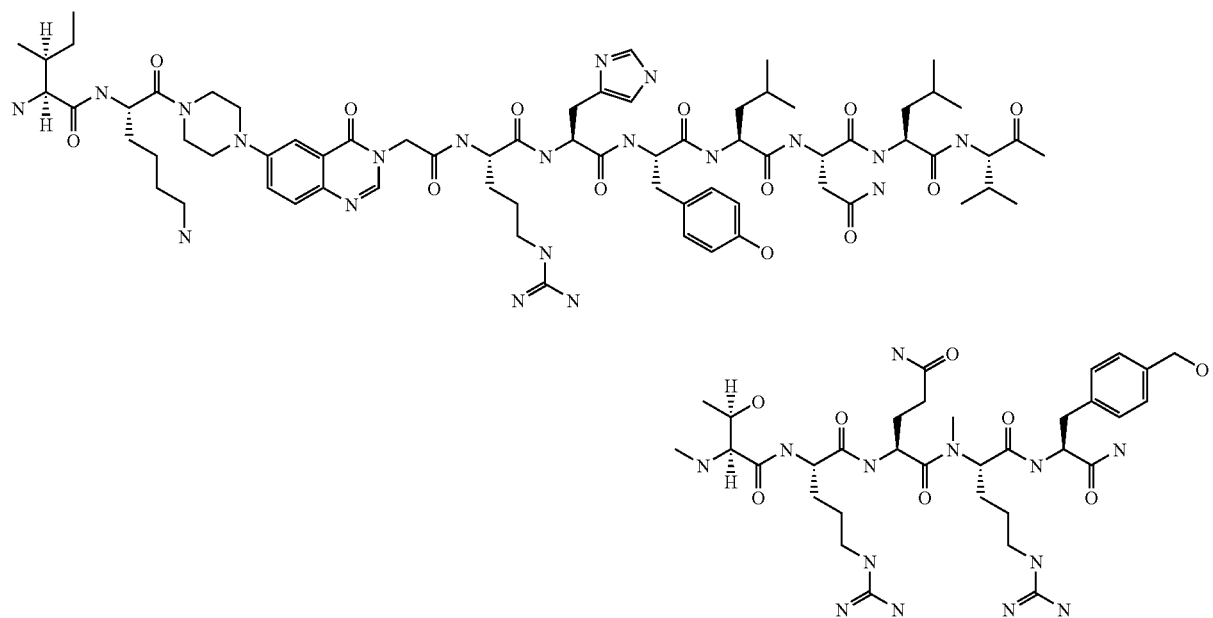

Fmoc-Linker-BHA resin (450 mg, 0.25 mmol) from Example 1 was subjected to solid phase synthesis and purification by following procedure in Example 3 to yield 24 mg (4%) of white amorphous powder. (ES)+-LCMS m/e calcd for C100H157N33O21 2157.57 found 2157.56.

Example 16

Preparation of H-Ile-Lys-Pqa-Arg-His-Tyr-Leu-Asn-Leu-Val-Thr-Arg-Gln-(NMe)Arg-4-trifluoro methyl-Phe-NH$_2$(SEQ ID NO: 14)

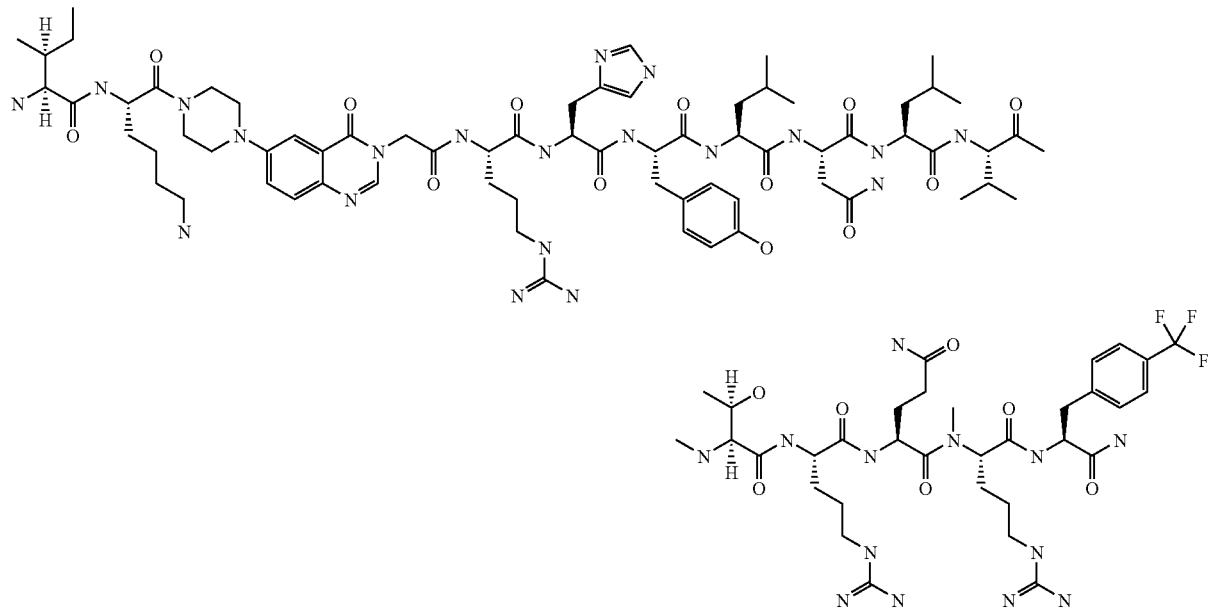

Fmoc-Linker-BHA resin (450 mg, 0.25 mmol) from Example 1 was subjected to solid phase synthesis and purification by following procedure in Example 3 to yield 81 mg (15%) of white amorphous powder. (ES)+-LCMS m/e calcd for C100H154F3N33O20 2195.54 found 2195.51.

Example 17

Preparation of H-Ile-Lys-Pqa-Arg-His-Tyr-Leu-Asn-Leu-Val-Thr-Arg-Gln-(NMe)Arg-3-Fluoro-Phe-NH$_2$ (SEQ ID NO: 15)

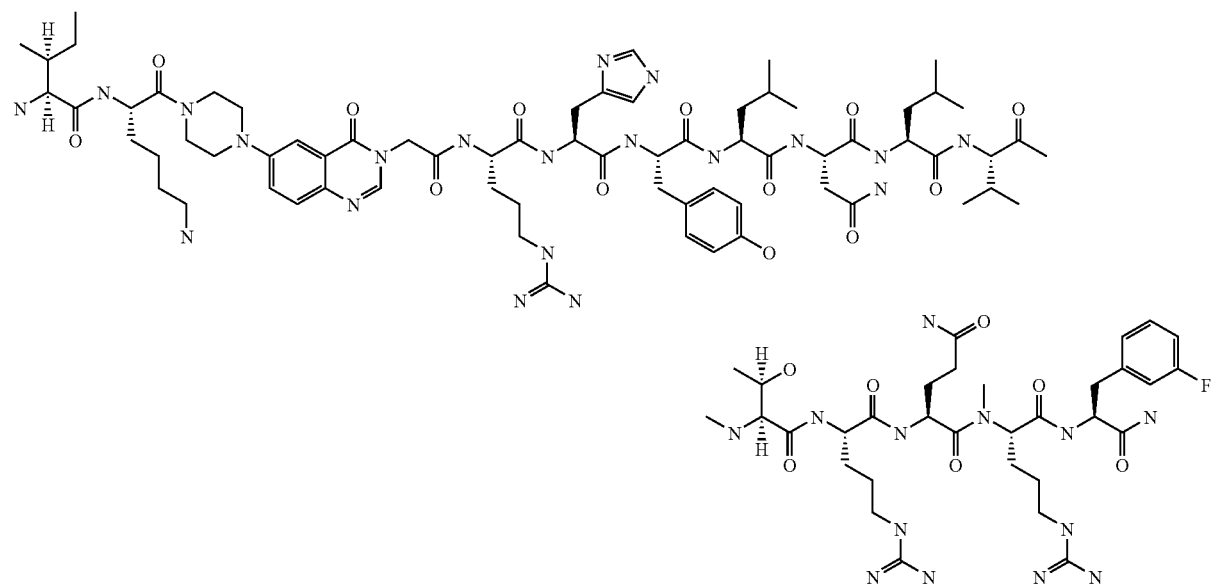

Fmoc-Linker-BHA resin (450 mg, 0.25 mmol) from Example 1 was subjected to solid phase synthesis and purification by following procedure in Example 3 to yield 84 mg (16%) of white amorphous powder. (ES)+-LCMS m/e calcd for C99H154FN33O20 2145.54 found 2145.53.

Example 18

Preparation of H-Ile-Lys-Pqa-Arg-His-Tyr-Leu-Asn-Leu-Val-Thr-Arg-Gln-(NMe)Arg-2,3,4,5,6 Penta fluoro-Phe-NH₂ (SEQ ID NO: 16)

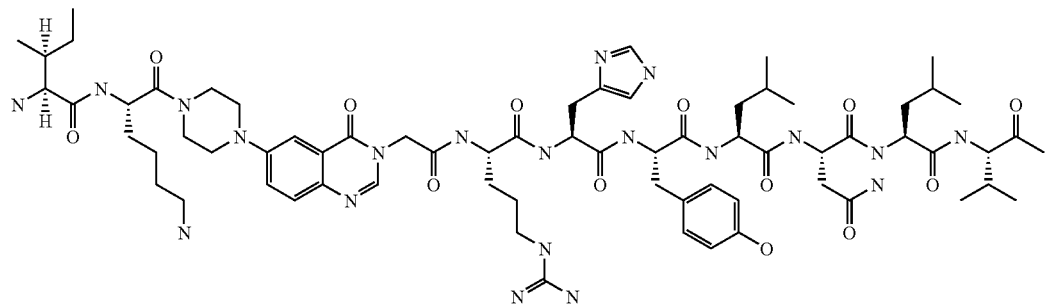
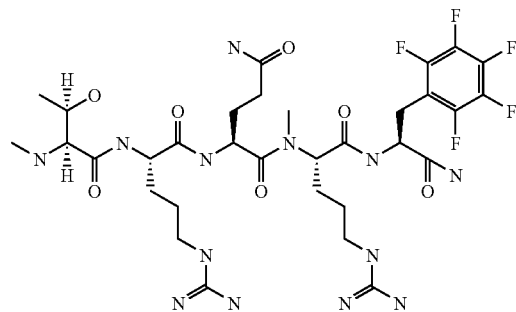

Fmoc-Linker-BHA resin (450 mg, 0.25 mmol) from Example 1 was subjected to solid phase synthesis and purification by following procedure in Example 3 to yield 89 mg (16%) of white amorphous powder. (ES)+-LCMS m/e calcd for C99H150FN33O20 2217.50 found 2217.48.

Example 19

Preparation of H-Ile-Lys-Pqa-Arg-His-Tyr-Leu-Asn-Leu-Val-Thr-Arg-Gln-(NMe)Arg-3,4-dichloro-Phe-NH₂ (SEQ ID NO: 17)

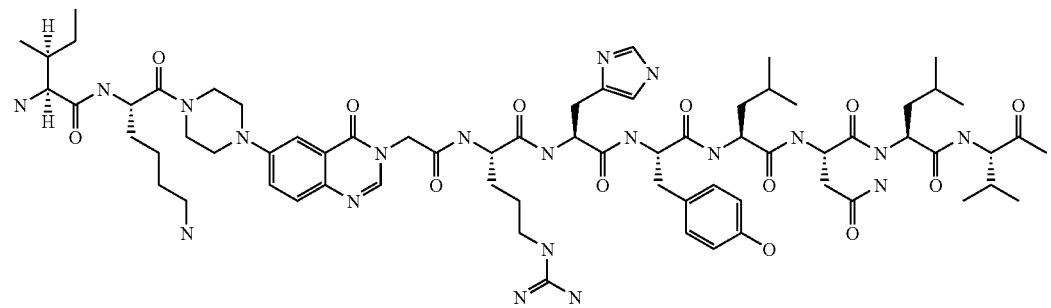
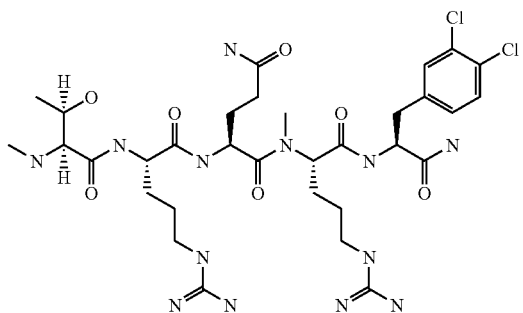

Fmoc-Linker-BHA resin (450 mg, 0.25 mmol) from Example 1 was subjected to solid phase synthesis and purification by following procedure in Example 3 to yield 46 mg (8%) of white amorphous powder. (ES)+-LCMS m/e calcd for C99H153Cl2N33O20 2196.44 found 2196.41.

Example 20

Preparation of H-Ile-Lys-Pqa-Arg-His-Tyr-Leu-Asn-Leu-Val-Thr-Arg-Gln-(NMe)Arg-Cha-NH$_2$ (SEQ ID NO: 18)

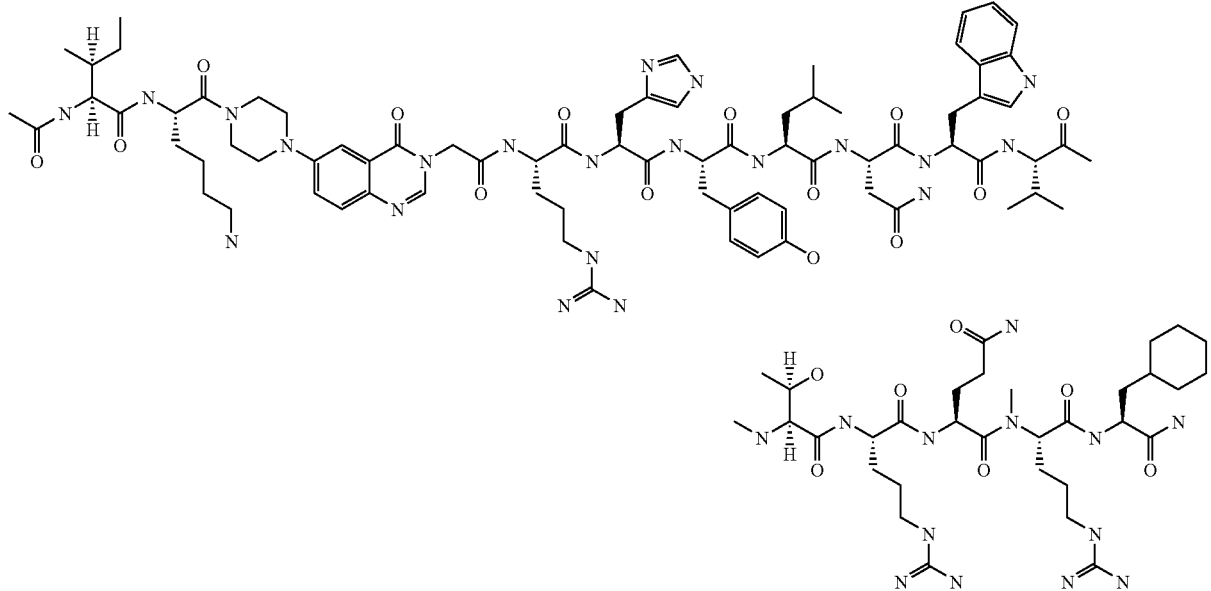

Fmoc-Linker-BHA resin (450 mg, 0.25 mmol) from Example 1 was subjected to solid phase synthesis and purification by following procedure in Example 3 to yield 49 mg (9%) of white amorphous powder. (ES)+-LCMS m/e calcd for C106H162N34O21 2248.69 found 2248.71.

Example 21

Preparation of H-Ile-Lys-Pqa-Arg-His-Tyr-Leu-Asn-Leu-Val-Thr-Arg-Gln-(NMe)Arg-Trp-NH$_2$ (SEQ ID NO: 19)

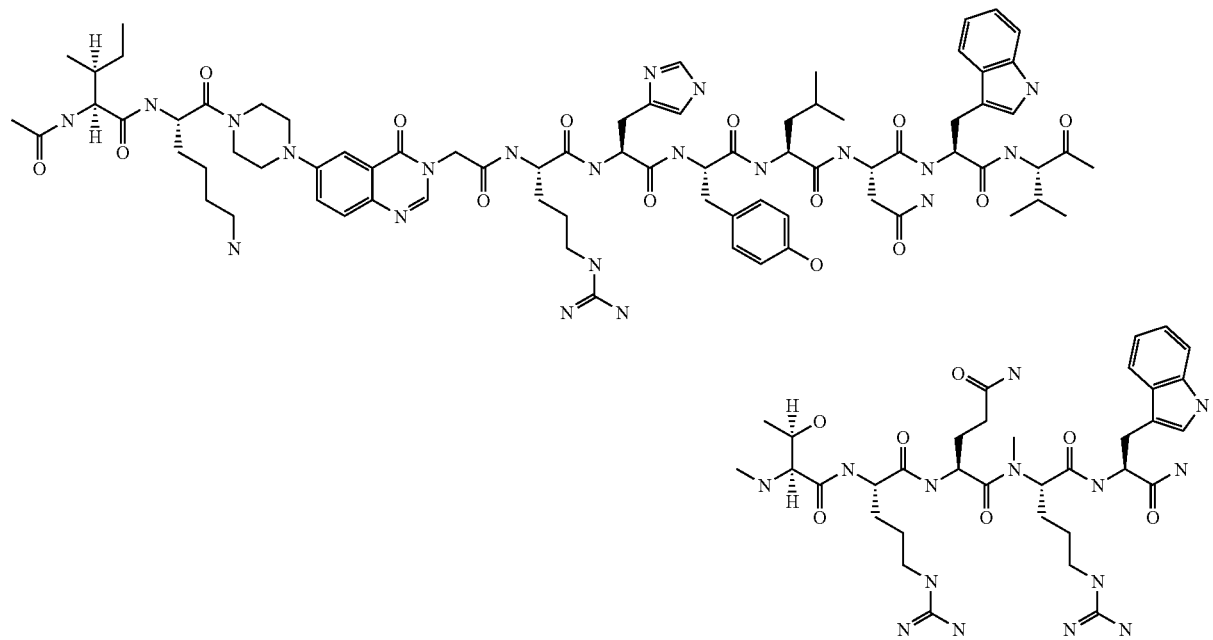

Fmoc-Linker-BHA resin (450 mg, 0.25 mmol) from Example 1 was subjected to solid phase synthesis and purification by following procedure in Example 3 to yield 57 mg (10%) of white amorphous powder. (ES)+-LCMS m/e calcd for C108H157N35O21 2281.68 found 2281.67.

Example 22

Preparation of H-Ile-Lys-Pqa-Arg-His-Tyr-Leu-Asn-Leu-Val-Thr-Arg-Gln-(NMe)Arg-1-Nal-NH₂ (SEQ ID NO: 20)

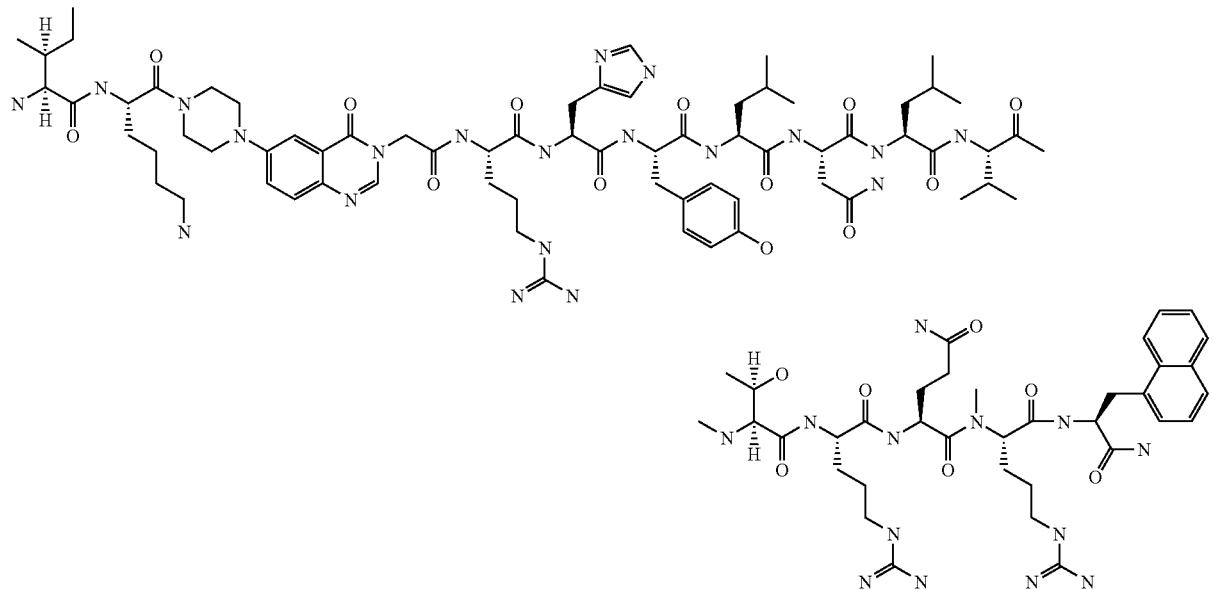

Fmoc-Linker-BHA resin (450 mg, 0.25 mmol) from Example 1 was subjected to solid phase synthesis and purification by following procedure in Example 3 to yield 45 mg (8%) of white amorphous powder. (ES)+-LCMS m/e calcd for C103H157N33O20 2177.61 found 2177.59.

Example 23

Preparation of H-De-Lys-Pqa-Arg-His-Tyr-Leu-Asn-Leu-Val-Thr-Arg-Gln-(NMe)Arg-2-Nal-NH₂ (SEQ ID NO: 21)

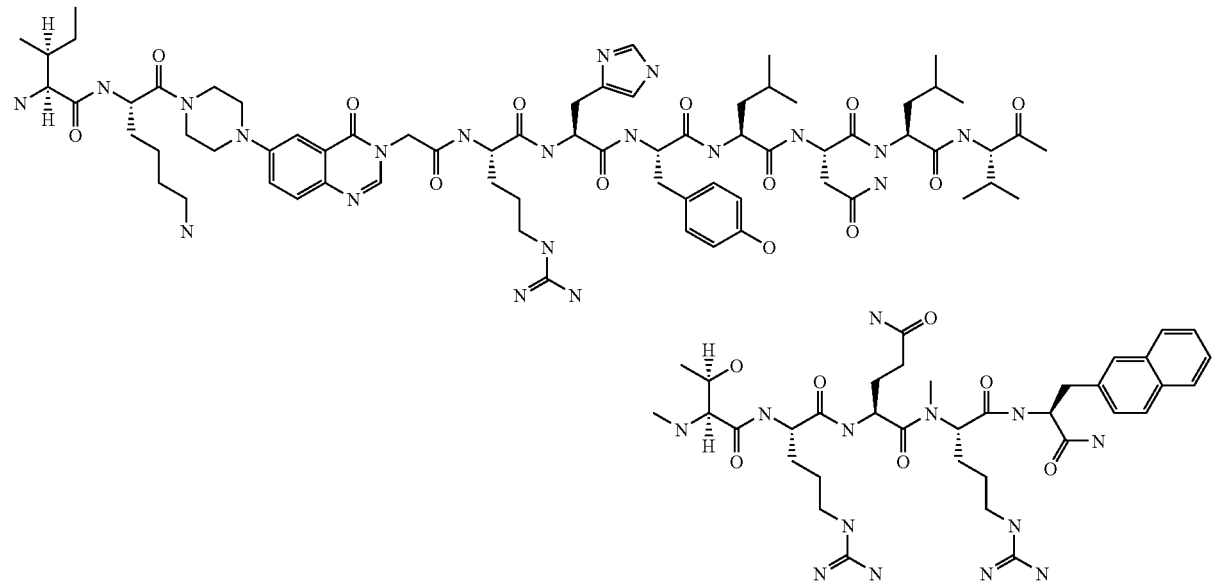

Fmoc-Linker-BHA resin (450 mg, 0.25 mmol) from Example 1 was subjected to solid phase synthesis and purification by following procedure in Example 3 to yield 43 mg (8%) of white amorphous powder. (ES)+-LCMS m/e calcd for C103H157N33O20 2177.60 found 2177.58.

Example 24

Preparation of H-Ile-Lys-Pqa-Arg-His-Tyr-Leu-Asn-Leu-Val-Thr-Arg-Gln-Arg-C-α-methyl Tyr—NH₂ (SEQ ID NO: 221

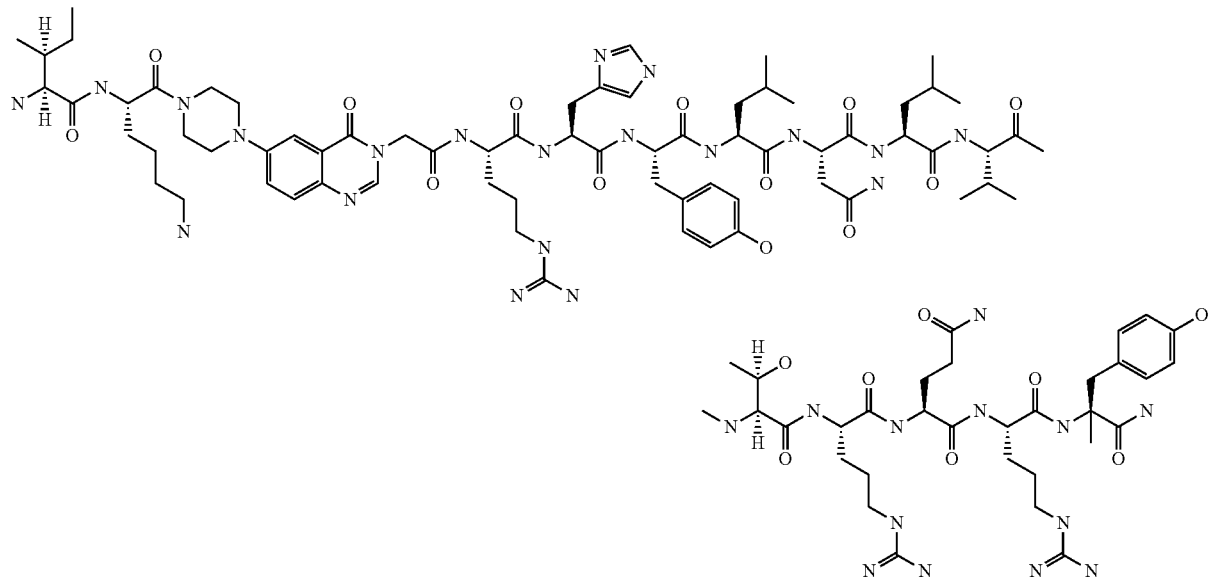

Fmoc-Linker-BHA resin (450 mg, 0.25 mmol) from Example 1 was subjected to solid phase synthesis and purification by following procedure in Example 3 to yield 35.1 mg (7%) of white amorphous powder. (ES)+-LCMS m/e calcd for C99H155N33O21 2143.55 found 2143.56.

Example 25

Preparation of H-Ile-Lys-Pqa-Arg-His-Tyr-Leu-Asn-Trp-Val-Thr-Arg-Gln-(NMe)Arg-Tyr-NH₂ (SEQ ID NO: 23)

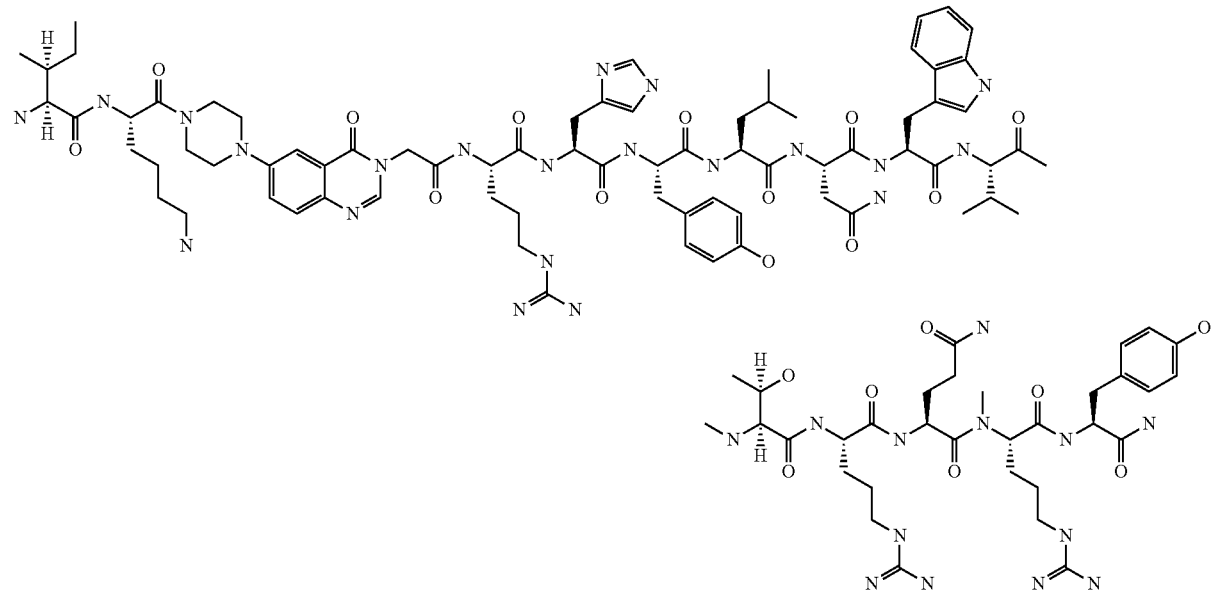

Fmoc-Linker-BHA resin (450 mg, 0.25 mmol) from Example 1 was subjected to solid phase synthesis and purification by following procedure in Example 3 to yield 130 mg (23%) of white amorphous powder. (ES)+-LCMS m/e calcd for C104H154N34O21 2216.60 found 2216.62.

Example 26

Preparation of H-Ile-Nle-Pqa-Arg-His-Tyr-Leu-Asn-Trp-Val-Thr-Arg-Gln-(NMe)Arg-Tyr-NH$_2$ (SEQ ID NO: 24)

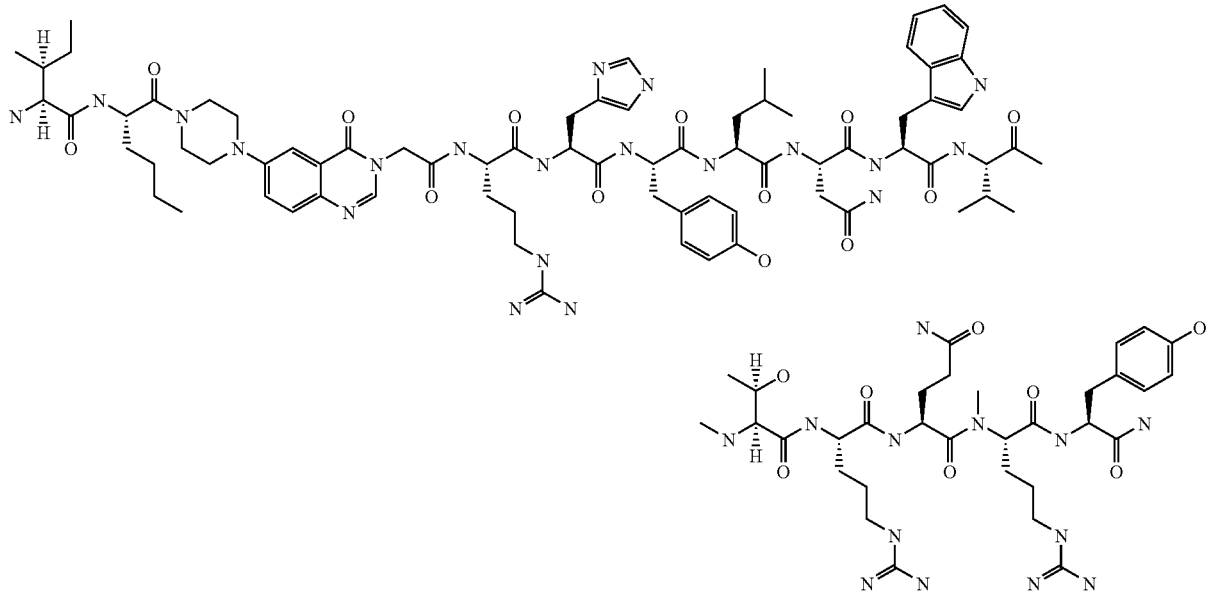

Fmoc-Linker-BHA resin (450 mg, 0.25 mmol) from Example 1 was subjected to solid phase synthesis and purification by following procedure in Example 3 to yield 84 mg (15%) of white amorphous powder. (ES)+-LCMS m/e calcd for C104H153N33O21 2201.59 found 2201.56.

Example 27

Preparation of Ac-Ile-Lys-Pqa-Arg-His-Tyr-Leu-Asn-Trp-Val-Thr-Arg-Gln-(NMe)Arg-2,6-F2-Tyr-NH2 (SEQ ID NO: 25)

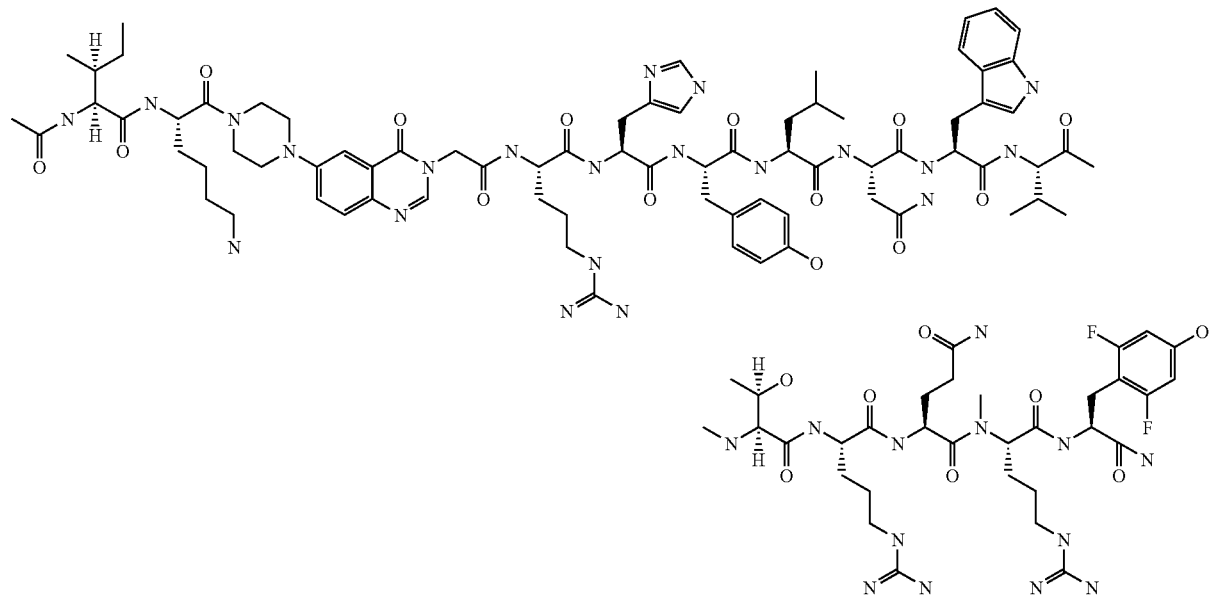

Fmoc-Linker-BHA resin (450 mg, 0.25 mmol) from Example 1 was subjected to solid phase synthesis and purification by following procedure in Example 3 to yield 24 mg (4%) of white amorphous powder. (ES)+-LCMS m/e calcd for C106H154F2N34O22 2099.49 found 2100.3

Example 28

Preparation of Ac-Ile-Lys-Pqa-Arg-His-Tyr-Leu-Asn-Trp-Val-Thr-Arg-Gln-(NMe)Arg-Tyr-NH$_2$ (SEQ ID NO: 26)

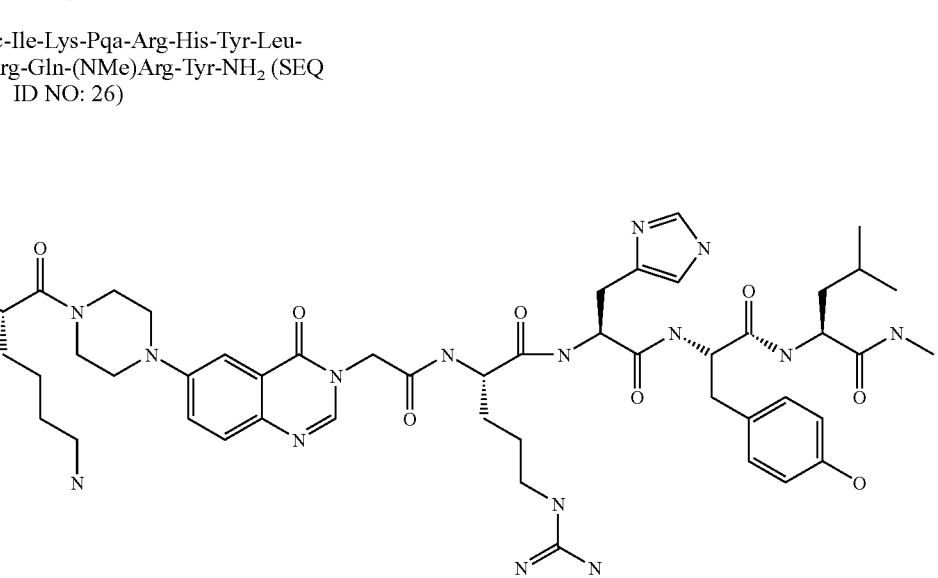

Fmoc-Linker-BHA resin (450 mg, 0.25 mmol) from Example 1 was subjected to solid phase synthesis and purification by following procedure in Example 3 to yield 68 mg (12%) of white amorphous powder. (ES)+-LCMS m/e calcd for C106H156N34O22 2258.64 found 2258.61

Example 29

Preparation of Pentoyl-Ile-Lys-Pqa-Arg-His-Tyr-Leu-Asn-Trp-Val-Thr-Arg-Gln-(NMe)Arg-Tyr-NH$_2$ (SEQ ID NO: 27)

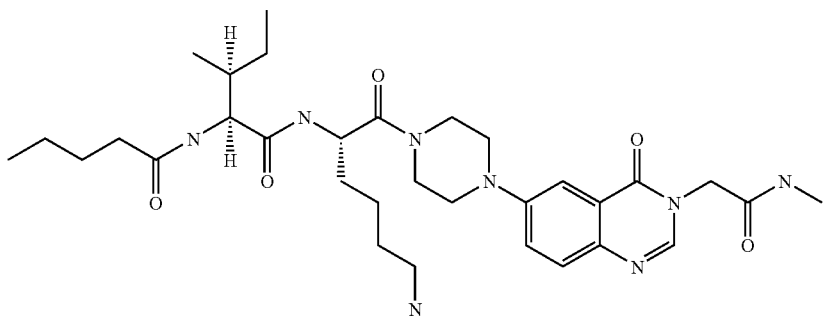

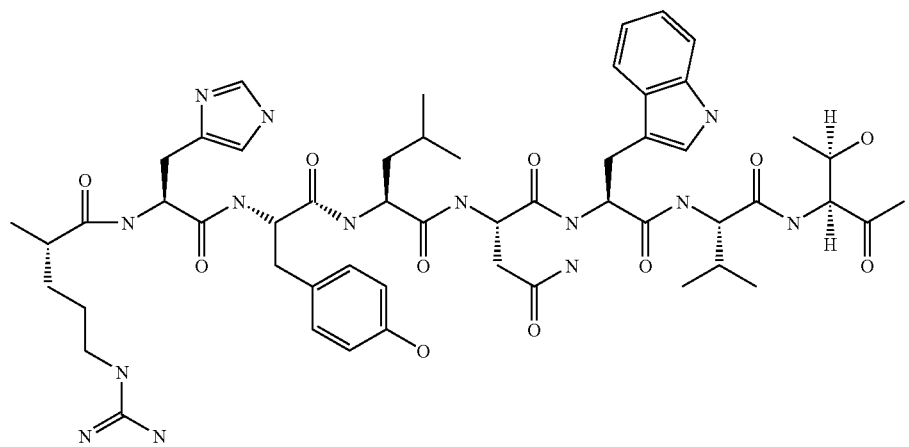
Fmoc-Linker-BHA resin (450 mg, 0.25 mmol) from Example 1 was subjected to solid phase synthesis and purification by following procedure in Example 3 to yield 67 mg (12%) of white amorphous powder. (ES)+-LCMS m/e calcd for C109H162N34O22 2300.72 found 2300.69.
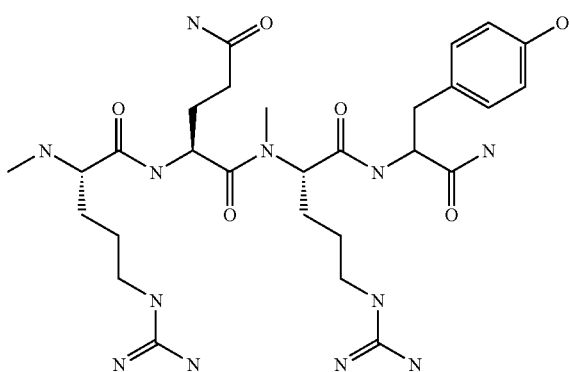
Example 30
Preparation of Trim ethylacetyl-Ile-Lys-Pqa-Arg-His-Tyr-Leu-Asn-Trp-Val-Thr-Arg-Gln-(NMe)Arg-Tyr-NH₂ (SEQ ID NO: 28)
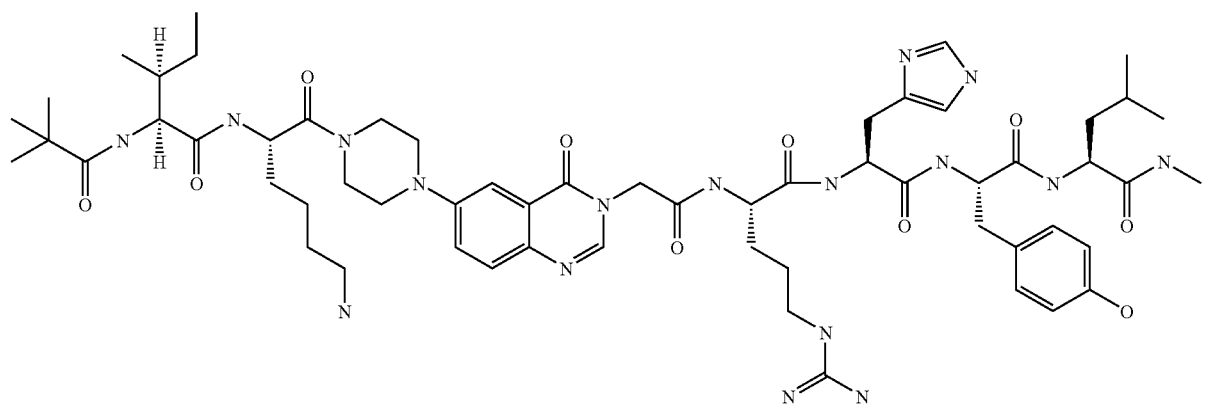

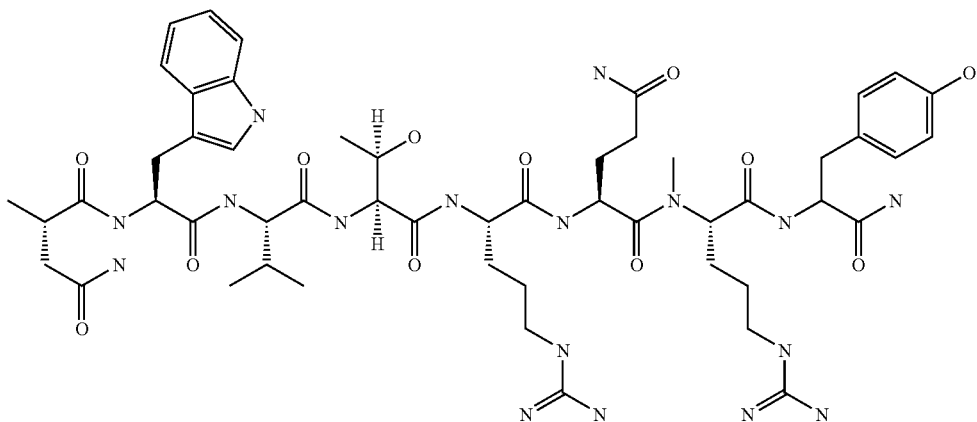
Fmoc-Linker-BHA resin (450 mg, 0.25 mmol) from Example 1 was subjected to solid phase synthesis and purification by following procedure in Example 3 to yield 6 mg (1%) of white amorphous powder. (ES)+-LCMS m/e calcd for C109H162F2N34O22 2300.72 found 2300.68.
Example 31
Preparation of Cyclohexylacetyl-Ile-Lys-Pqa-Arg-His-Tyr-Leu-Asn-Trp-Val-Thr-Arg-Gln-(NMe)Arg-Tyr-NH$_2$ (SEQ ID NO: 29)
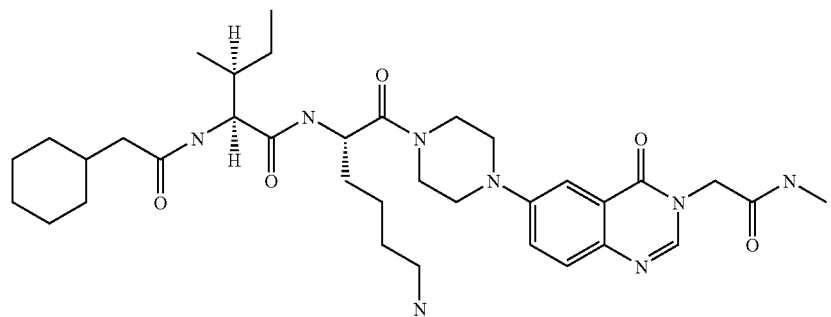
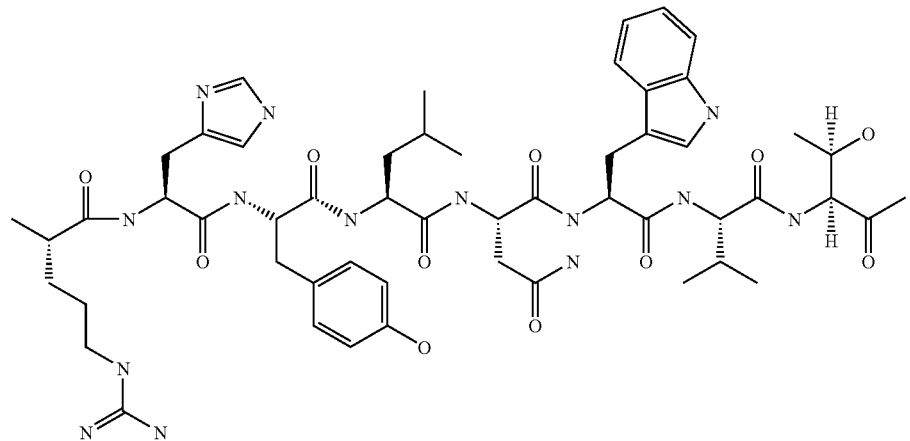

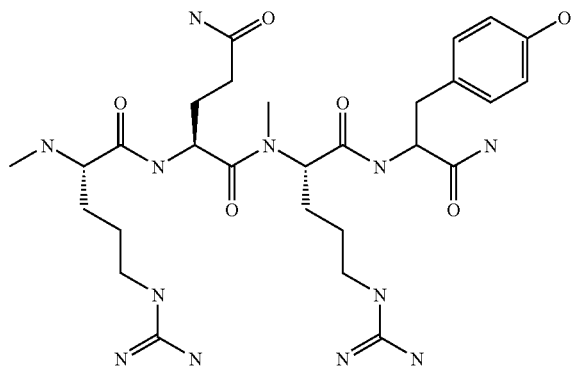
Fmoc-Linker-BHA resin (450 mg, 0.25 mmol) from Example 1 was subjected to solid phase synthesis and purification by following procedure in Example 3 to yield 15 mg (3%) of white amorphous powder. (ES)+-LCMS m/e calcd for C112H166N34O22 2340.79 found 2340.81.
Example 32
Preparation of Benzoyl-Ile-Lys-Pqa-Arg-His-Tyr-Leu-Asn-Trp-Val-Thr-Arg-Gln-(NMe)Arg-Tyr-NH$_2$
(SEQ ID NO: 30)
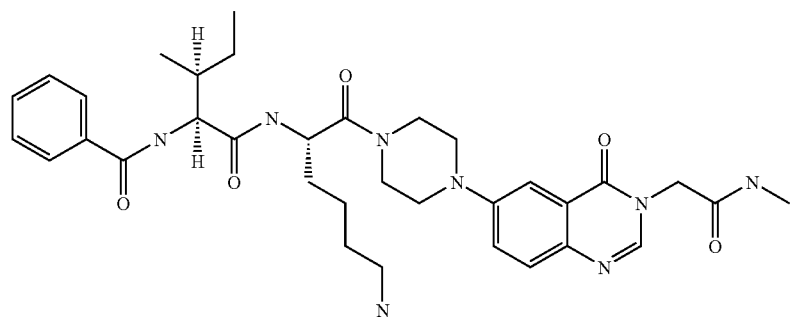
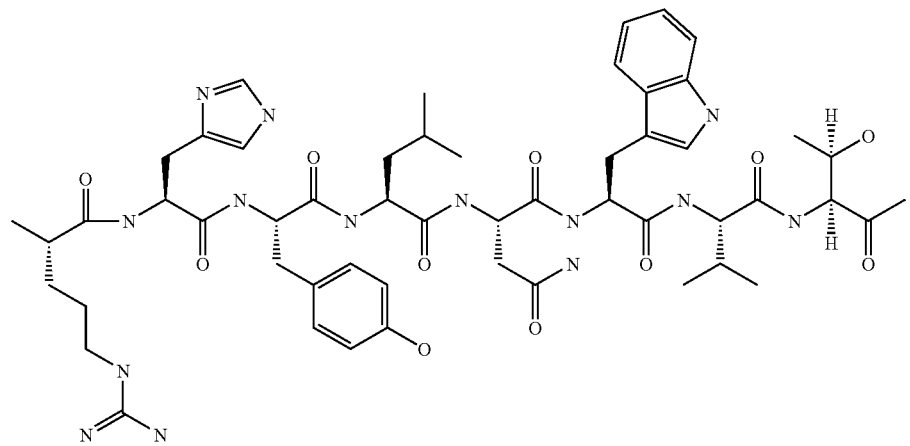

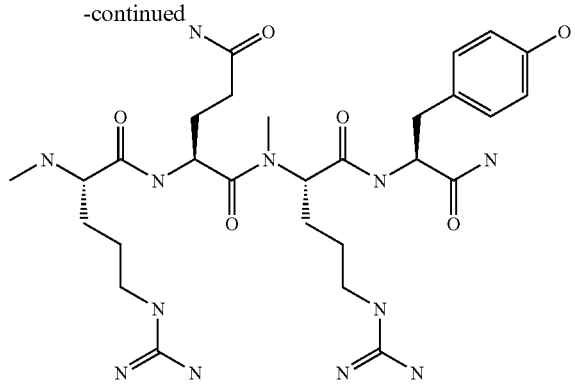
Fmoc-Linker-BHA resin (450 mg, 0.25 mmol) from Example 1 was subjected to solid phase synthesis and purification by following procedure in Example 3 to yield 23 mg (4%) of white amorphous powder. (ES)+-LCMS m/e calcd for C111H158N34O22 2320.71 found 2320.68.
Example 33
Preparation of Adamantoyl-Ile-Lys-Pqa-Arg-His-Tyr-Leu-Asn-Trp-Val-Thr-Arg-Gln-(NMe)Arg-Tyr-NH₂ (SEQ ID NO: 31)
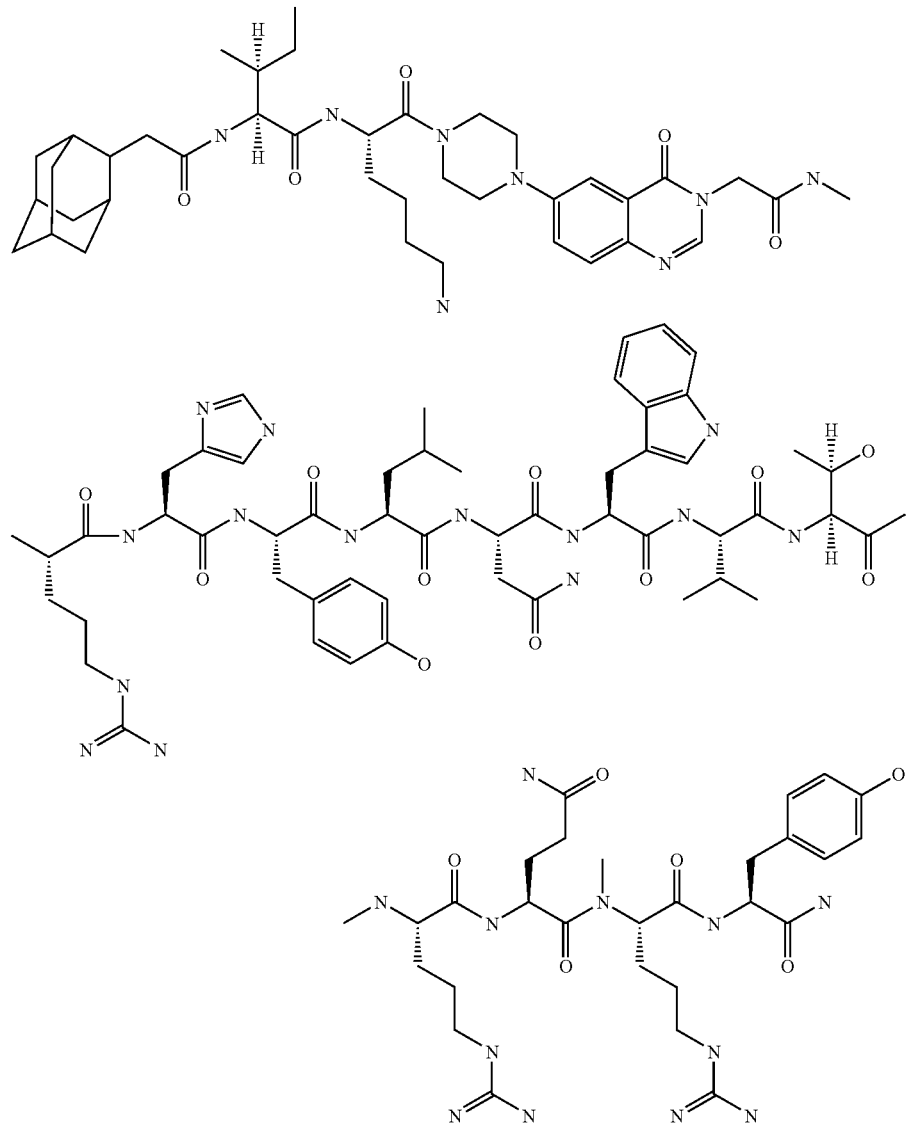

Fmoc-Linker-BHA resin (450 mg, 0.25 mmol) from Example 1 was subjected to solid phase synthesis and purification by following procedure in Example 3 to yield 29 mg (5%) of white amorphous powder. (ES)+-LCMS m/e calcd for $C_{116}H_{170}N_{34}O_{22}$ 2392.86 found 2392.89.

Analytical Method for Examples 34-39 and 41

The test and control articles were analyzed using the following reversed-phase HPLC/UV procedure:
Autosampler Alliance Waters 2690 Separation Module
Injection Volume 10 μL
Injector Temperature Ambient
Detector Waters 996 Photodiode Array Detector
Detector Wavelength 280 nm
Column Agilent Eclipse XDB-C8, 5 micron, 150 mm×4.6 mm i.d. PN:99367-906
Column Temperature 25° C.
Flow Rate 1.0 mL/minute (~1000 psi)
Mobile Phase A Water containing 0.05% TFA
Mobile Phase B Acetonitrile containing 0.05% TFA
Run Time Approximately 30 minutes
Sample Preparation Approximately 0.2-0.5 mg/ml
Diluent Deionized water
Mobile Phase Gradient Condition 1 (RP-HPLC1):

| Time, minutes | % Mobile Phase A | % Mobile Phase B | Condition |
|---|---|---|---|
| 0 | 95 | 5 | Linear ramp |
| 20 | 5 | 95 | |
| 26 | 95 | 5 | Equilibrium |

Mobile Phase Gradient Condition 2 (RP-HPLC2):

| Time, minutes | % Mobile Phase A | % Mobile Phase B | Condition |
|---|---|---|---|
| 0 | 85 | 15 | Linear ramp |
| 20 | 25 | 75 | |
| 26 | 85 | 15 | Equilibrium |

Example 34

Preparation of mixture of ((PEG-30,000)CH$_2$CH$_2$CO)Ile-Lys-Pqa-Arg-His-Tyr-Leu-Asn-Trp-Val-Thr-Arg-Gln-(NMe)Arg-Tyr-NH$_2$ (SEQ ID NO: 32) and De((PEG-30,000)CH$_2$CH$_2$CO)(ε)Lys-Pqa-Arg-His-Tyr-Leu-Asn-Trp-Val-Thr-Arg-Gln-(NMe)Arg-Tyr-NH$_2$ (SEQ ID NO: 33)

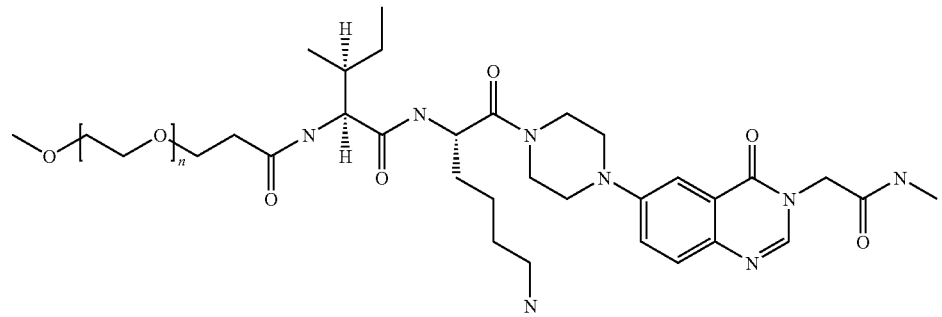

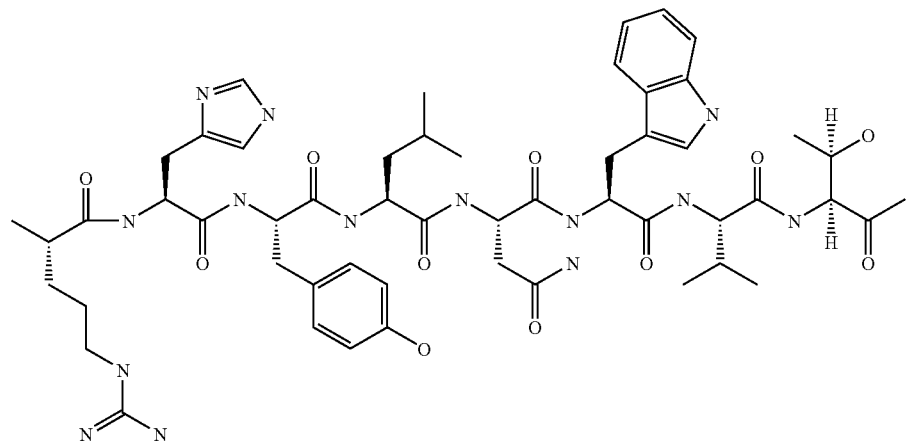

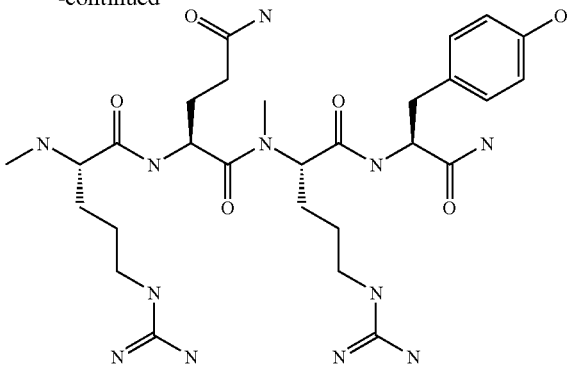

where n=~675
and

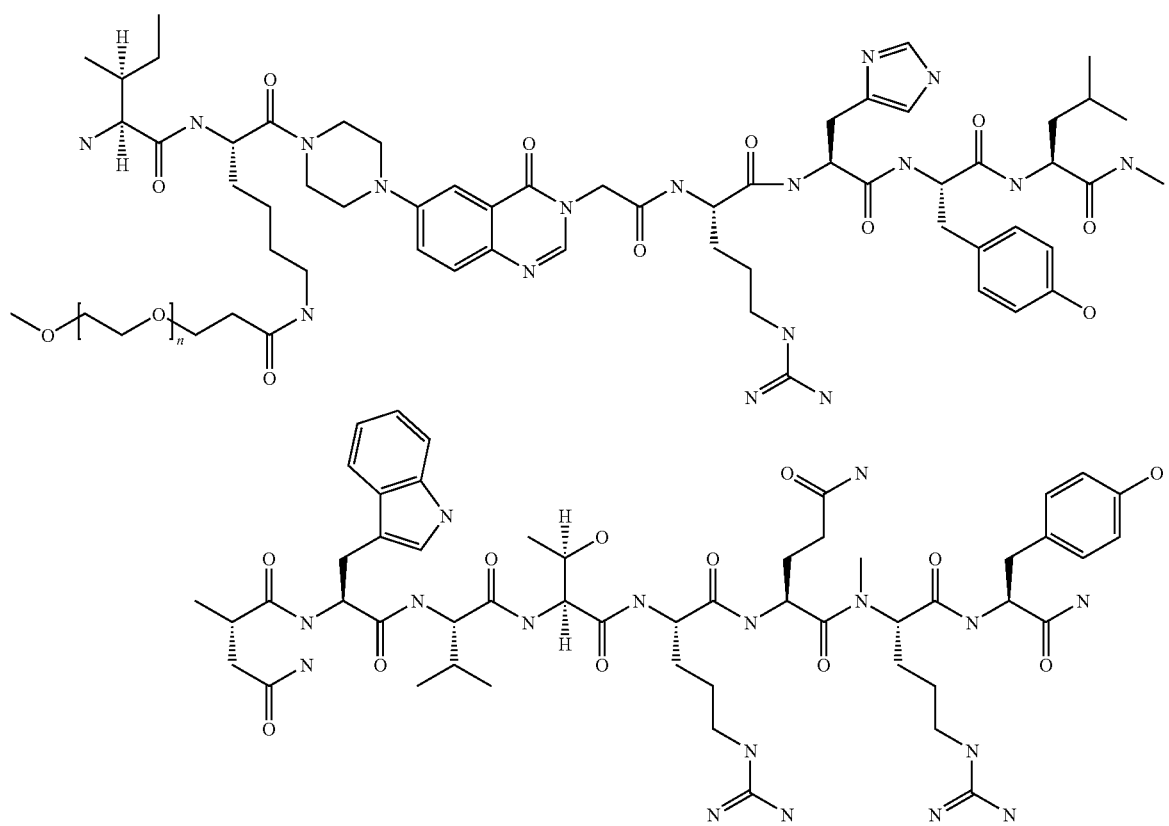

where n=~675

| Analytical Method | Result |
|---|---|
| RP-HPLC1 - rxn mixture | 69.8% conversion |
| RP-HPLC1 - purified | 10.1 min Retention time |
| MALDI-TOF MS | Average Mass = 33.9 kDa |

Twenty-five mg of peptide from Example 25 was weighed out and dissolved in 50 mM Borate, pH 7.5 buffer. 500 mg 30 kDa PEG-succinimidyl proprionic acid (purchased from Nektar) was weighed to achieve a 2:1 PEG:peptide molar ratio and added to the dissolved peptide. The reaction mixture was agitated at room temperature overnight before it was diluted 10-fold in 20 mM NaOAc, pH 4.5 buffer and purified by cation exchange chromatography on SP-Sepharose FF. FIG. 1 is an HPLC chromatogram of the reaction mixture. The reaction yielded 69.8% of 30 kDa peptide.

Mono-pegylated PYY peptide was eluted using a step NaCl gradient. Typically, the desired mono-pegylated peptide eluted with 250 mM NaCl. The eluted PEG-PYY-like peptide was concentrated in an Amicon ultrafiltration cell using a 10 kDa MW cutoff membrane. It was then diafiltered 10-fold once with PBS.

Figure 2:
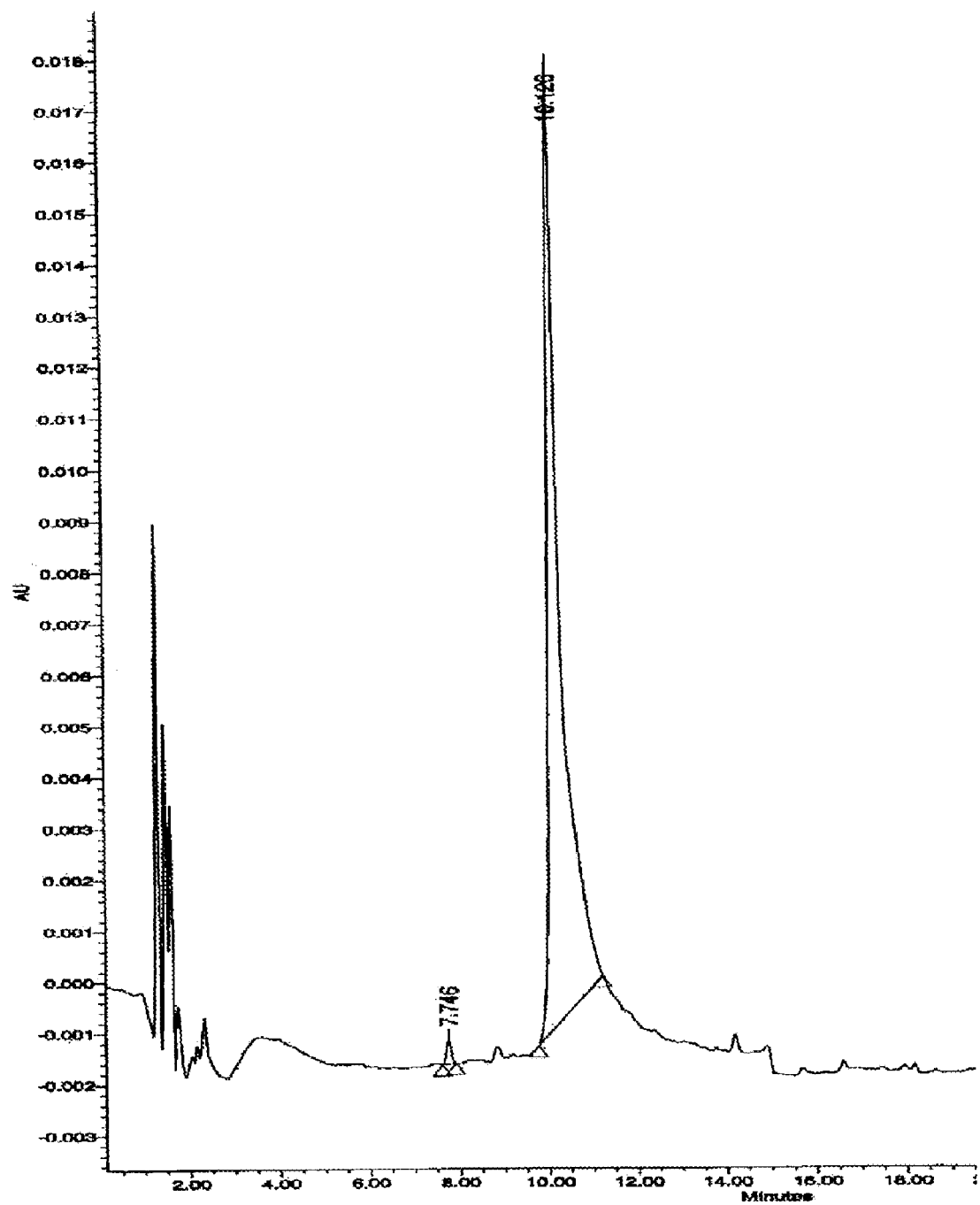
FIG. 2 shows an HPLC chromatogram of a purified compound (example 34) of the present invention.
Figure 3:
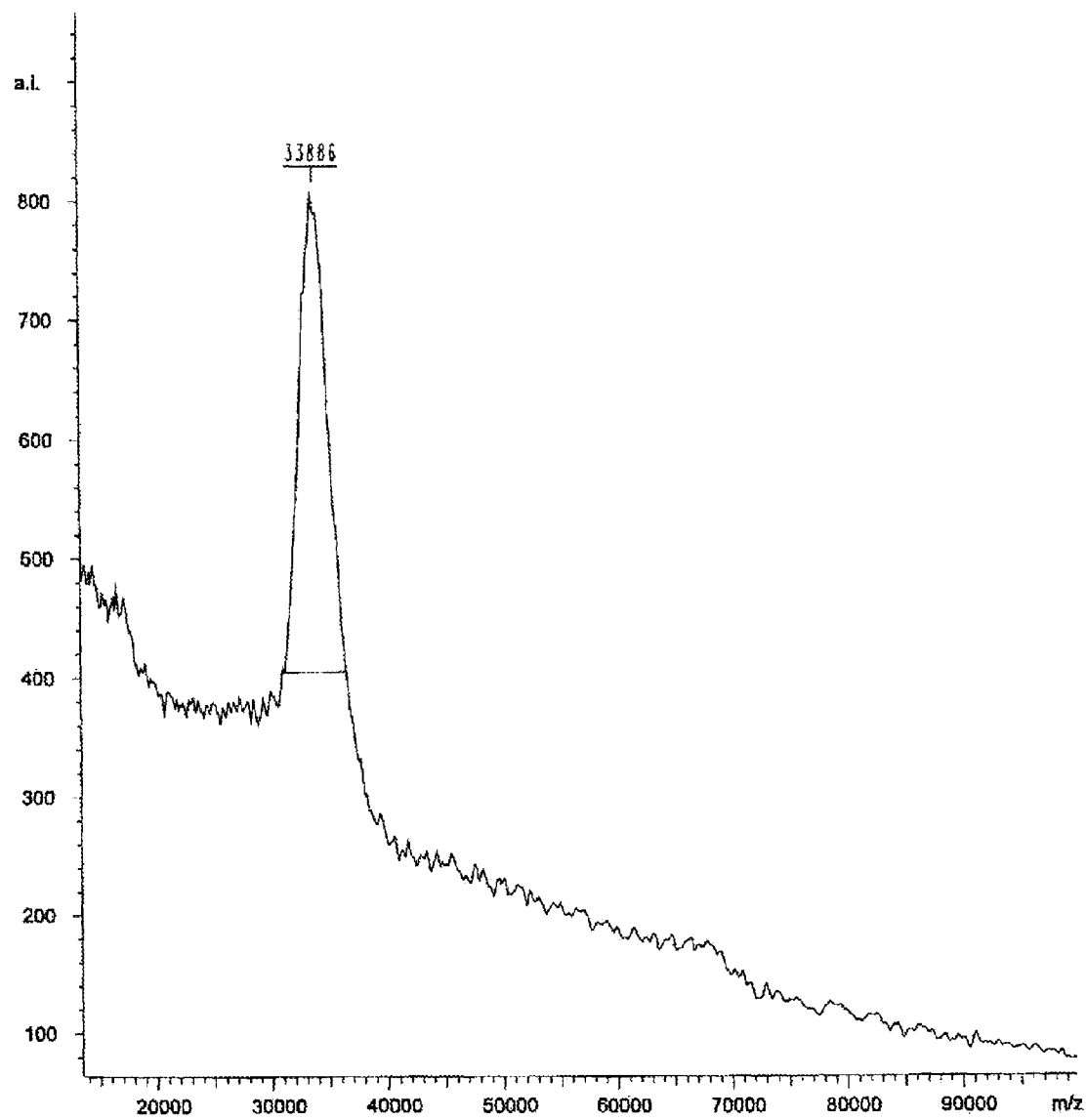
FIG. 3 shows a MALDI-TOF spectrum of a compound (example 34) of the present, invention.

Concentrated peptide of Example 34 was submitted for analysis, assayed and stored at −20 C. FIG. 2 is an HPLC chromatogram of purified 30 kDa PEG-PYY peptide (RT=10.1 min). Purity of 30 kDa peptide was determined to be >97%. And FIG. 3 is a graph representing a MALDI-TOF of 30 kDa PEG-PYY peptide, which was performed to confirm the molecular weight.

A combination of methods was used to determine the PEG modification sites. These included, MALDI TOF MS, reversed phase HPLC, proteolytic digestion and N-terminal sequencing (Edman). The results from these analyses showed that the majority of the PEG is attached through the ε-amino group of the lysine in position (R2) of the peptide.

Example 35

Preparation of a mixture of ((PEG-40,000)CO)Ile-Lys-Pqa-Arg-His-Tyr-Leu-Asn-Trp-Val-Thr-Arg-Gln-(NMe)Arg-Tyr-NH$_2$ (SEQ ID NO: 34) and Ile ((PEG-40,000)CO)(ε)Lys-Pqa-Arg-His-Tyr-Leu-Asn-Trp-Val-Thr-Arg-Gln-(NMe)Arg-Tyr-NH$_2$ (SEQ ID NO: 35)

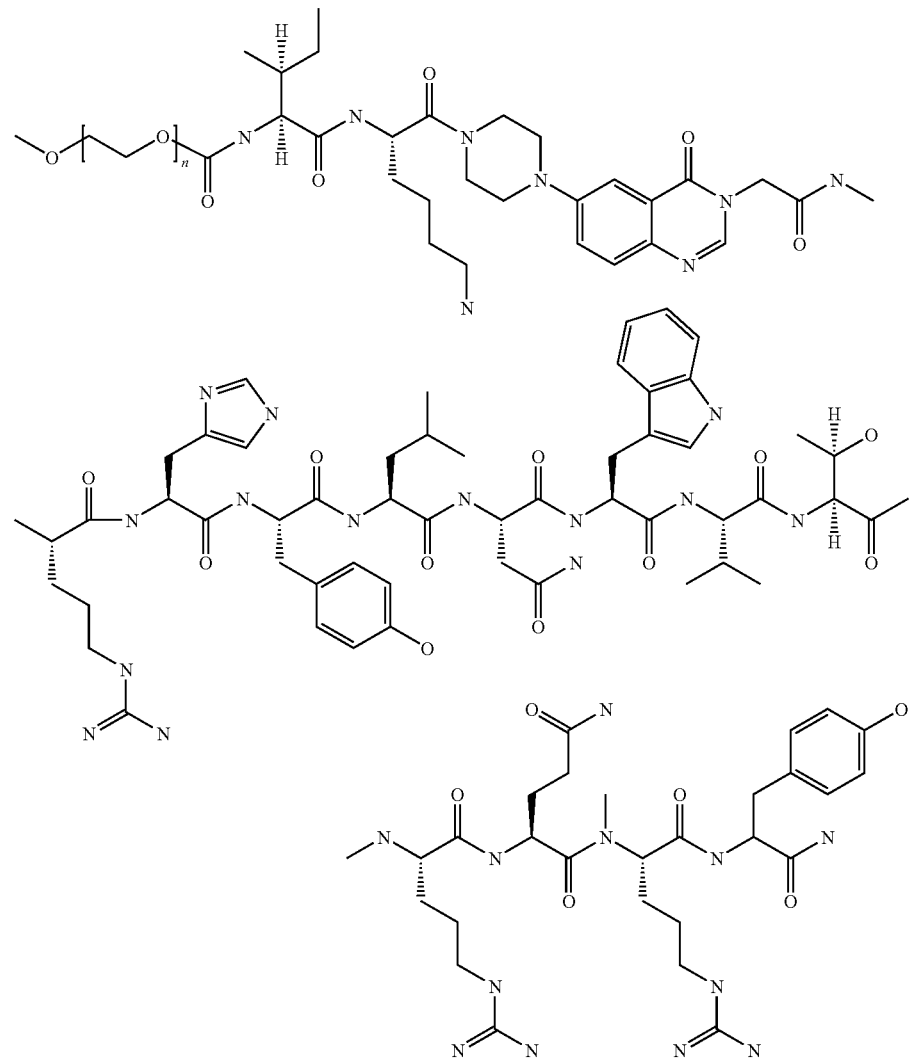

where n=~900
and

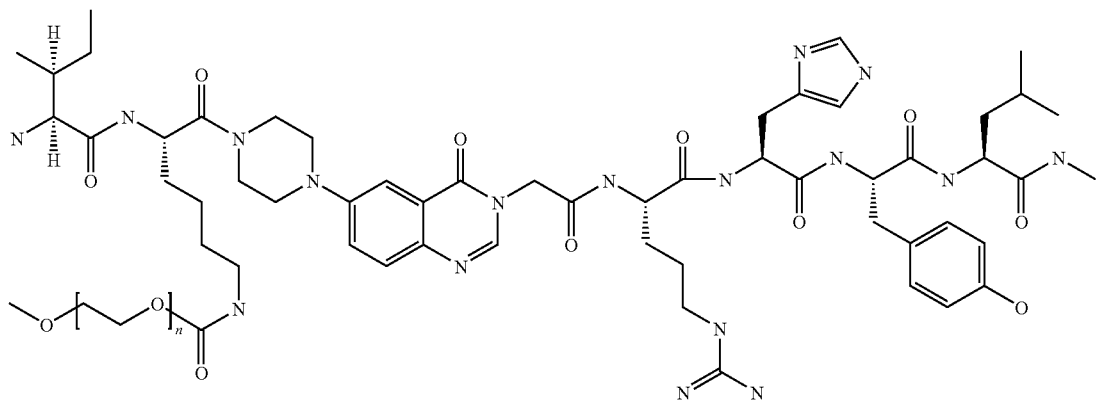

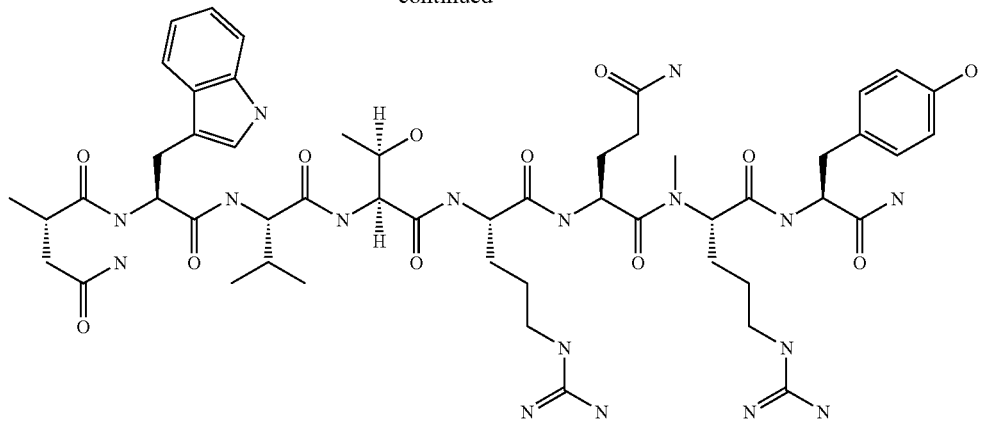

where n=~900

| Analytical Method | Result |
|---|---|
| RP-HPLC1 - rxn mixture | 60.4% conversion |
| RP-HPLC1 - purified | 10.1 min Retention time |
| MALDI-TOF MS | Average Mass = 41.9 kDa |

Figure 4:
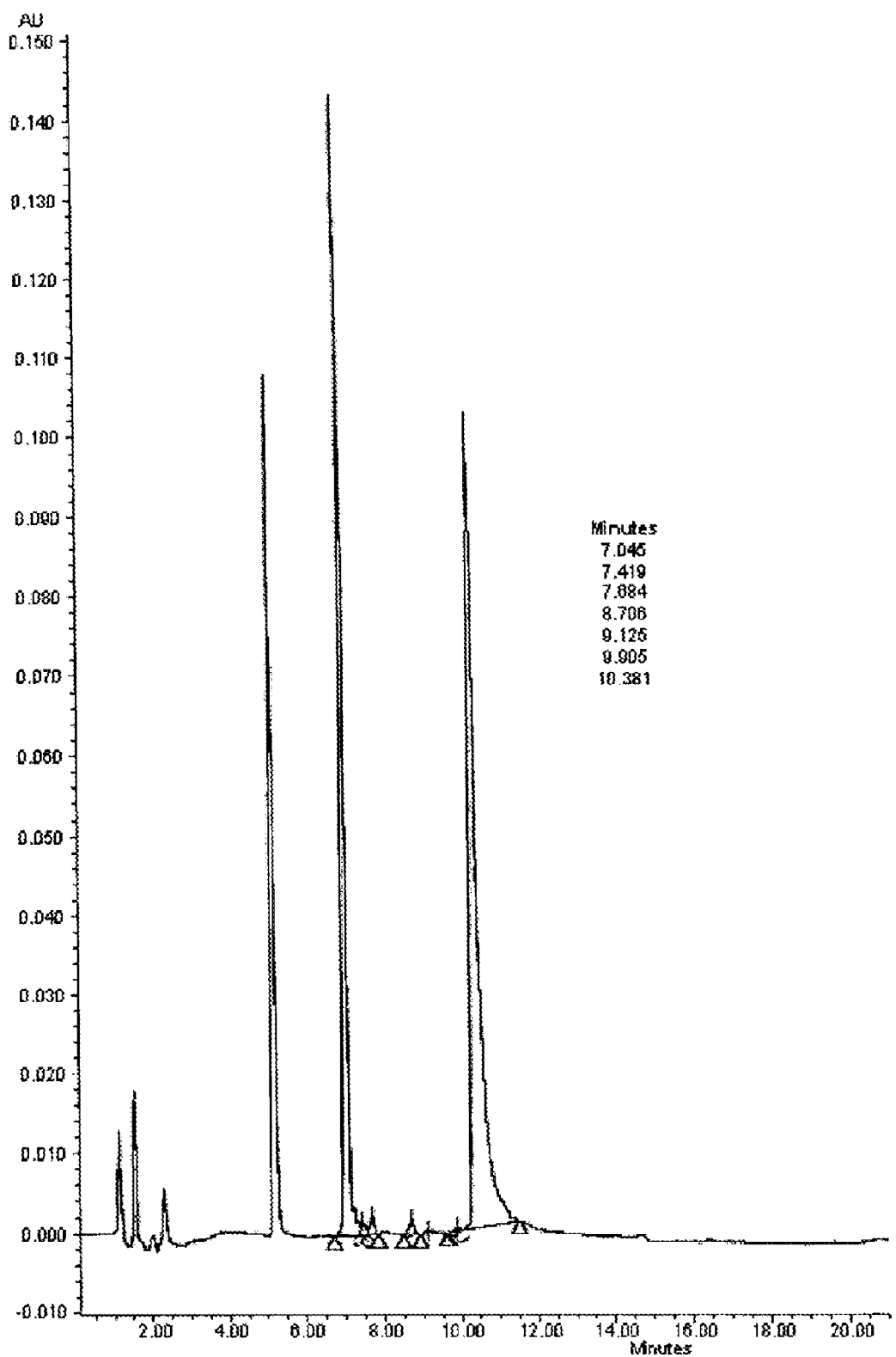
FIG. 4 shows an HPLC chromatogram of a reaction mixture of another compound (example 35) of the present invention.

Twenty-five mg of peptide from Example 25 was weighed out and dissolved in 50 mM Borate, pH 8.0 buffer. 319 mg 40 kDa PEG-benzotriazole carbonate was weighed to achieve a 0.8:1 PEG:peptide molar ratio and added to the dissolved peptide. The reaction mixture was agitated at room temperature for 1 h before it was diluted 10-fold in 20 mM NaOAc, pH 4.5 buffer and purified by cation exchange chromatography on SP-Sepharose FF. FIG. 4 is an HPLC chromatogram of the reaction mixture. The reaction yielded 60.4% of 40 kDa peptide.

Mono-pegylated PYY peptide was eluted using a step NaCl gradient. Typically, the desired mono-pegylated peptide eluted with 250 mM NaCl. The eluted PEG-PYY-like peptide was concentrated in an Amicon ultrafiltration cell using a 10 kDa MW cutoff membrane. It was then diafiltered 10-fold once with PBS.

Figure 5:
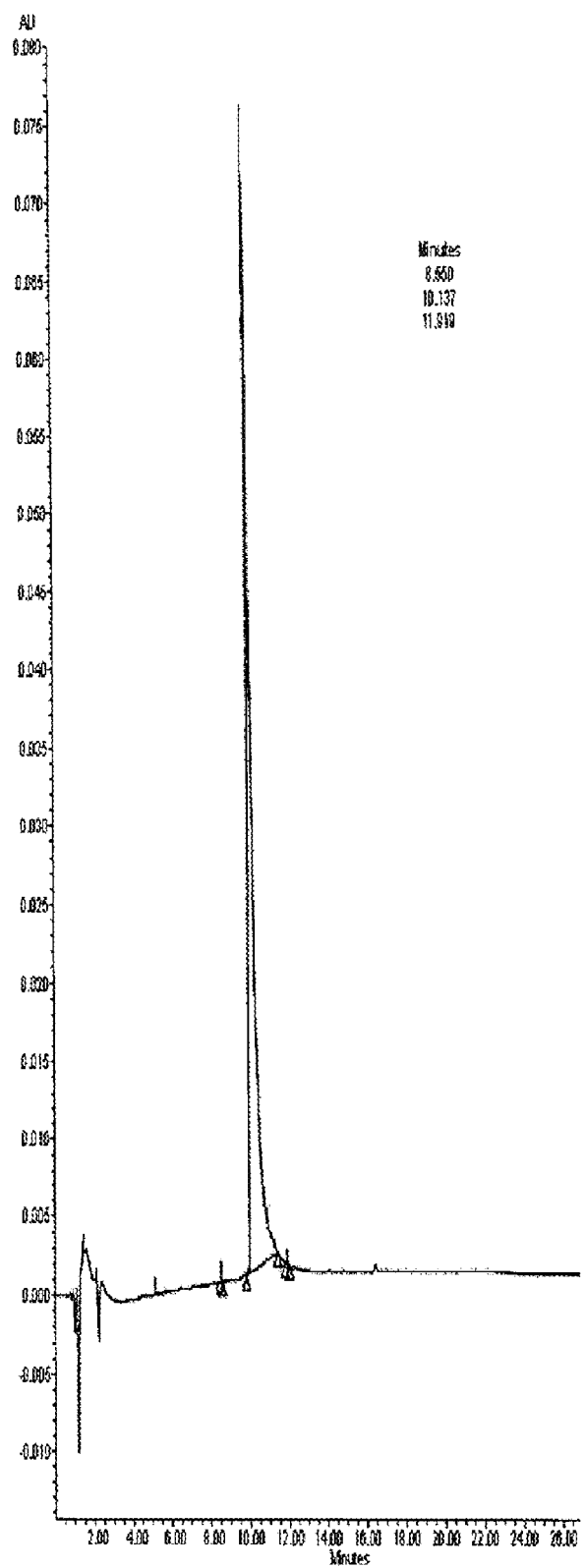
FIG. 5 shows an HPLC chromatogram of a purified a compound (example 35) of the present invention.
Figure 6:
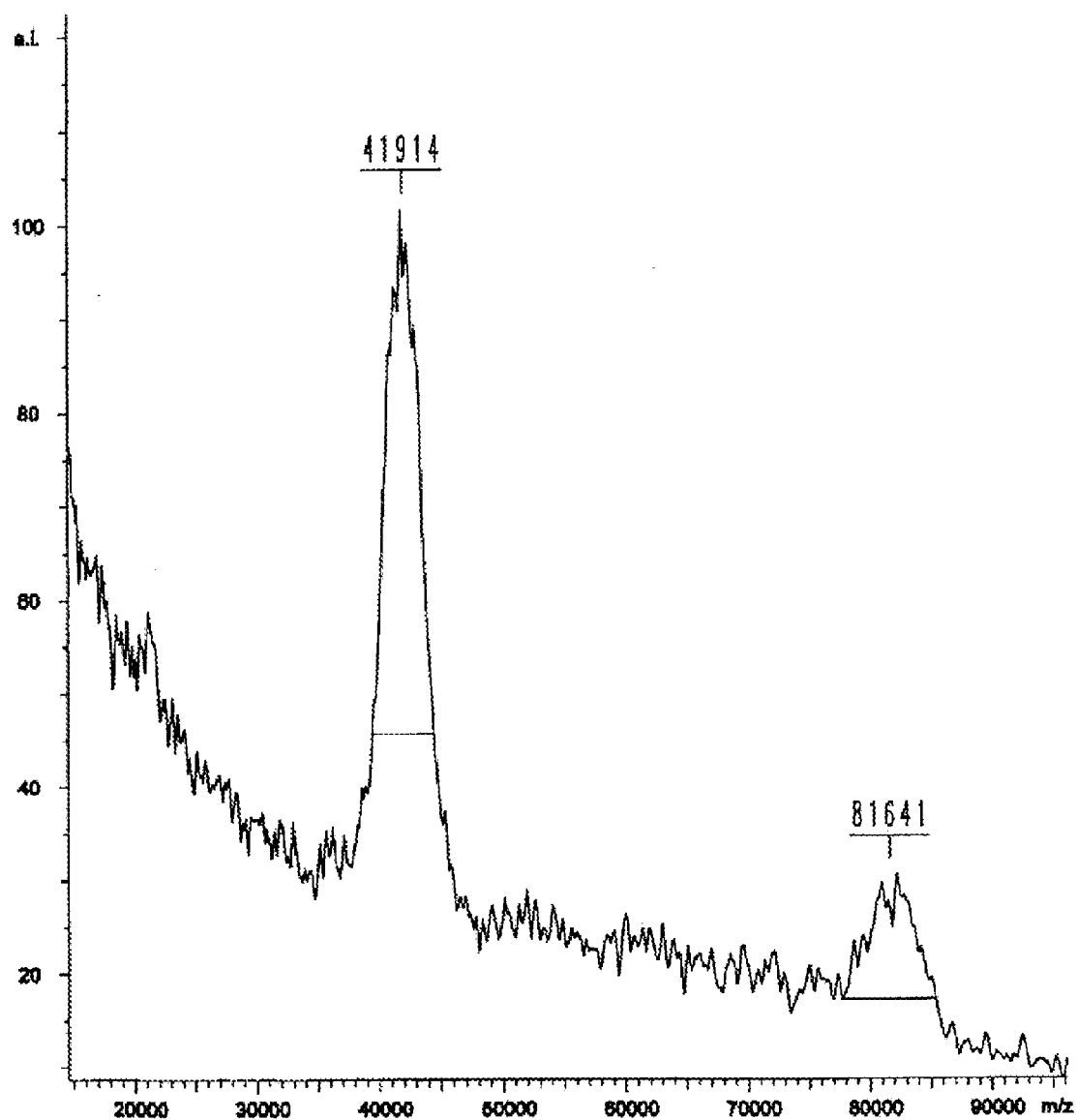
FIG. 6 shows a MALDI-TOF spectrum of a compound (example 35) of the present invention.

Concentrated peptide of Example 35 was submitted for analysis, assayed and stored at −20 C. FIG. 5 is an HPLC chromatogram of purified 40 kDa PEG-PYY peptide (RT=10.1 min). Purity of 40 kDa peptide was determined to be >90%. And FIG. 6 is a graph representing a MALDI-TOF of 40 kDa PEG-PYY peptide, which was performed to confirm the molecular weight.

Example 36

Preparation of ((PEG-30,000)CH$_2$CH$_2$NHCOCH$_2$CH$_2$CO)Ile-Nle-Pqa-Arg-His-Tyr-Leu-Asn-Trp-Val-Thr-Arg-Gln-(NMe)Arg-Tyr-NH$_2$ (SEQ ID NO: 36)

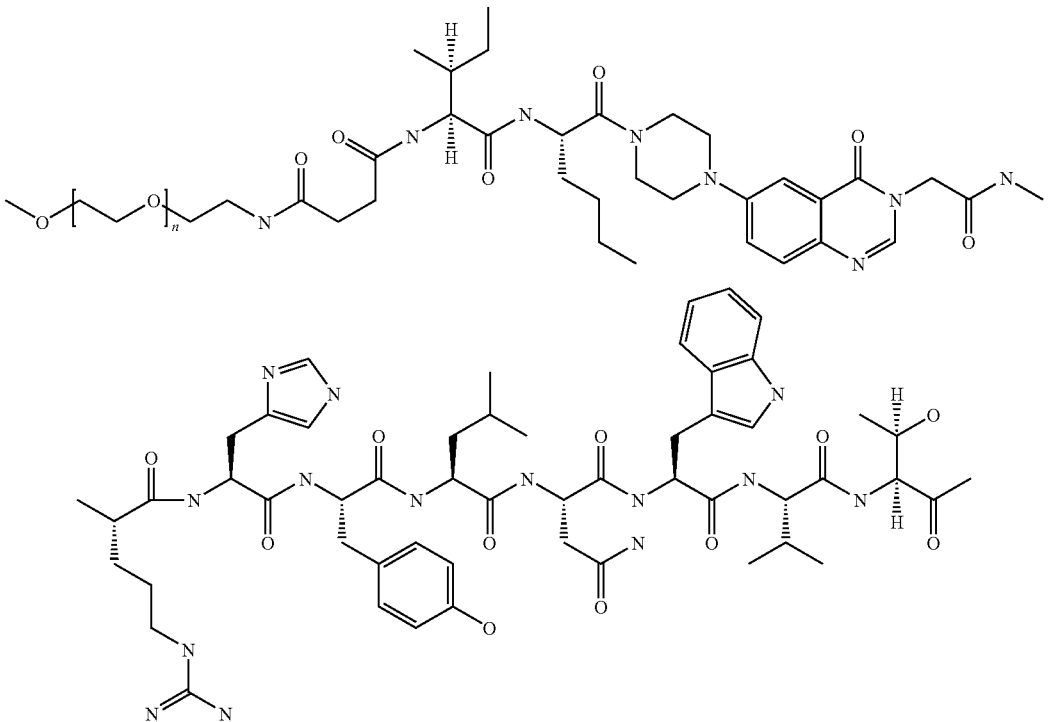

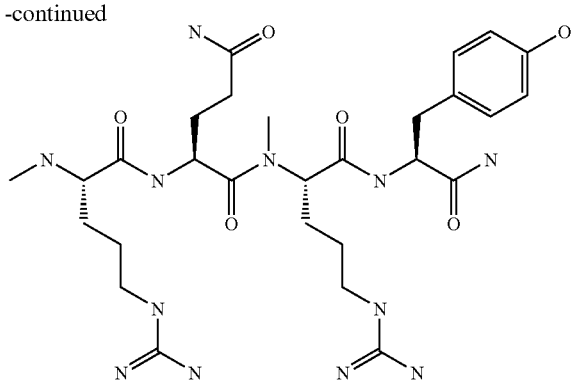

where n=~675

| Analytical Method | Result |
| --- | --- |
| RP-HPLC1 - rxn mixture | 94.1% conversion |
| RP-HPLC1 - purified | 10.4 min Retention time |
| MALDI-TOF MS | Average Mass = 34.2 kDa |

Figure 7:
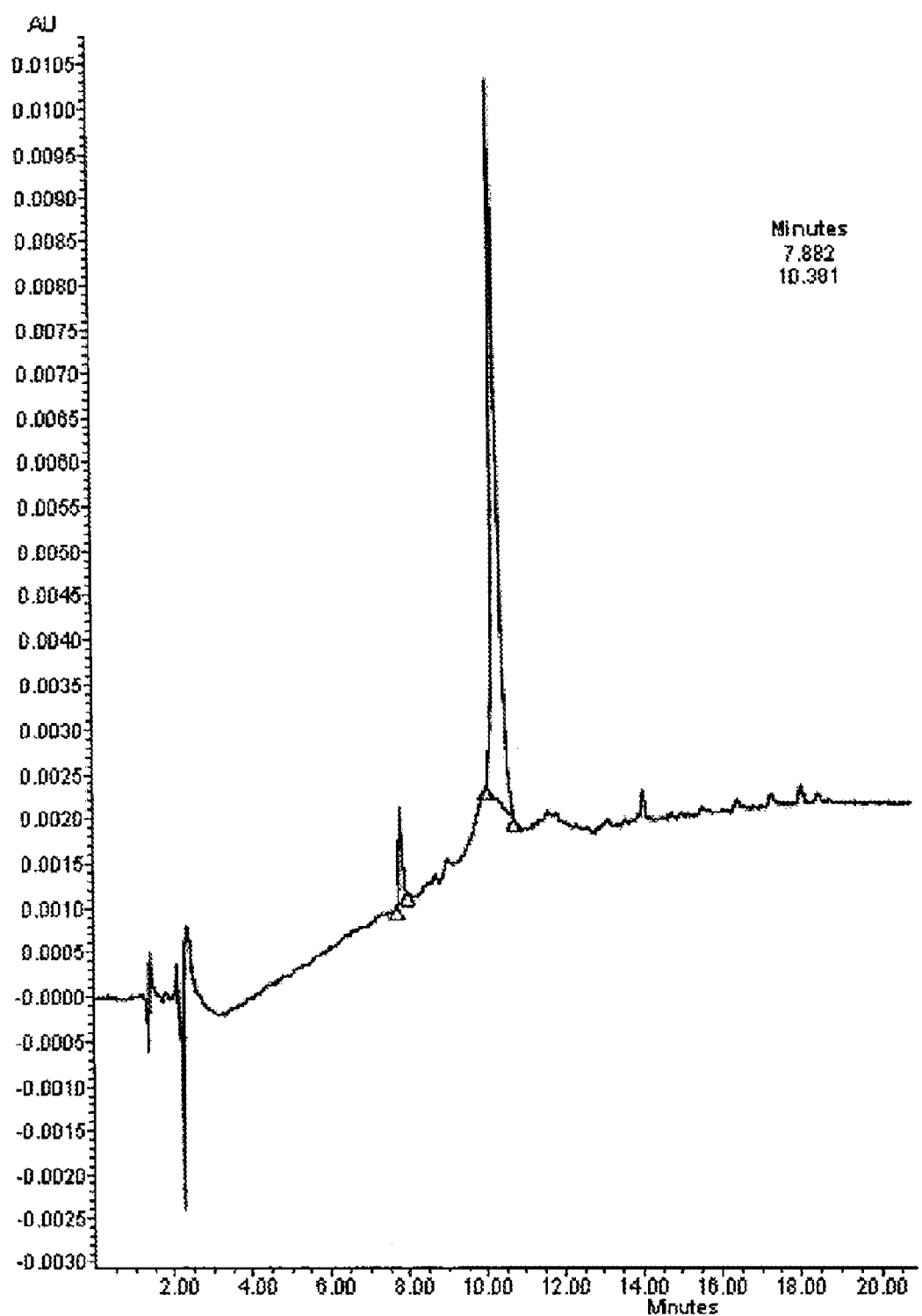
FIG. 7 shows an HPLC chromatogram of a reaction mixture of a compound (example 36) of the present invention.

Thirteen mg of peptide from Example 26 was weighed out and dissolved in 50 mM Borate, pH 8.0 buffer. 624 mg 30 kDa PEG-succinimidyl succinamide was weighed to achieve a 4:1 PEG:peptide molar ratio and added to the dissolved peptide. The reaction mixture was agitated at room temperature for 2 h before it was diluted 10-fold in 20 mM NaOAc, pH 4.5 buffer and purified by cation exchange chromatography on SP-Sepharose FF (Amersham). FIG. 7 is an HPLC chromatogram of the reaction mixture. The reaction yielded 94.1% of 30 kDa peptide.

Figure 8:
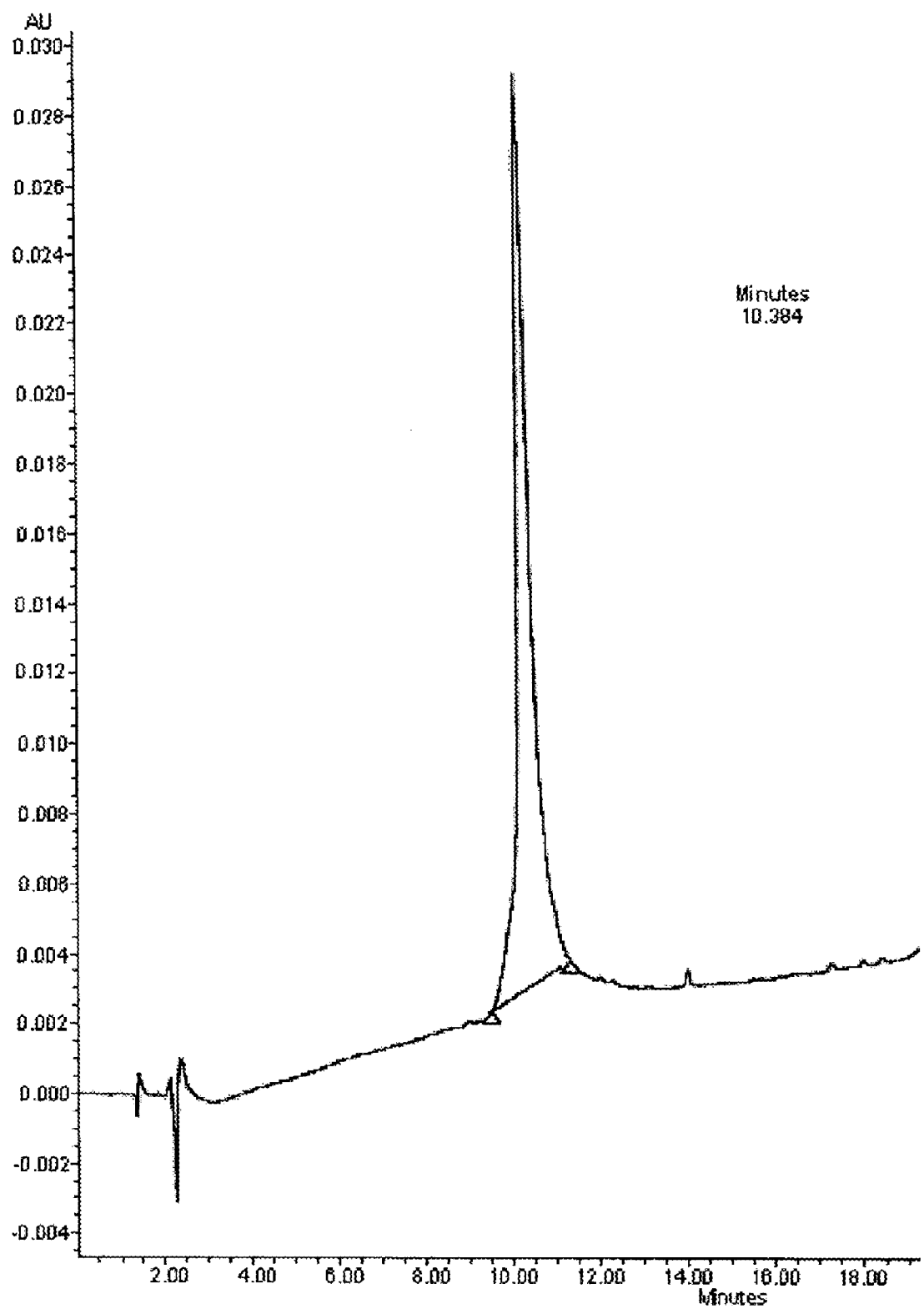
FIG. 8 shows an HPLC chromatogram of a purified compound (example 36) of the present invention.
Figure 9:
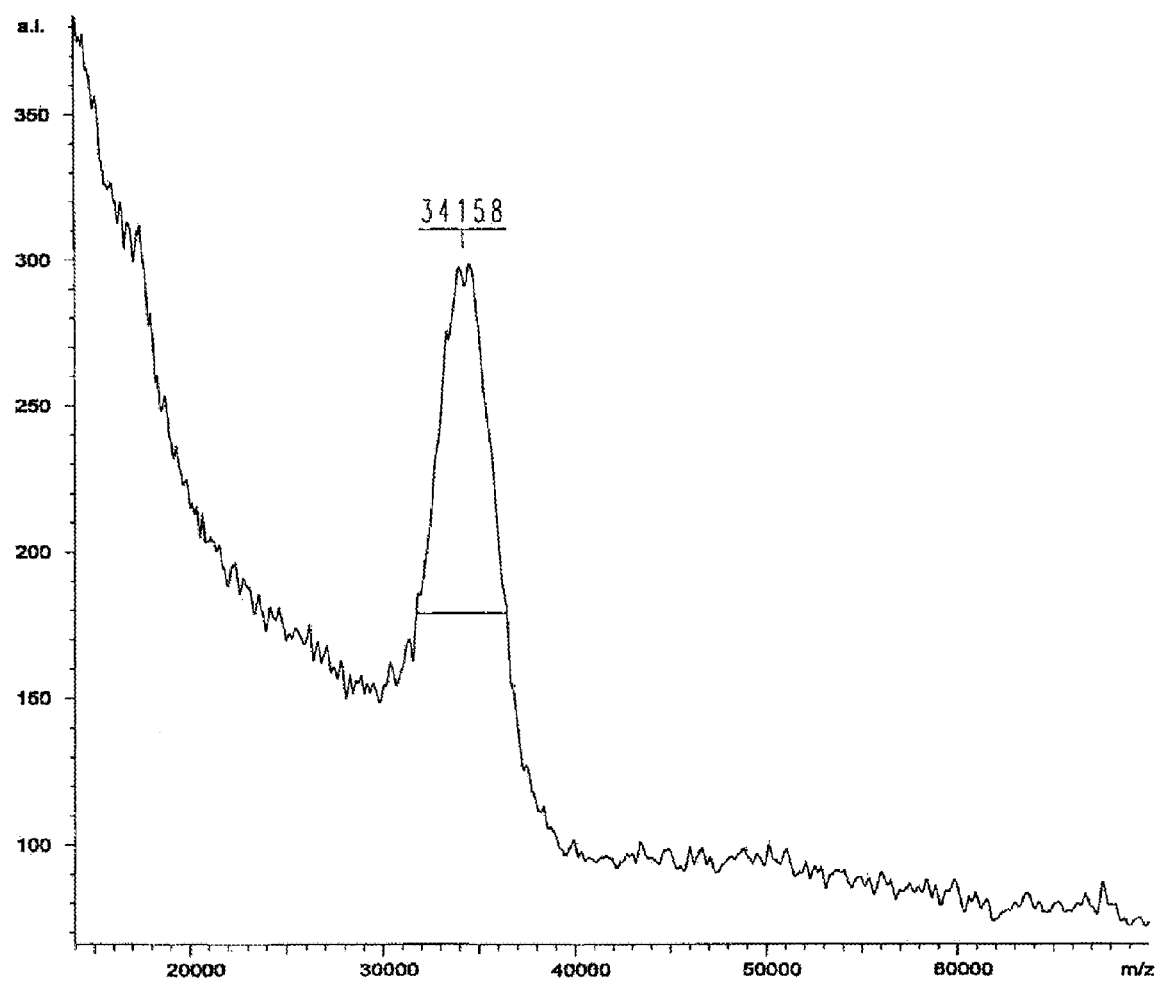
FIG. 9 shows a MALDI-TOF spectrum of yet another compound (example 36) of the present invention.

Mono-pegylated PYY peptide was eluted using a step NaCl gradient. Typically, the desired mono-pegylated PYY peptide eluted with 250 mM NaCl. The eluted PEG-PYY-like peptide was concentrated in an Amicon ultrafiltration cell using a 10 kDa MW cutoff membrane. It was then diafiltered 10-fold once with PBS. Concentrated peptide was submitted for analysis, assayed and stored at −20 C. FIG. 8 is an HPLC chromatogram of purified 30 kDa PEG-PYY peptide (10.4 min). Purity of 30 kDa peptide was determined to be >90%. And FIG. 9 represents a MALDI-TOF of 30 kDa PEG-PYY peptide that was performed to confirm the molecular weight.

Example 37

Preparation of ((PEG-30,000)CH(CH$_3$)CH$_2$CO)Ile-Nle-Pqa-Arg-His-Tyr-Leu-Asn-Trp-Val-Thr-Arg-Gln-(NMe)Arg-Tyr-NH$_2$ (SEQ ID NO: 37)

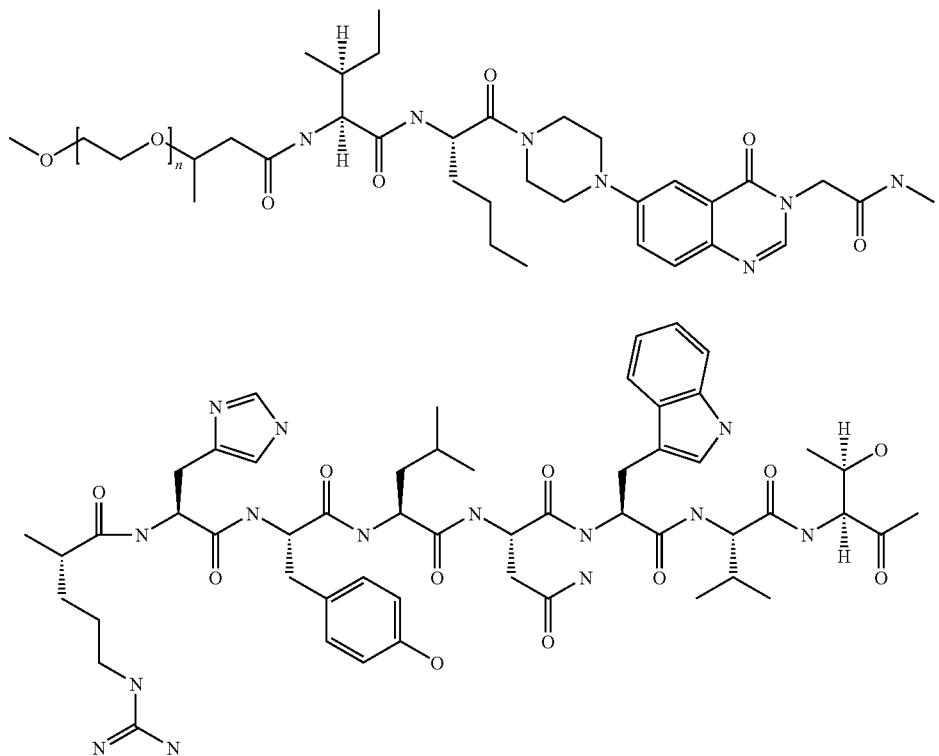

-continued

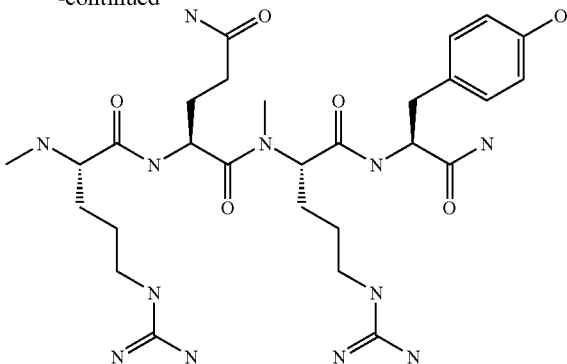

where n=~675

| Analytical Method | Result |
|---|---|
| RP-HPLC1 - rxn mixture | 93.4% conversion |
| RP-HPLC1 - purified | 10.5 min Retention time |
| MALDI-TOF MS | Average Mass = 34.6 kDa |

Figure 10:
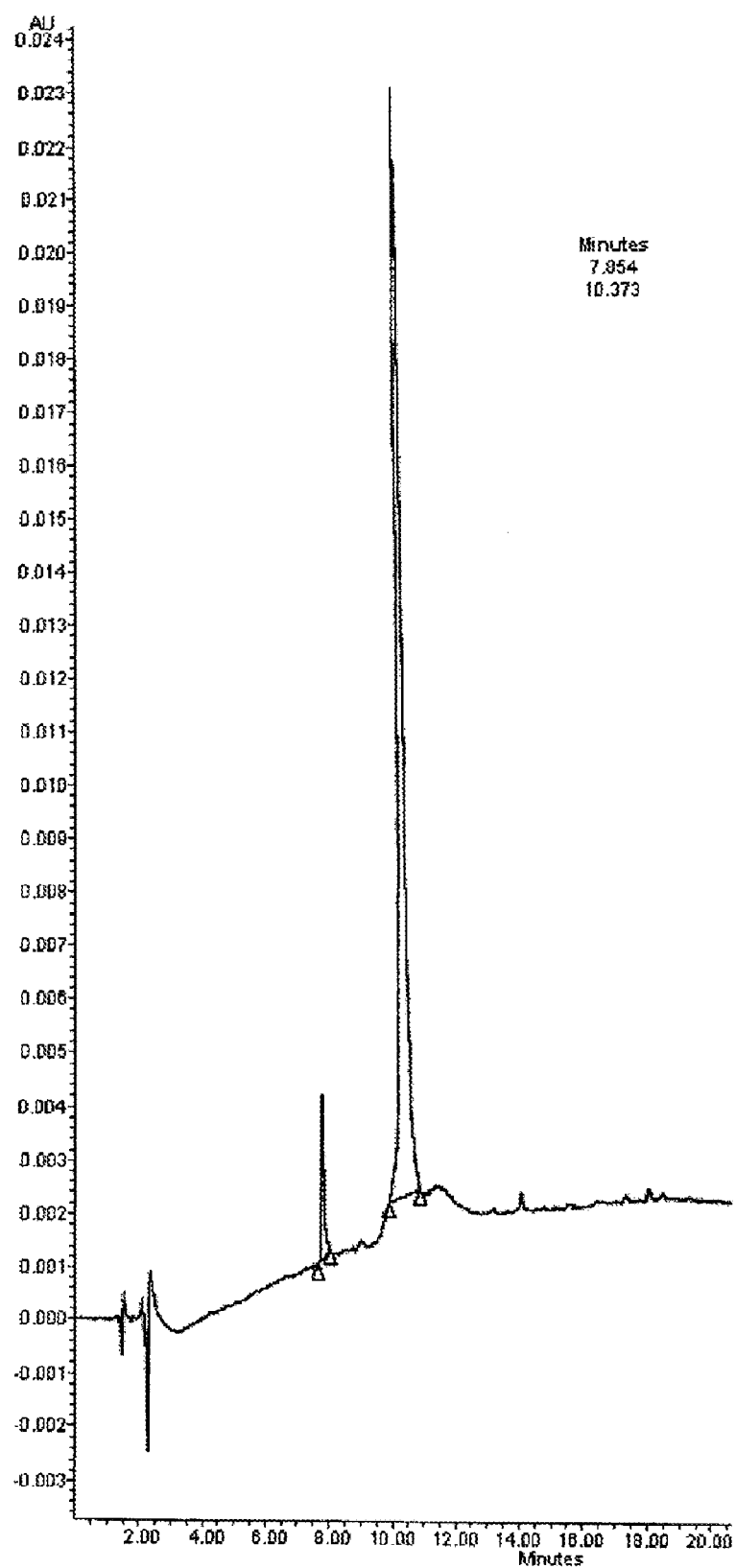
FIG. 10 shows an HPLC chromatogram of a reaction mixture of a compound (example 37) of the present invention.

1.25 mg of peptide from Example 26 was weighed out and dissolved in 50 mM Borate, pH 8.0 buffer. 62 mg 30 kDa PEG-succinimidyl beta-SBA was weighed to achieve a 4:1 PEG: peptide molar ratio and added to the dissolved peptide. The reaction mixture was agitated at room temperature for 2 h before it was diluted 10-fold in 20 mM NaOAc, pH 4.5 buffer and purified by cation exchange chromatography on SP-Sepharose FF (Amersham). FIG. 10 is an HPLC chromatogram of the reaction mixture. The reaction yielded 93.4% of 30 kDa peptide.

Figure 11:
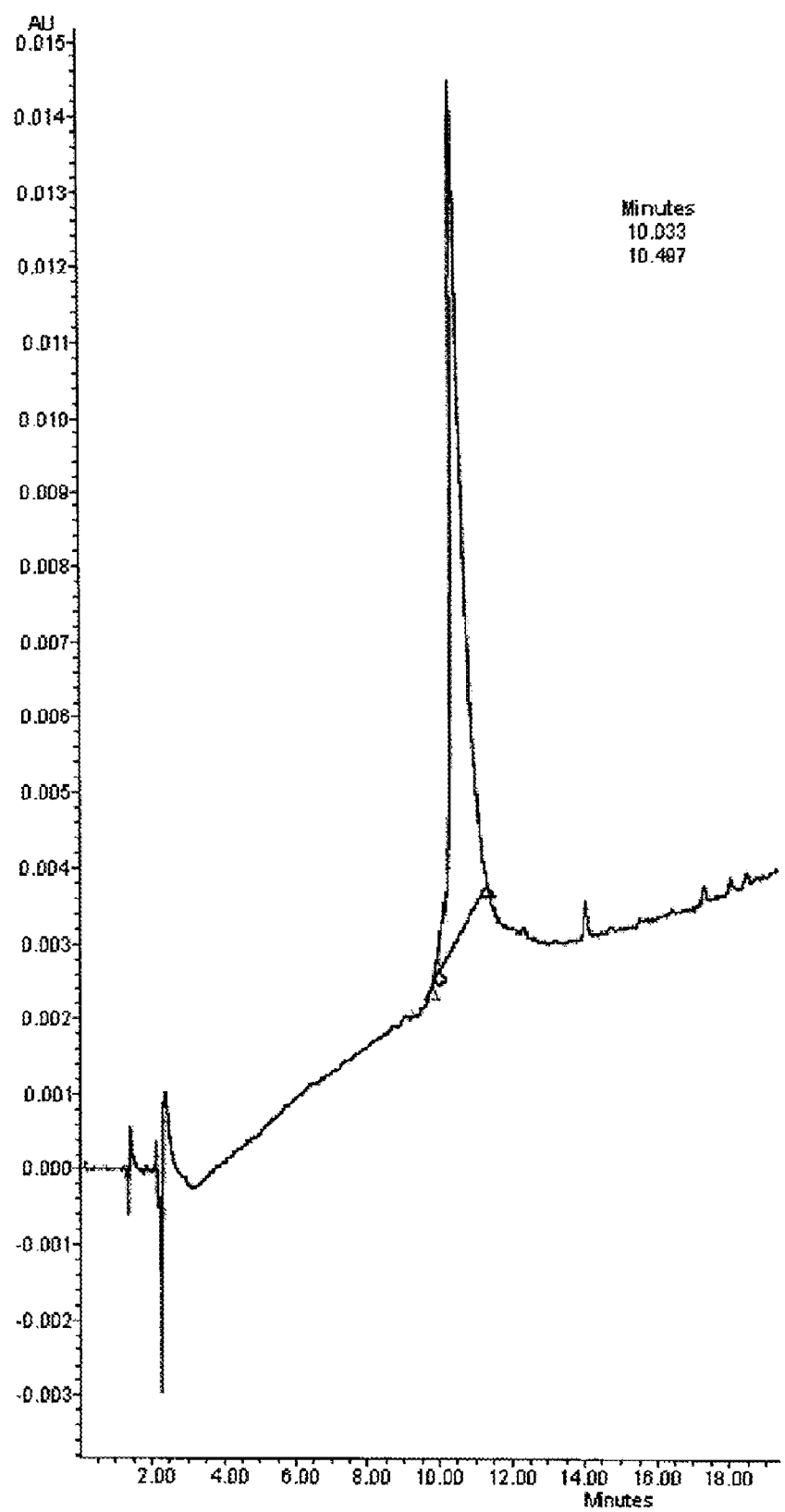
FIG. 11 shows an HPLC chromatogram of a purified compound (example 37) of the present invention.
Figure 12:
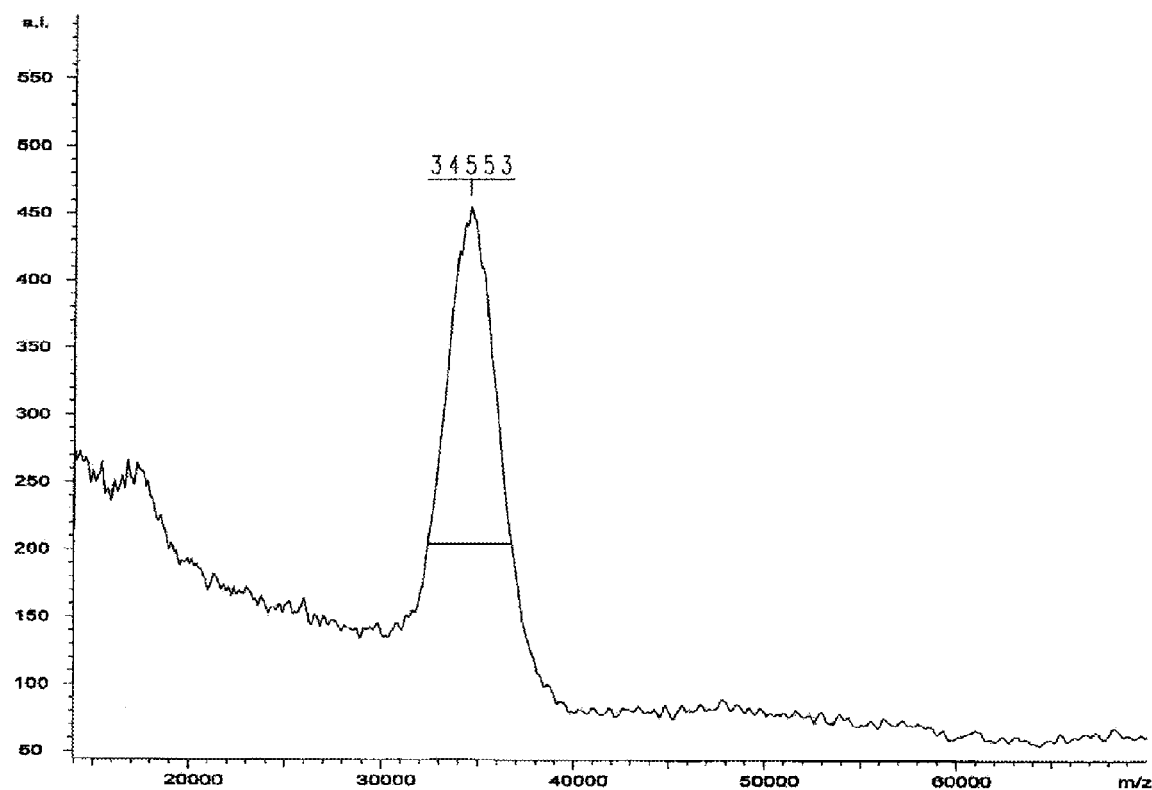
FIG. 12 shows a MALDI-TOF spectrum of a compound (example 37) of the present invention.

Mono-pegylated PYY peptide was eluted using a step NaCl gradient. Typically, the desired mono-pegylated PYY peptide eluted with 250 mM NaCl. The eluted PEG-PYY-like peptide was concentrated in an Amicon ultrafiltration cell using a 10 kDa MW cutoff membrane. It was then diafiltered 10-fold once with PBS. Concentrated peptide was submitted for analysis, assayed and stored at −20 C. FIG. 11 is an HPLC chromatogram of purified 30 kDa PEG-PYY peptide (10.5 min). Purity of 30 kDa peptide was determined to be >90%. And FIG. 12 represents a MALDI-TOF of 30 kDa PEG-PYY peptide that was performed to confirm the molecular weight.

Example 38

Preparation of Ac-Ile(PEG-30,000)CH$_2$CH$_2$CO($\epsilon$)Lys-Pqa-Arg-His-Tyr-Leu-Asn-Trp-Val-Thr-Arg-Gln-(NMe)Arg-Tyr-NH$_2$ (SEQ ID NO: 38)

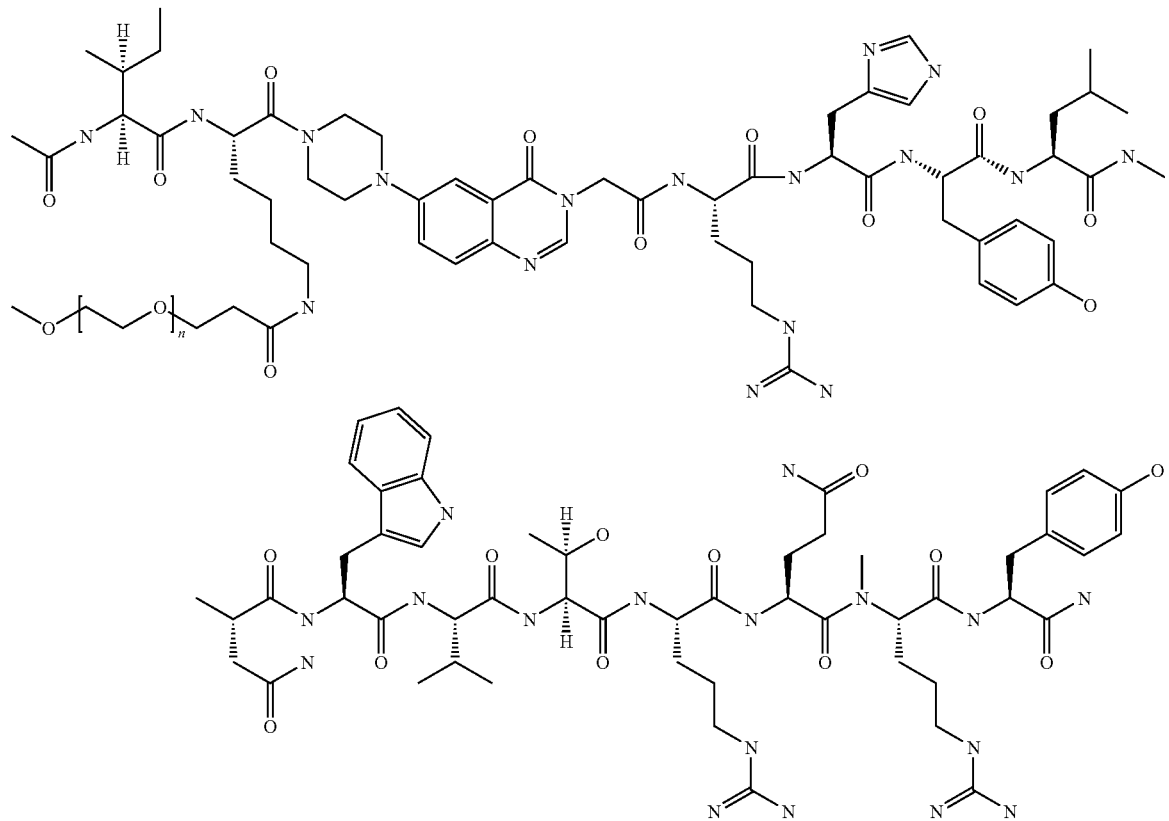

where n=~675

| Analytical Method | Result |
|---|---|
| RP-HPLC1 - rxn mixture | 83.3% conversion |
| RP-HPLC1 - purified | 9.5 min Retention time |
| MALDI-TOF MS | Average Mass = 34.6 kDa |

Figure 13:
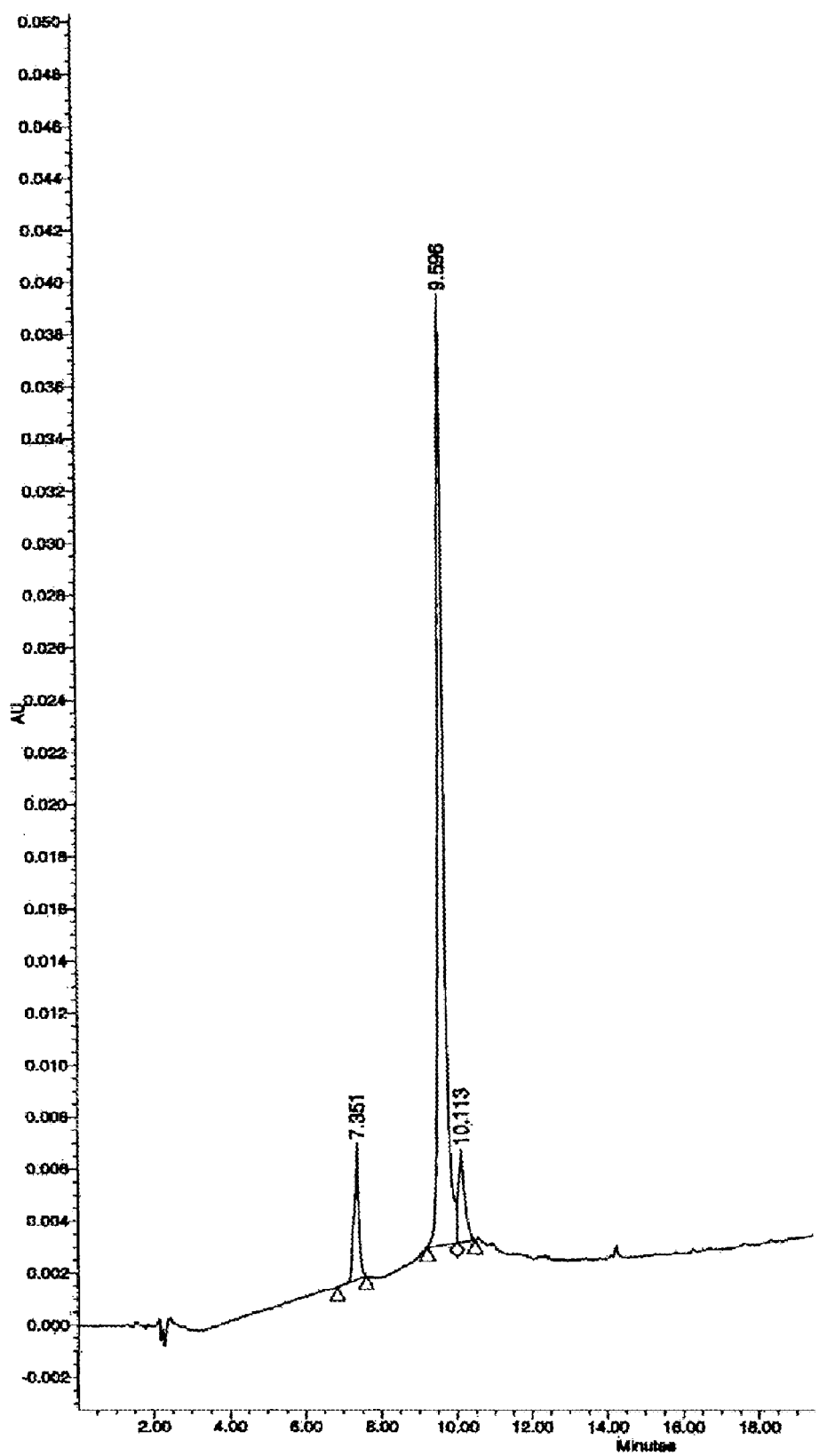
FIG. 13 shows an HPLC chromatogram of a reaction mixture of another compound (example 38) of the present invention.

One hundred mg of peptide from Example 28 was weighed out and dissolved in 50 mM Borate, pH 8.0 buffer. 1.8 g 30 kDa PEG-succinimidyl proprionic acid (purchased from Nektar) was weighed to achieve a 1.5:1 PEG:peptide molar ratio and added to the dissolved peptide. The reaction mixture was agitated at room temperature overnight before it was diluted 10-fold in 20 mM NaOAc, pH 4.5 buffer and purified by cation exchange chromatography on SP-Sepharose FF. FIG. 13 is an HPLC chromatogram of the reaction mixture. The reaction yielded 83.3% of 30 kDa peptide.

Mono-pegylated PYY peptide was eluted using a step NaCl gradient. Typically, the desired mono-pegylated peptide eluted with 250 mM NaCl. The eluted PEG-PYY-like peptide was concentrated in an Amicon ultrafiltration cell using a 10 kDa MW cutoff membrane. It was then diafiltered 10-fold once with PBS.

Figure 14:
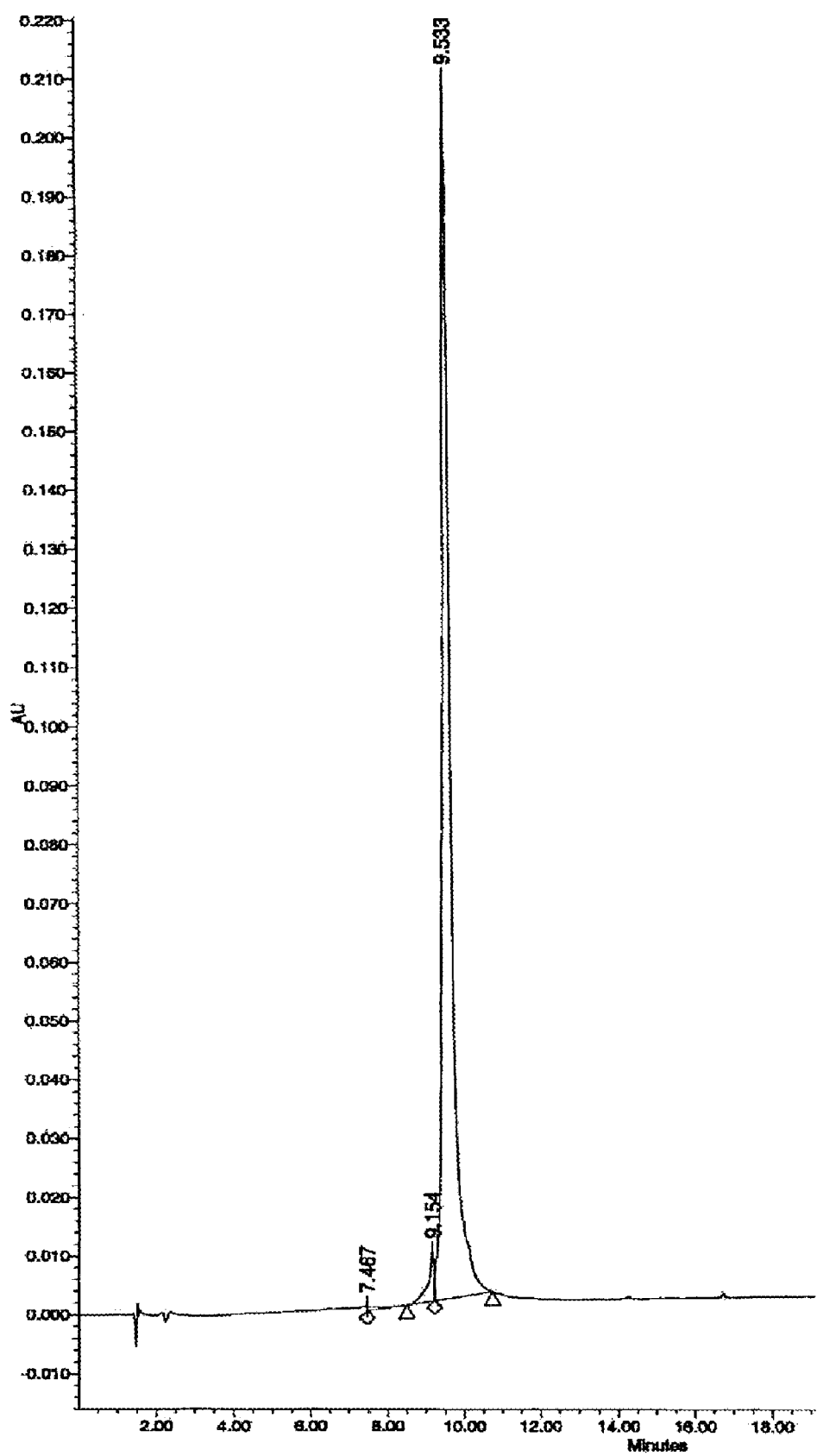
FIG. 14 shows HPLC chromatogram of a purified compound (example 38) of the present invention.
Figure 15:
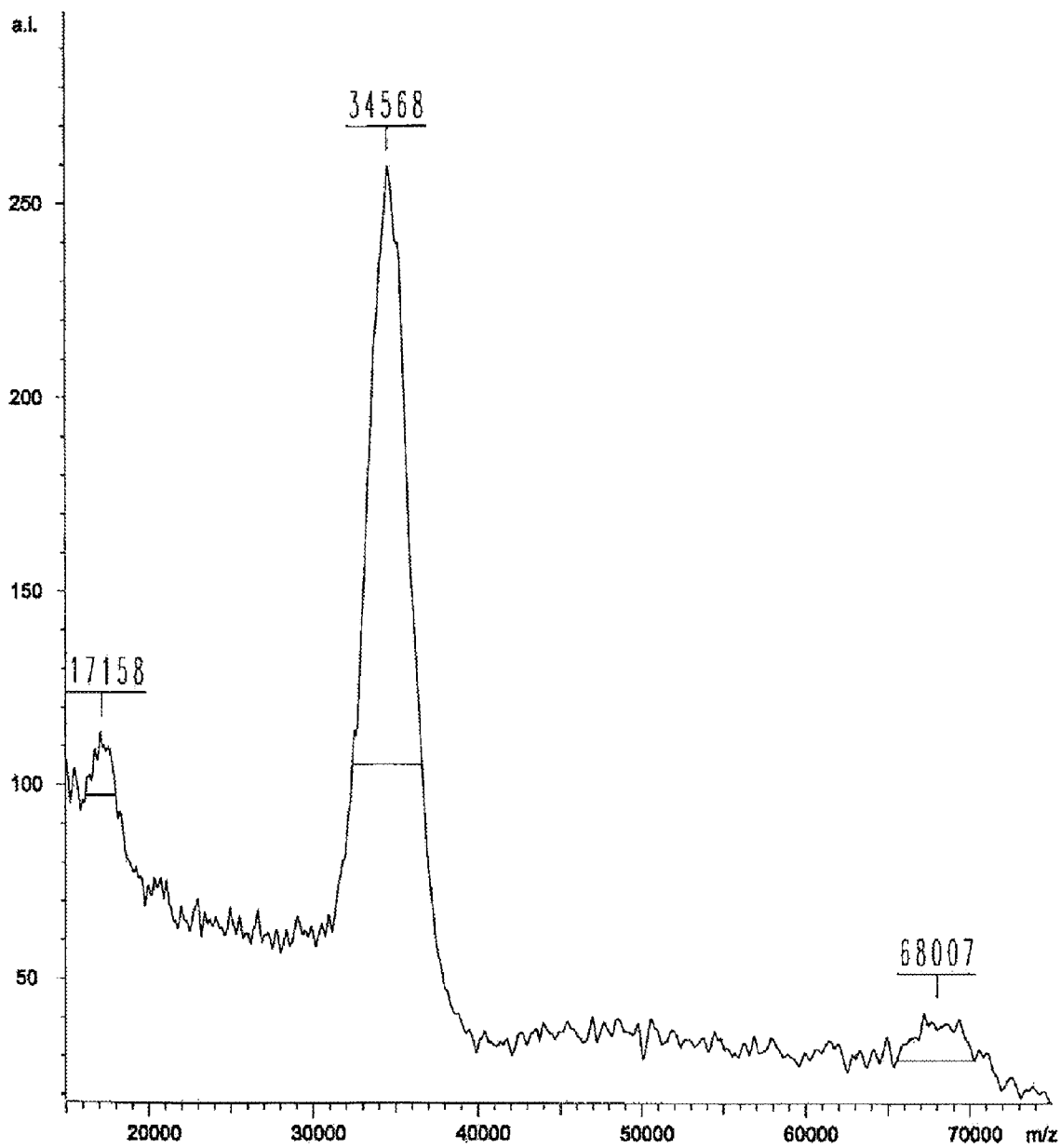
FIG. 15 shows a MALDI-TOF spectrum of a compound (example 38) of the present invention.

Concentrated peptide of Example 38 was submitted for analysis, assayed and stored at −20 C. FIG. 14 is an HPLC chromatogram of purified 30 kDa PEG-PYY peptide (RT=9.5 min). Purity of 30 kDa peptide was determined to be >95%. And FIG. 15 is a graph representing a MALDI-TOF of 30 kDa PEG-PYY peptide, which was performed to confirm the molecular weight.

Example 39

Preparation of Ac-Ile((PEG-30,000) CH$_2$CH$_2$NHCOCH$_2$CH$_2$CO)(ε)Lys-Pqa-Arg-His-Tyr-Leu-Asn-Trp-Val-Thr-Arg-Gln-(NMe)Arg-Tyr-NH$_2$ (SEQ ID NO: 39)

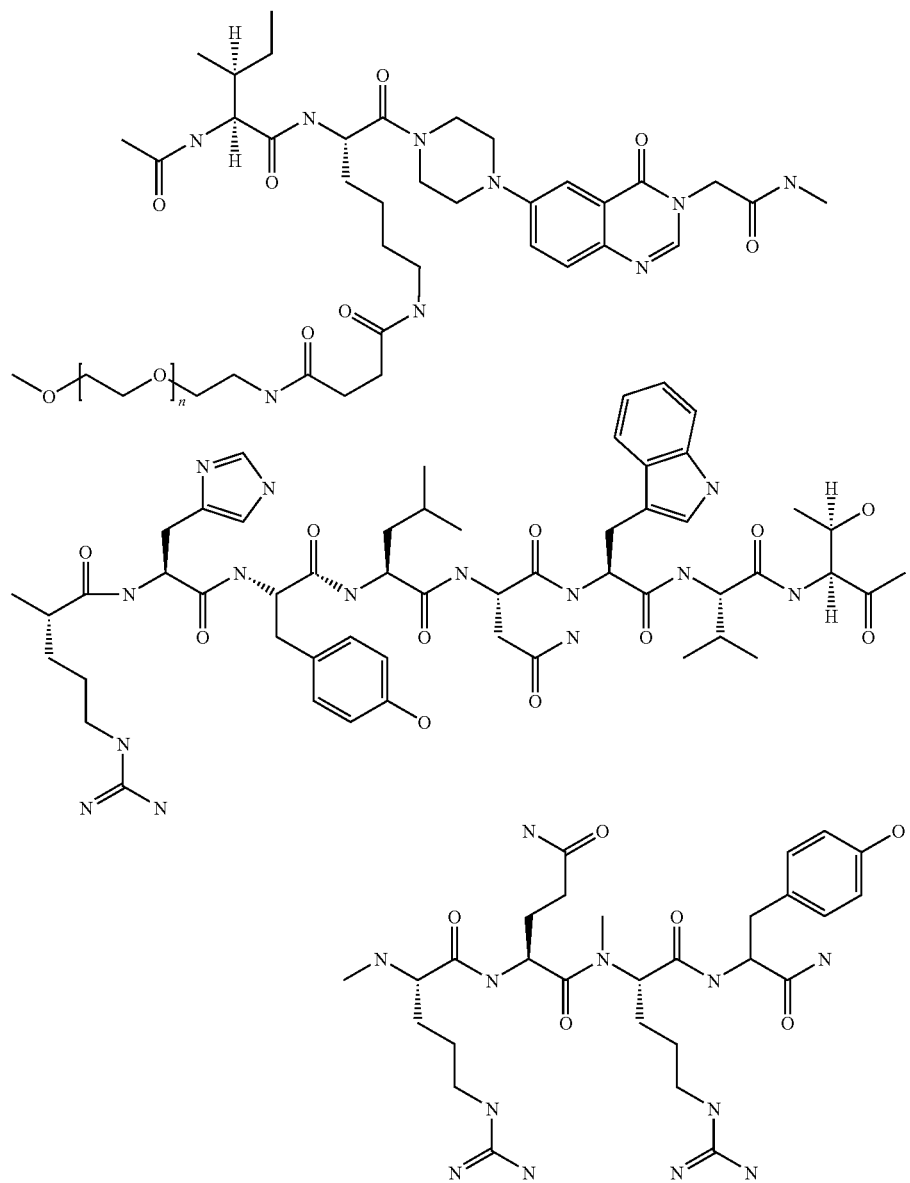

where n=~675

| Analytical Method | Result |
|---|---|
| RP-HPLC1 - rxn mixture | 81.4% conversion |
| RP-HPLC1 - purified | 9.5 min Retention time |
| MALDI-TOF MS | Average Mass = 33.6 kDa |

Figure 16:
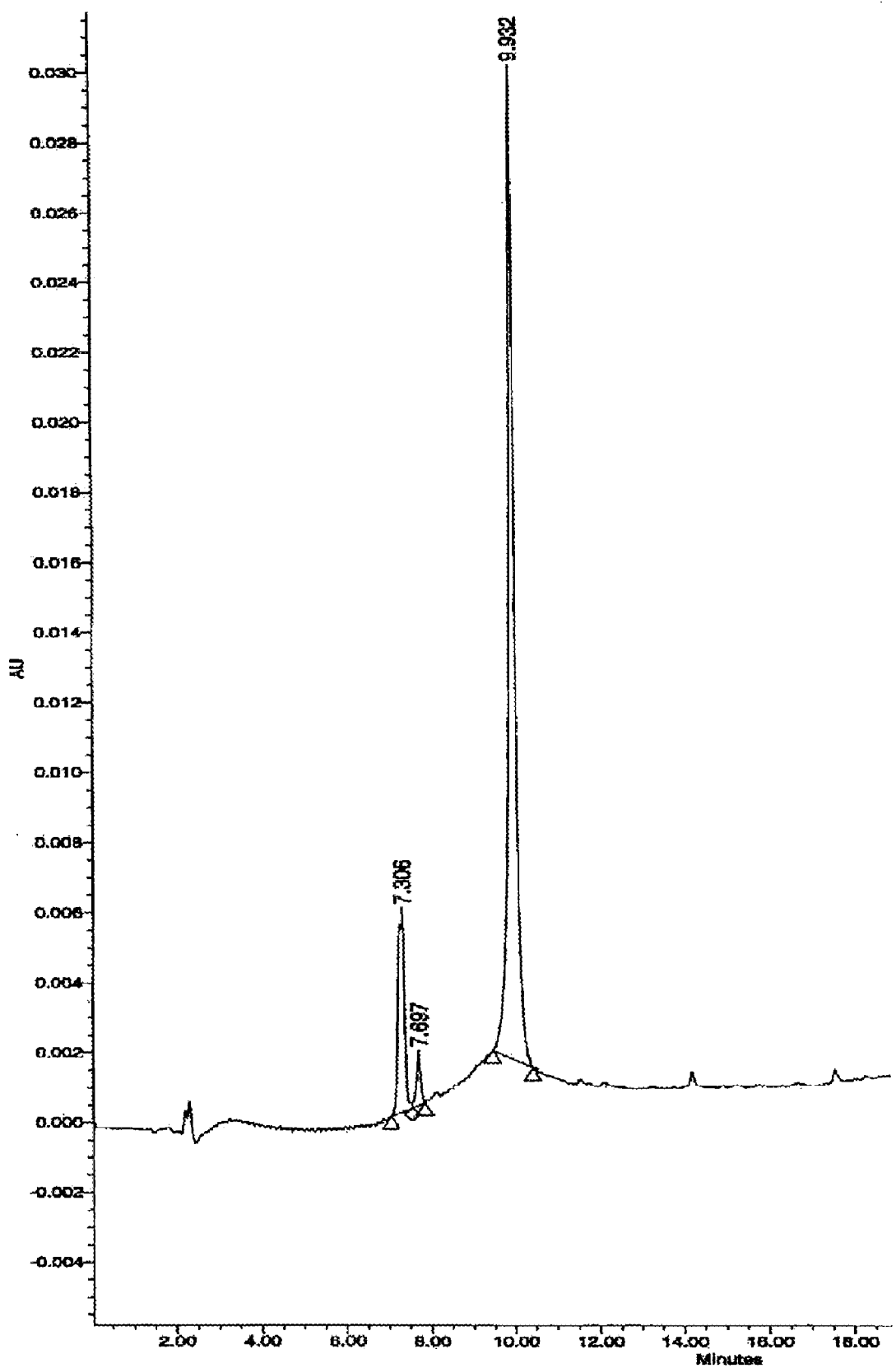
FIG. 16 shows an HPLC chromatogram of a reaction mixture of a compound (example 39) of the present invention.

One hundred mg of peptide from Example 28 was weighed out and dissolved in 50 mM Borate, pH 8.0 buffer. 3.6 g 30 kDa PEG-succinimidyl succinamide was weighed to achieve a 3:1 PEG:peptide molar ratio and added to the dissolved peptide. The reaction mixture was agitated at room temperature overnight before it was diluted 10-fold in 20 mM NaOAc, pH 4.5 buffer and purified by cation exchange chromatography on SP-Sepharose FF. FIG. 16 is an HPLC chromatogram of the reaction mixture. The reaction yielded 81.4% of 30 kDa peptide.

Mono-pegylated PYY peptide was eluted using a step NaCl gradient. Typically, the desired mono-pegylated peptide eluted with 250 mM NaCl. The eluted PEG-PYY-like peptide was concentrated in an Amicon ultrafiltration cell using a 10 kDa MW cutoff membrane. It was then diafiltered 10-fold once with PBS.

Figure 17:
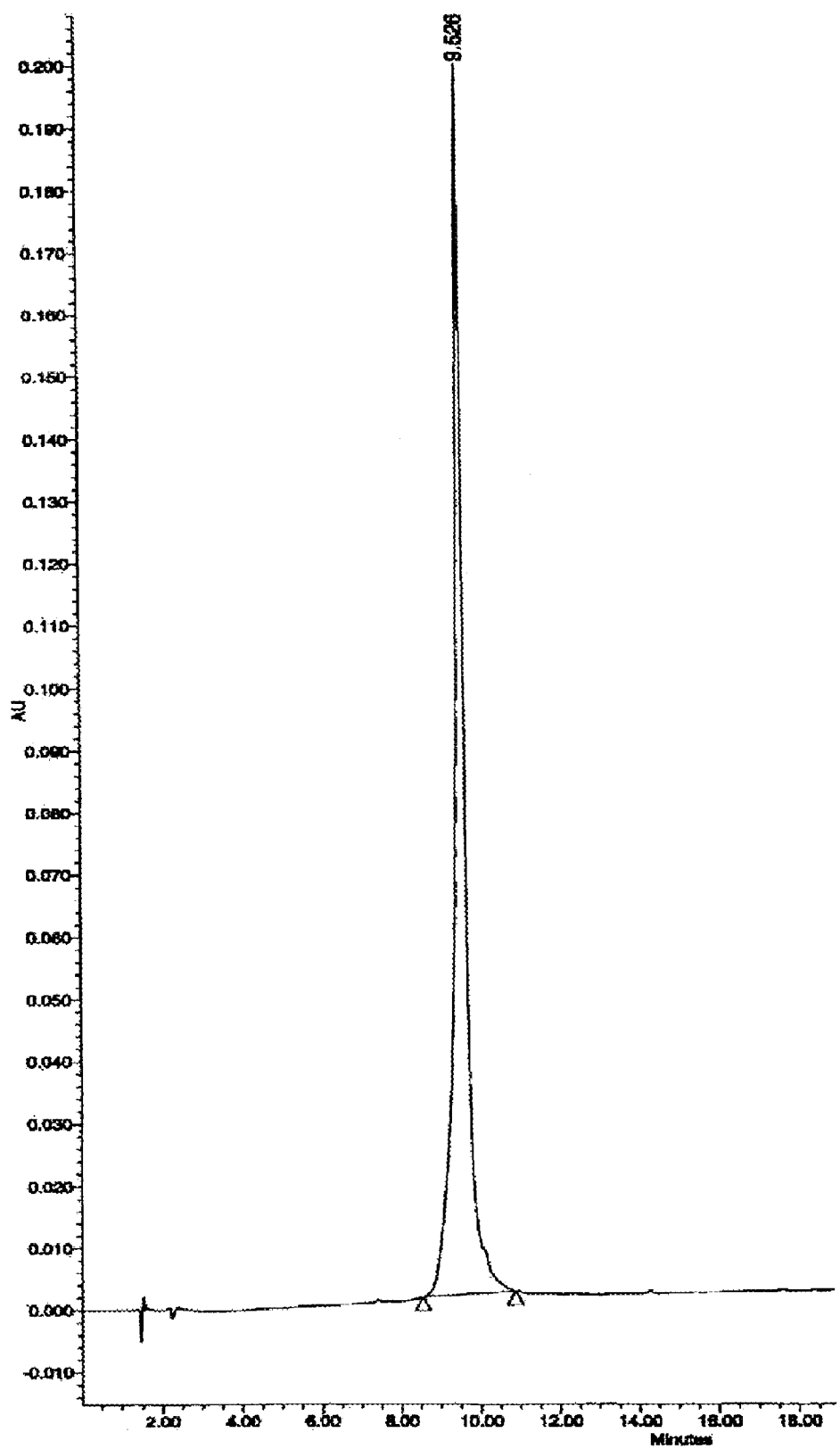
FIG. 17 shows an HPLC chromatogram of a purified compound (example 39) of the present invention.
Figure 18:
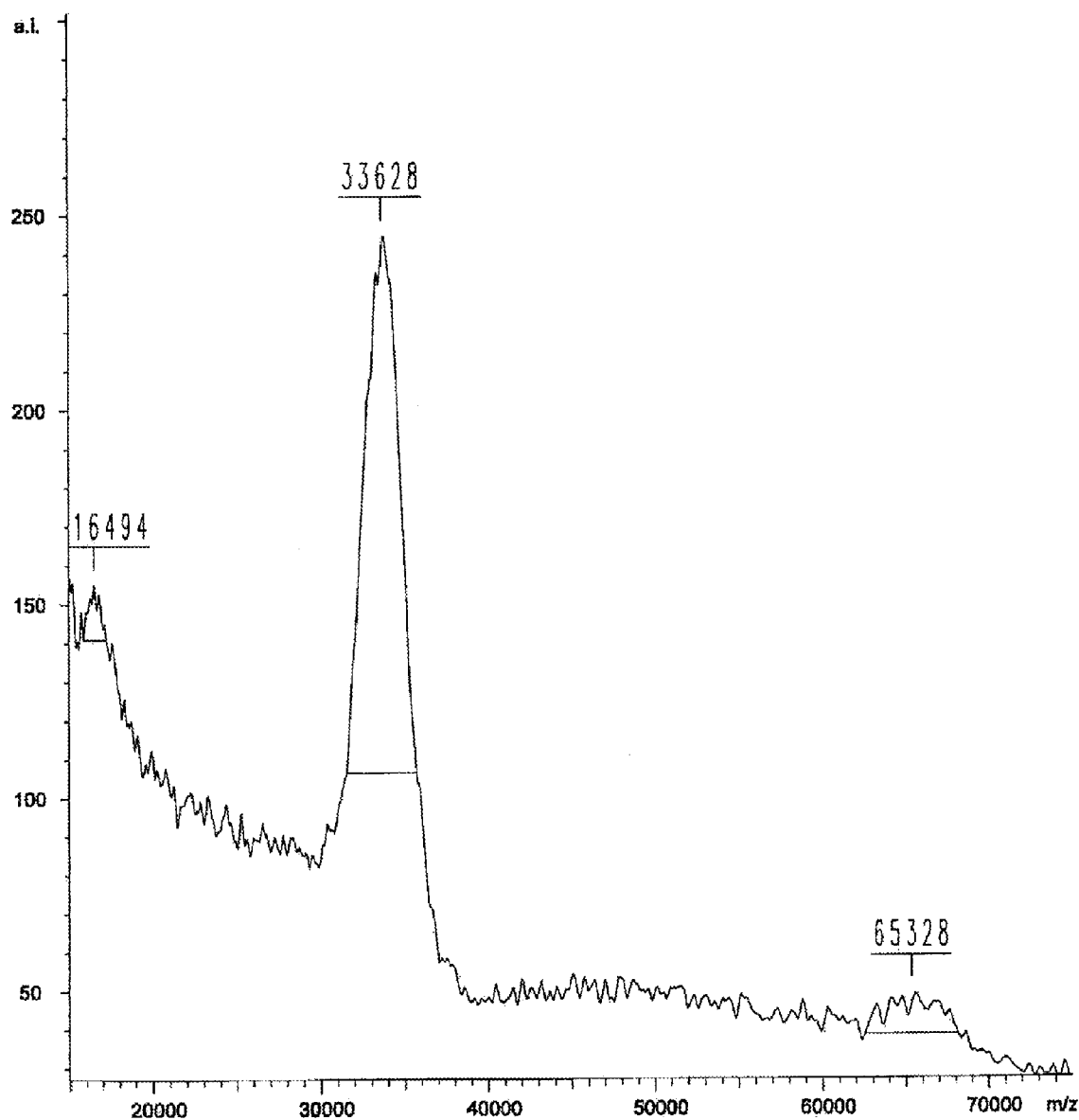
FIG. 18 shows a MALDI-TOF spectrum of yet another compound (example 39) of the present invention.

Concentrated peptide of Example 39 was submitted for analysis, assayed and stored at −20 C. FIG. 17 is an HPLC chromatogram of purified 30 kDa PEG-PYY peptide (RT=9.5 min). Purity of 30 kDa peptide was determined to be >97%. And FIG. 18 is a graph representing a MALDI-TOF of 30 kDa PEG-PYY peptide, which was, performed to confirm the molecular weight.

Example 40

Preparation of Fmoc-Ile-Lys-Pqa-Arg-His-Tyr-Leu-Asn-Trp-Val-Thr-Arg-Gln-(NMe)Arg-Tyr-NH$_2$ (SEQ ID NO: 40)

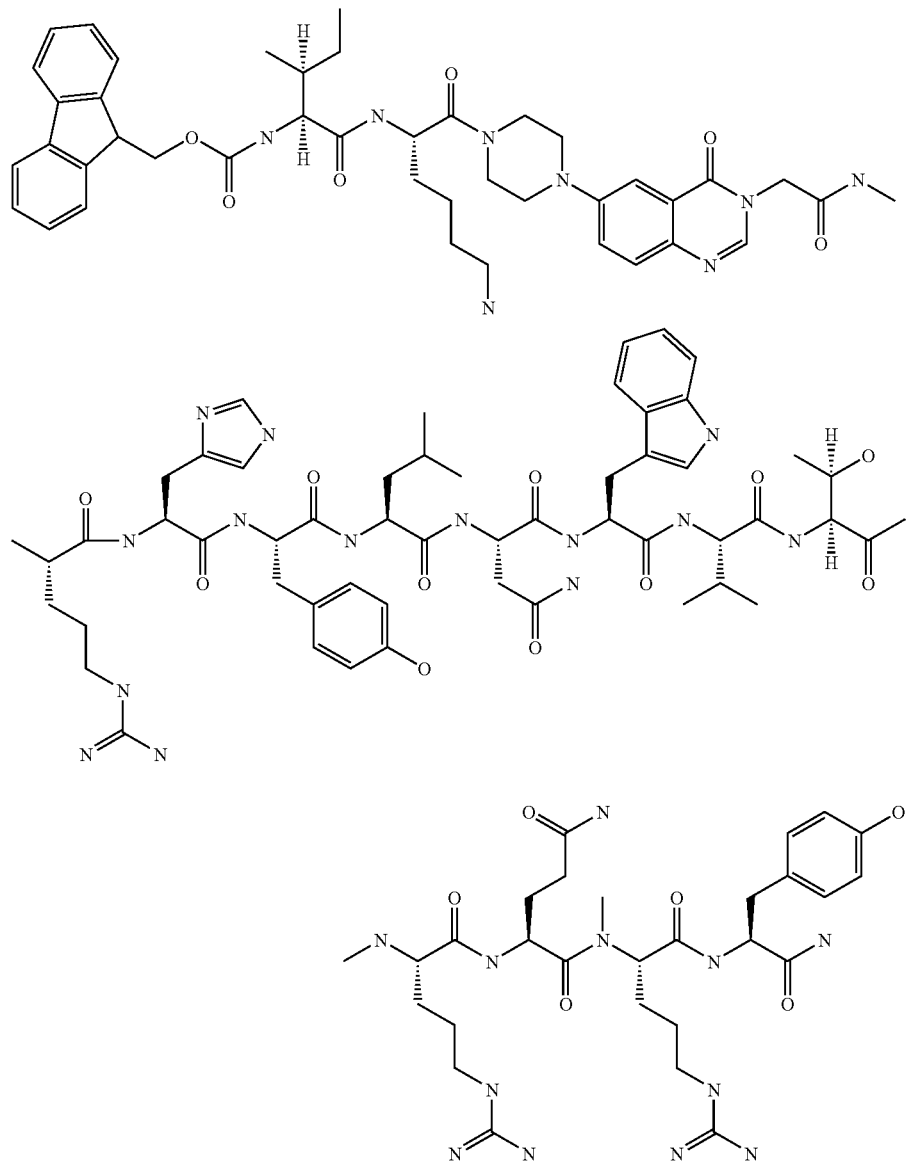

55.0 g Fmoc-linker BHA @0.45 mm/g (purchased from AnaSpec Inc. cat #408/452-5055) was subjected to solid phase peptide synthesis and purification by the following procedure:

Fmoc protected amino acids were couple via DIC/HOBt in 25% excess. (55.0 g×0.45 mm/g×1.25 eqv=31.0 mm). All deprotection was 2×10 min with 20% piperidine in DMF at approximately 10 ml/g (adjusted as volume of peptide-resin increases). After deprotection the peptide resin was washed 4×DMF (20 volumes).

All couplings were with ~40 mL DIC (~6 eqv) and 4.5 g HOBt (1.25 eqv). After coupling the resin solution was sampled ~0.25 ml washed with $CH_2Cl_2$ and checked via ninhydrin for completion. After coupling to NMe-Arg and Pqa, the resin was washed with $CH_2Cl_2$ and checked with 3 drops of 2% Chlorinal in DMAc and 3 drops 2% Acetaldehyde in DMAc (with no change in the yellow solution indicative of no secondary amine and blue to black beads indicative of incomplete coupling). If couplings were judged to be incomplete DIEA was added to the coupling solution and continued for 1 hr further. When complete, the resin was washed 4×DMF (20 volumes).

Fmoc-Tyr(But)-OH: 14.0 g. Fmoc-NMeArg(Mtr)-OH: 20.0 g. Fmoc-Gln(Trt)-OH: 18.5 g. Fmoc-Arg(Pbf)-OH: 20.0 g. Fmoc-Thr(But)-OH: 18.0 g. Fmoc-Val-OH: 10.5 g. Fmoc-Trp-OH: 13.0. Fmoc-Asn(Trt)-OH: 18.0 g. Fmoc-Leu-OH 11.0 g, Fmoc-Tyr(But)-OH 14.0 g, Fmoc-His(Trt)-OH 20.0 g, Fmoc-Arg(Pbf)-OH 20.0 g, Fmoc-Pqa-OH 15.4 g, Fmoc-Lys(Boc)-OH 14.1 g, Fmoc-Ile-OH 11.0 g.

The peptide resin was washed 3×DMF, 3×$CH_2Cl_2$ and 3×MeOH and dried under suction to obtain 115.38 g peptide resin. The resin was split into 6×19.25 g batches for TFA cleavage.

19.25 g of peptide resin was cleaved with 8.0 mL 1:1:1 DTE; Anisole; Thioanisloe, 8.0 mL $iPr_3SiH$, 8.0 mL H2O and 200 mL TFA/for 6 hours (6:30 AM to 13:30 PM), followed by precipitation in 2.0 L cold (–20° C.) Et2O. The precipitate was collected by centrifugation in 8×50 mL polypropylene centrifuge tubes and washed 3× cold Et2O. The precipitate was then dried under house vacuum overnight to obtain 6.5 g of crude peptide. The total amount of crude peptide after 6 deprotection was 38.71 g.

Purification of crude peptide was performed on Shimadzu LC-8A system by high performance liquid chromatography (HPLC) on a reverse phase Pursuit C-18 Column (50×250 mm. 300 A°, 10 um). 38.71 g of crude was purified in 36 preps. Each time approximately 1.1 g of crude peptide was dissolved in a minimum amount of water and acetonitrile and was injected in a column. Gradient elution was generally started at 20% B buffer, 20%-70% B over 70 minutes, (buffer A: 0.1% TFA/$H_2O$, buffer B: 0.1% TFA/$CH_3CN$) at a flow rate of 50 ml/min. UV detection was made at 220/280 nm. The fractions containing the products were separated and purity was judged on Shimadzu LC-10AT analytical system using reverse phase Pursuit C18 column (4.6×50 mm) at a flow rate of 2.5 ml/min., gradient (20-70%) over 10 min. [buffer A: 0.1% TFA/H2O, buffer B: 0.1% TFA/CH3CN)]. Fractions judged to be of high purity were pooled and lyophilized to yield white amorphous powder. Lyophilized product from thirty-six preps was combined and lyophilized again to yield 8.233 g of pure peptide (12.6%). Purity of the final product was checked again by analytical HPLC on a reversed phase column as stated above and was approximately 95-99%. (ES)+-LCMS m/e calcd for $C_{119}H_{164}N_{34}O_{23}$ 2438.85, found 2438.84

Example 41

Preparation of Ile((PEG-30,000) $CH_2CH_2NHCOCH_2CH_2CO)(\epsilon)$Lys-Pqa-Arg-His-Tyr-Leu-Asn-Trp-Val-Thr-Arg-Gln-(NMe)Arg-Tyr-$NH_2$ (SEQ ID NO: 41)

| Analytical Method | Result |
|---|---|
| RP-HPLC2 | 93.8% conversion - protected PEG-peptide 89.5% yield overall - deprotected PEG-peptide |
| RP-HPLC2 - purified | 10.1 min Retention time |
| MALDI-TOF MS | Average Mass = 35 kDa |

Figure 19:
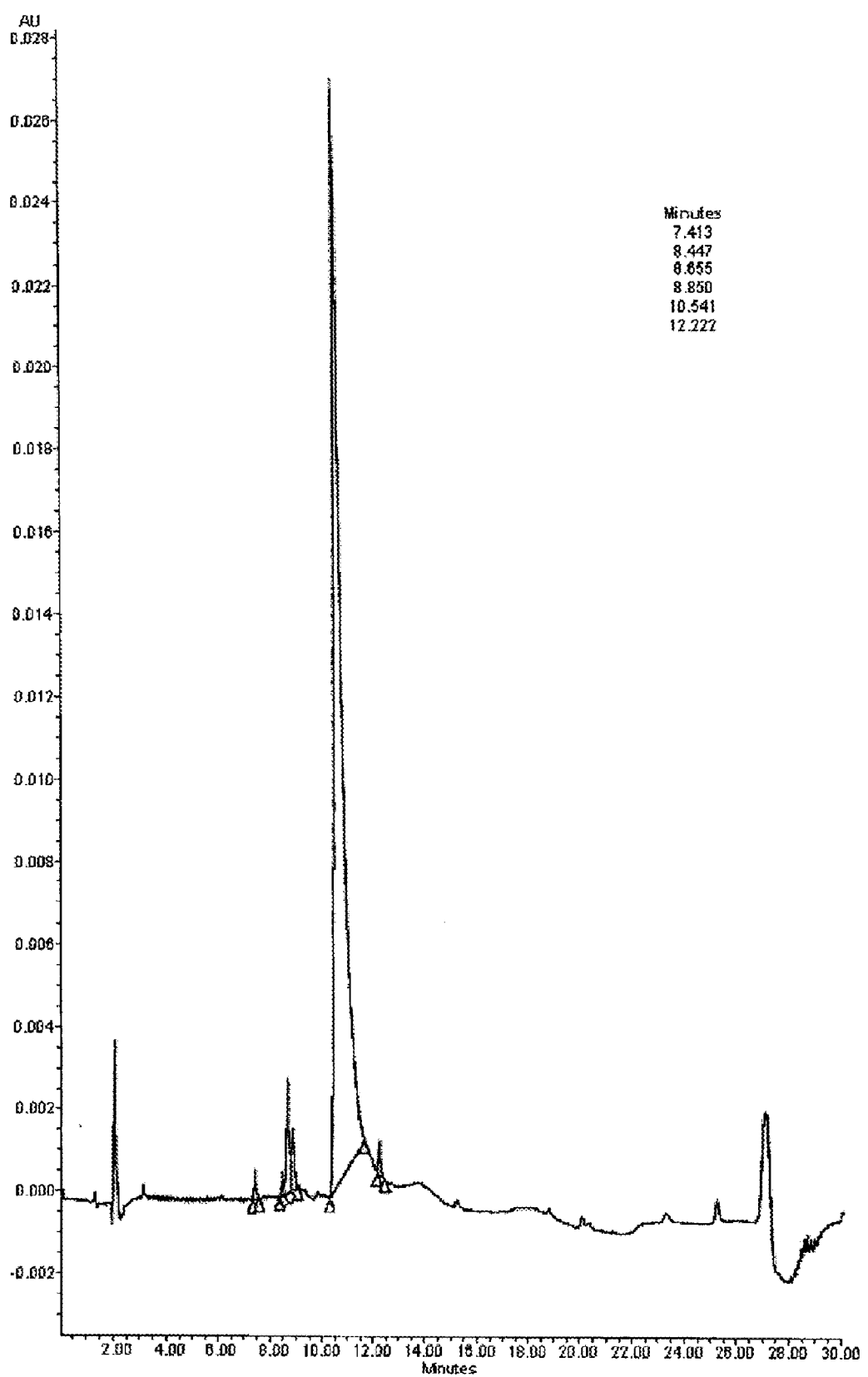
FIG. 19 shows an HPLC chromatogram of a reaction mixture containing a compound (example 41) of the present invention before deprotection.
Figure 20:
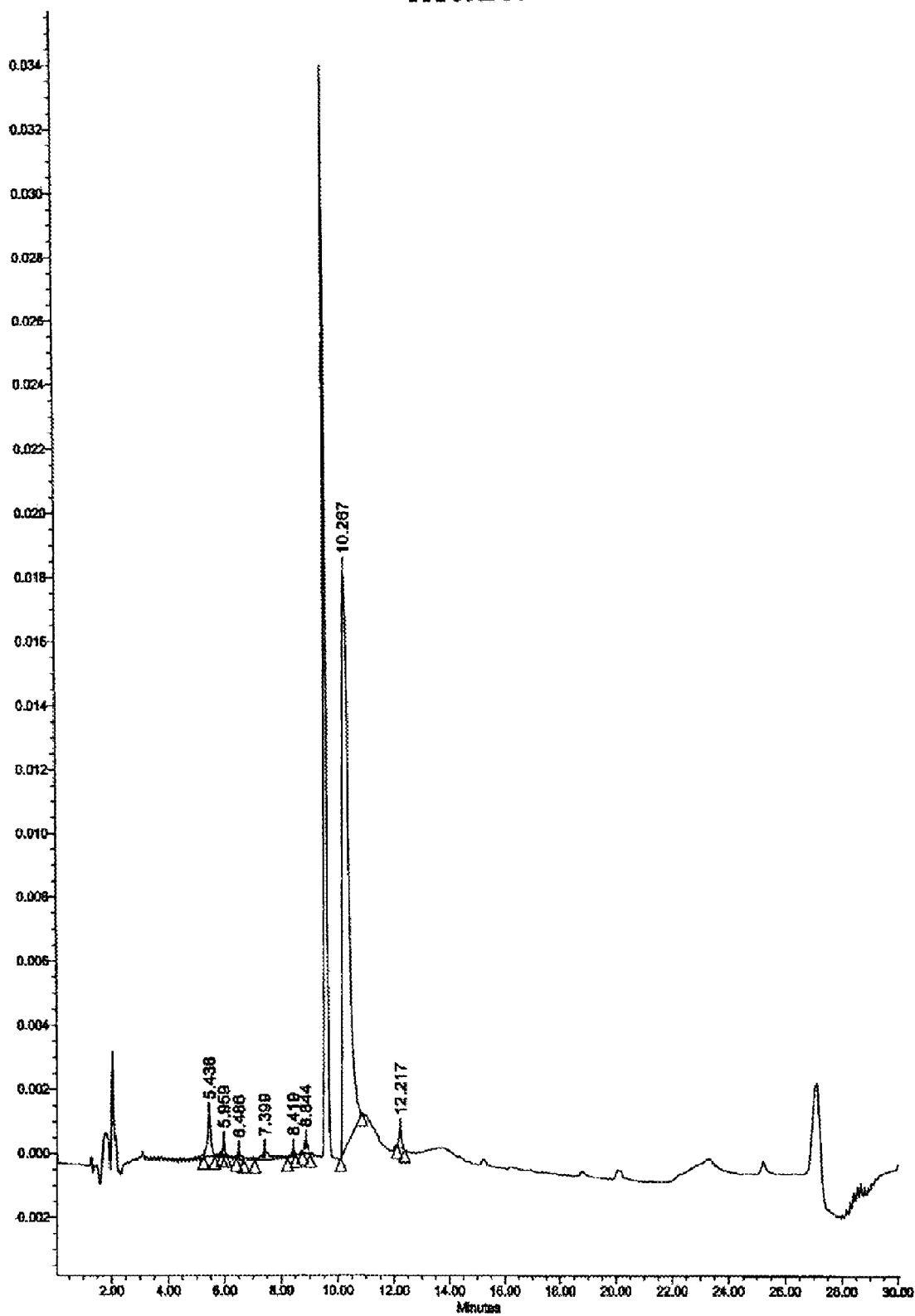
FIG. 20 shows an HPLC chromatogram of a deprotected reaction mixture containing a compound (example 41) of the present invention.

1.8 g of peptide from Example 40 was weighed out and dissolved in 50 mM Borate, pH 7.5 buffer. 37.5 g 30 kDa PEG-succinimidyl succinamide was weighed to achieve an approximate 2:1 PEG:peptide molar ratio and added to the dissolved peptide. The reaction mixture was stirred at room temperature for 2 h. The pegylated peptide was deprotected by adding piperidine (20%) to the reaction mixture for 1 h at room temperature. The reaction mixture was placed on ice and acidified by slow addition of glacial acetic acid (20%). The reaction mixture was then diluted 10-fold in 20 mM NaOAc, pH 4.5 buffer and purified by cation exchange chromatography on SP-Sepharose FF. FIG. 19 is an HPLC chromatogram of the reaction mixture. The reaction yielded 93.8% of protected pegylated peptide. FIG. 20 is an HPLC chromatogram of the deprotected reaction mixture, whereby the overall yield of pegylated deprotected peptide was 89.5%.

Mono-pegylated PYY peptide was eluted using a step NaCl gradient. Typically, the desired mono-pegylated peptide eluted with 175 mM NaCl. The eluted PEG-PYY-like peptide was concentrated in an Amicon ultrafiltration cell using a 10 kDa MW cutoff membrane. It was then diafiltered 10-fold once with PBS.

Figure 21:
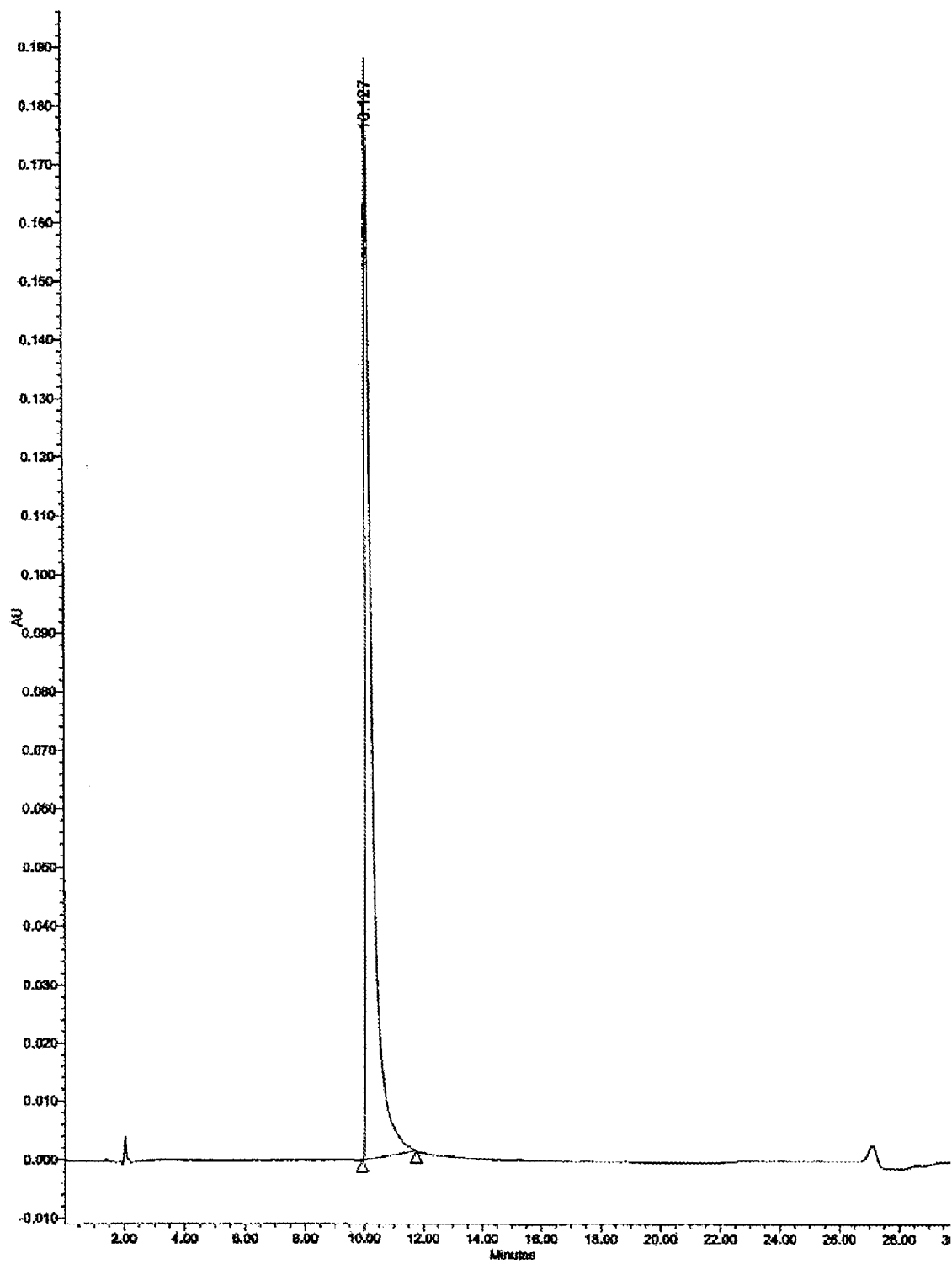
FIG. 21 shows an HPLC chromatogram of a purified compound (example 41) of the present invention.
Figure 22:
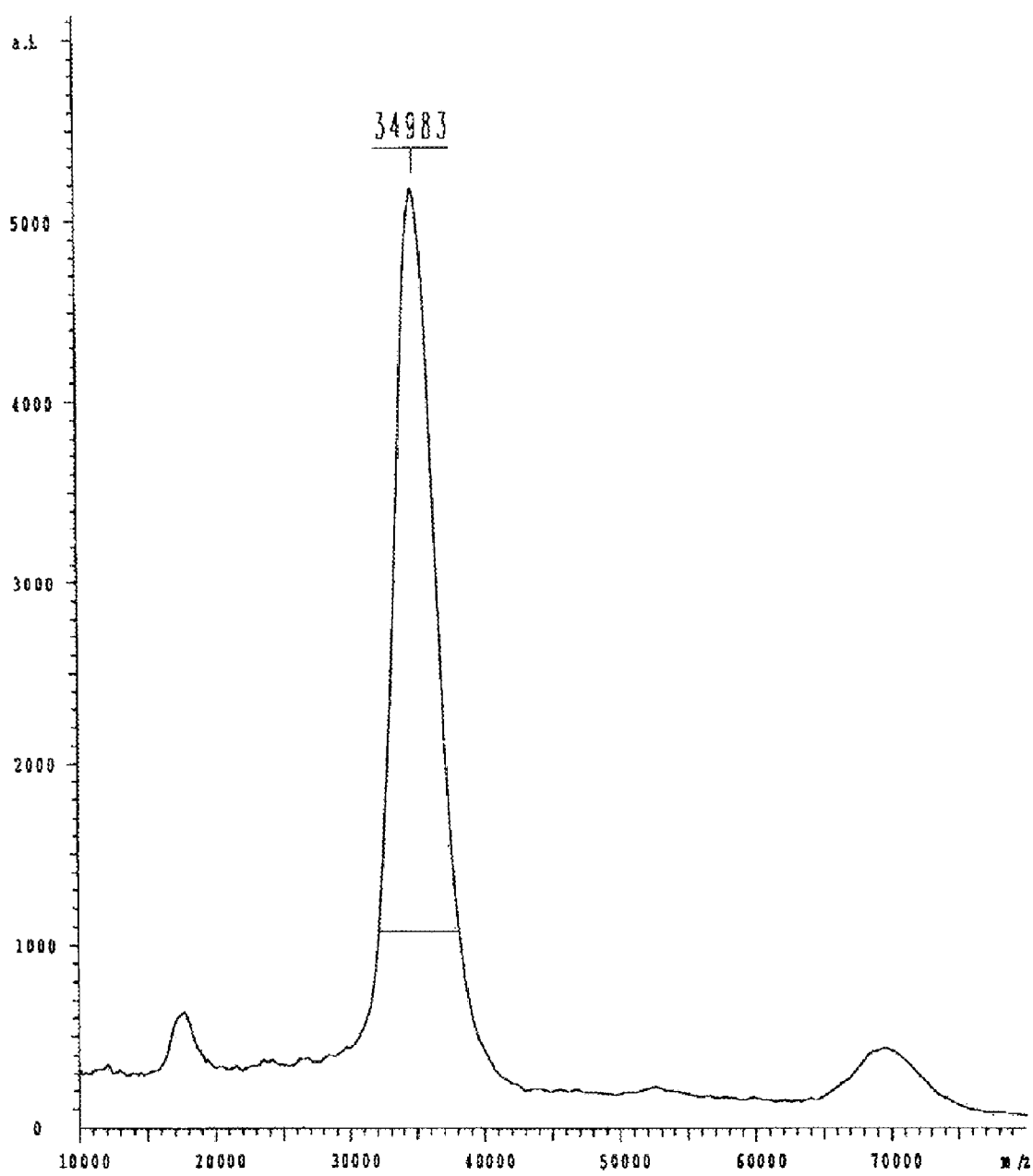
FIG. 22 shows a MALDI-TOF spectrum of a compound (example 41) of the present invention.

Concentrated peptide was submitted for analysis, assayed and stored at –20 C. FIG. 21 is an HPLC chromatogram of purified 30 kDa PEG-PYY peptide (RT=10.1 min). Purity of 30 kDa peptide was determined to be >95%. And FIG. 22 is a graph representing a MALDI-TOF of 30 kDa PEG-PYY peptide, which was performed to confirm the molecular weight.

Example 42

Calcium Flux Assay

HEK-293 cells stably transfected with the G protein chimera $G\alpha qi9$ and the hygromycin-B resistance gene were further transfected with the human NPY2 receptor and G418 antibiotic selection. Following selection in both hygromycin-B and G418, individual clones were assayed for their response to PYY. The transfected cells (HEK293/hNPY2R) were cultured in DMEM medium supplemented with 10% fetal bovine serum, 50 µg/ml hygromycin-B, 2 mM glutamine, 100 U/ml penicillin, 100 µg/ml streptomycin and 250 µg/ml G418. Cells were harvested with trypsin-EDTA and counted using ViaCount reagent. The cell suspension volume was adjusted to 4.8×$10^5$ cells/ml with complete growth media. Aliquots of 25 µl were dispensed into 384-well Poly-D Lysine coated black/clear microplates (Falcon) and the microplates were placed in a 37° C. CO$_2$ incubator overnight.

Loading Buffer (Calcium-3 Assay Kit, Molecular Devices) was prepared by dissolving the contents of one vial (Express Kit) into 1000 ml Hank's Balanced Salt Solution (HBSS) containing 20 mM HEPES and 5 mM probenecid. Aliquots (25 µl) of diluted dye were dispensed into the cell plates and the plates were then incubated for 1 h at 37° C.

During the incubation, test compounds were prepared at 3.5× the desired concentration in HBSS (20 mM HEPES)/0.05% BSA/1% DMSO and transferred to a 384-well plate for use on FLIPR® (FLIPR, Fluorescent Imaging Plate Reader, is a registered trademark of Molecular Devices Corp.).

After incubation, both the cell and compound plates were brought to the FLIPR® and 20 µL of the diluted compounds were transferred to the cell plates by the FLIPR®. During the assay, fluorescence readings were taken simultaneously from all 384 wells of the cell plate every 1.5 seconds. Five readings were taken to establish a stable baseline, and then 20 µl of sample was rapidly (30 µl/sec) and simultaneously added to each well of the cell plate. The fluorescence was continuously monitored before, during and after sample addition for a total elapsed time of 100 seconds. Responses (increase in peak fluorescence) in each well following addition was determined. The initial fluorescence reading from each well, prior to ligand stimulation, was used as a zero baseline value for the data from that well. The responses were expressed as a percentage of maximal response of the positive control.

Example 43

Cyclic AMP Assay

In this example, the following materials were used: 384-well plate; Tropix cAMP-Screen Kit: (Applied Biosystems, Cat. #T1504); forskolin (Calbiochem Cat. #344270); cells: HEK293/hNPY2R cells; plating medium: DMEM/F12 w/o phenol red (Gibco Cat #1133032); 10% heat inactivated FBS (Gibco Cat. #10082-147); 1% Penicillin/Streptomycin (Gibco Cat. #15140-122); 500 mg/ml G418 (Geneticin, Gibco Cat. #11811-031).

HEK293/hNPY2R cells were plated at a density of $10^4$ cells/well in a 384-well plate using Multi-drop dispenser and the plates were incubated overnight at 37° C. The next day, cells that reached 75-85% confluence were used in the experiment. The media and reagents were warmed to room temperature. Before the dilutions were prepared, the stock solution of Y2-receptor ligands and controls in dimethyl sulphoxide (DMSO, Sigma Cat#D2650) was allowed to warm up to 32° C. for 5-10 min. The dilutions were performed using incubation media [DMEM/F12 media containing 0.5 mM 3-isobutyl-1-methylxanthine (IBMX, Calbiochem Cat #410957) and 0.5 mg/ml BSA (Sigma Cat #A8806)]. The final concentrations of DMSO and forskolin in the incubation medium were 1.1% and 5 µM, respectively.

The plating media was removed by gentle inversion of the 384-well plate on a paper towel and replaced with incubation medium (50 µl/well) containing various concentrations of Y2-receptor ligands (four replicates/concentration). The plates were incubated at room temperature for 30 min. Following the 30 min treatment period, the incubation media was discarded and replaced with 50 µl/well of Assay Lysis Buffer (provided in the Tropix kit). The cells were lysed by incubating plates for 45 min @ 37° C. The lysate (20 µl) was transferred into the pre-coated antibody plates (384-well) supplied in the Tropix kit. AP conjugate (10 µl) and of anti-cAMP antibody (20 µl) was added to each well and the plates incubated on a shaker at room temperature for 1 h. The plates were washed 5 times with Wash Buffer (70 µl/well/wash) and the plates tapped dry. CSPD/Saphire-II RTU substrate/enhancer solution (30 µl/well) was added and incubated for 45 min @ room temperature. The signal in each well was measured (1 sec/well) using a Luminometer (VICTOR-V).

The compounds of the present invention exhibited selective Neuropeptide-2 receptor activity in vitro, as demonstrated in the calcium flux assay (FLIPR®; Example 42) and cyclic AMP assay (Example 43). Summary of the in vitro results, $EC_{50}$ for Examples 3 to 39 and 41, are illustrated in Table 1 below (SEQ ID NOS 1-32, 34, 36-39 & 41 disclosed respectively in order of appearance):

| Example | Sequence | Y2R EC50 (nM) FLIPR | Y2R EC50 (nM) cAMP | Y1R EC50 (nM) FLIPR | Y4R EC50 (nM) FLIPH | Y5R EC50 (nM) FLIPR |
|---|---|---|---|---|---|---|
| 3 | IKPEAPGEDASPEELNRVYASLRHYLNLVTRQRY (3-36) | 0.12 | 0.033 | 63 | 3238 | 265 |
| 4 | IK-Pqa-RHYLNLVTRQRY | 0.28 | 0.047 | 57 | >5000 | 1887 |
| 5 | IK-Pqa-RHYLNLVTRQ(N-methyl)RY | 2.3 | 0.42 | >5000 | >5000 | >5000 |
| 6 | IK-Pqa-RHYLNLVTRQ(N-methyl)R (m-)Y | 3.32 | 1.5 | >5000 | >5000 | >5000 |
| 7 | IK-Pqa-RHYLNLVTRQ(N-methyl)R (3-1)Y | 1.15 | 0.31 | 173 | >5000 | >5000 |
| 8 | IK-Pqa-RHYLNLVTRQ(N-methyl)R (3-5 di F)Y | 0.15 | 0.36 | >5000 | >5000 | >5000 |
| 9 | IK-Pqa-RHYLNLVTRQ(N-methyl)R (2-6 di F)Y | 0.11 | 0.19 | 303 | >5000 | >5000 |
| 10 | IK-Pqa-RHYLNLVTRQ(N-methyl)R (2-6 di Me)Y | 0.28 | 0.67 | 762 | >5000 | >5000 |
| 11 | IK-Pqa-RHYLNLVTRQ(N-methyl)RF(O-CH3) | 0.74 | 0.55 | 189 | >5000 | >5000 |
| 12 | IK-Pqa-RHYLNLVTRQ(N-methyl)RF | 1.54 | 0.69 | 422 | >5000 | >5000 |
| 13 | IK-Pqa-RHYLNLVTRQ(N-methyl)R(4-NH2)Phe | 11.4 | 0.31 | >5000 | >5000 | >5000 |

-continued

| Example | Sequence | Y2R EC50 (nM) FLIPR | Y2R EC50 (nM) cAMP | Y1R EC50 (nM) FLIPR | Y4R EC50 (nM) FLIPH | Y5R EC50 (nM) FLIPR |
|---|---|---|---|---|---|---|
| 14 | IK-Pqa-RHYLNLVTRQ(N-methyl)R(4-F)Phe | 0.45 | 0.96 | >5000 | >5000 | 2259 |
| 15 | IK-Pqa-RHYLNLVTRQ(N-methyl)R(4-CH20H)Phe | 0.46 | 0.45 | >5000 | >5000 | >5000 |
| 16 | IK-Pqa-RHYLNLVTRQ(N-methyl)R(4-CF3)Phe | 6.13 | 3.55 | 3268 | >5000 | 729 |
| 17 | IK-Pqa-RHYLNLVTRQ(N-methyl)R(3-F)Phe | 0.635 | 0.75 | >5000 | >5000 | >5000 |
| 18 | IK-Pqa-RHYLNLVTRQ(N-methyl)R(2, 3.4, 5, 6-Penta-F)Phe | 11.9 | 2.5 | >5000 | >5000 | >5000 |
| 19 | IK-Pqa-RHYLNLVTRQ(N-methyl)R(3.4-diCl)Phe | 4.03 | 1.47 | >5000 | >5000 | >5000 |
| 20 | IK-Pqa-RHYLNLVTRQ(N-methyl)RCH | 0.498 | 0.5 | >5000 | >5000 | 352 |
| 21 | IK-Pqa-RHYLNLVTRQ(N-methyl)RW | 0.454 | 1.06 | >5000 | >5000 | >5000 |
| 22 | IK-Pqa-RHYLNLVTRQ(N-methyl)R(1)Na1 | 2.73 | 1.14 | >5000 | >5000 | 4772 |
| 23 | IK-Pqa-RHYLNLVTRQ(N-methyl)R(2)Nal | 4.11 | 2.4 | >5000 | >5000 | 2162 |
| 24 | IK-Pqa-RHYLNLVTRQR-C-☐-Me-Tyr | 5.44 | 1.35 | 3259 | >5000 | |
| 25 | IK-Pqa-RHYLNWVTRQ(N-methyl)RY | 0.44 | 0.25 | 298 | >5000 | >5000 |
| 26 | INle-Pqa-RHYLNWVTRQ(N-methyl)RY | 8.1 | 0.108 | >5000 | >5000 | >5000 |
| 27 | Ac-IK-Pqa-RHYLNwVTRQ(N-methyl)R(2.6 di F)Y | 1.44 | 0.07 | >5000 | >5000 | 5812 |
| 28 | Ac-IK-Pqa-RHYLNWVTRQ(N-methyl)RY | 0.458 | 0.18 | >5000 | >5000 | >5000 |
| 29 | Pentyl-IK-Pqa-RHYLNWVTRQ(N-methyl)RY | 0.873 | 0.51 | >5000 | >5000 | >5000 |
| 30 | Trimetyl acetyl-IK-Pqa-RHYLNWVTRQ(N-methyl)RY | 1.1 | 0.26 | >5000 | >5000 | >5000 |
| 31 | Cyclohexyl-IK-Pqa-RHYLNWVTRQ(N-methyl)RY | 1.67 | 1.37 | >5000 | >5000 | >5000 |
| 32 | Benzoyl-IK-Pqa-RHYLNWVTRQ(N-methyl)RY | 0.79 | 0.66 | >5000 | >5000 | >5000 |
| 33 | Adamtyl-IK-Pqa-RHYLNWVTRQ(N-methyl)RY | 2.33 | 2.9 | >5000 | >5000 | >5000 |
| 34 | (PEG 30,000 SPA)IK-Pqa-RHYLNWVTRQ(N-methyl)RY | 37.9 | 18 | >5000 | >5000 | >5000 |
| 35 | (PEG40,000 BTC)-IK-Pqa-RHYLNWVTRQ(N-methyl)RY | 590 | 14.7 | >5000 | >5000 | >5000 |
| 36 | (PEG30,000)-SSA-INle-Pqa-RHYLNWVTRQ(N-methyl)RY | 289 | 7.8 | >5000 | >5000 | >5000 |
| 37 | (PEG30,000)-bcta-SBA-INle-Pqa-RHYLNWVTRQ(N-methyl)RY | 239 | 22.4 | >5000 | >5000 | >5000 |
| 38 | Ac-Ile-Lys(PEG30,000 SPA)-Pqa-RHYLNwVTRQ(N-methyl)RY | 549 | 24.4 | >5000 | >5000 | >5000 |
| 39 | Ac-Ile-Lys(PEG30,000 SSA)-Pqa-RHYLNWVTRQ(N-methyl)RY | 1078 | 20.7 | >5000 | >5000 | >5000 |
| 41 | IK(PEG30,000 SSA)-Pqa-RHYLNWVTRQ(N-methyl)RY | 13.5 | 9.8 | >5000 | >5000 | >5000 |

Example 44

Chronic DIO Rat Studies

Male Sprague Dawley rats (7 weeks old) were obtained from Charles River Laboratories (USA) and housed in a temperature and humidity controlled environment with a 12 h light:12 h dark cycle. The rats were given ad libitum access to a high fat chow diet (HFD; 60% of dietary kcal as fat, Research Diets D12492) and water throughout the study. Following 7 weeks on the HFD, rats were sorted by body weight and caged singly. The rats were dosed prior to onset of dark cycle with vehicle (s.c.) or compound of Example 41 (1, 5 and 10 mg/kg, s.c.) once every two days for 3 weeks (N=6-8 rats/group). Body weight was recorded on days indicated in FIG. 23.

Data Analysis:

All data shown are the mean±standard error (s.e.m.). Statistical evaluation of the data was carried out using one-way ANOVA, followed by Dunnett's test to determine where statistically significant differences existed between vehicle and drug treated groups. Differences were considered statistically significant at $P<0.05$. Data analysis was carried out with GraphPad software (GraphPad Prism).

Figure 23:
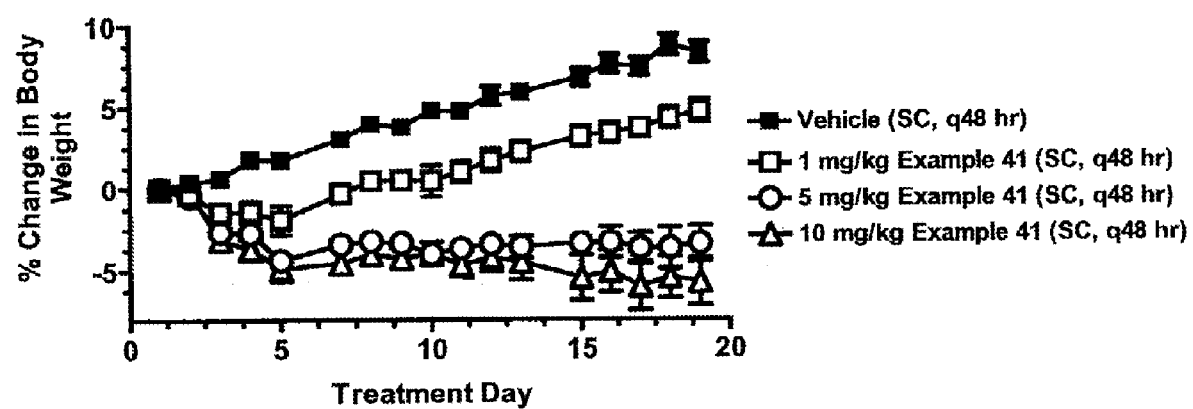
FIG. 23 shows the effect of sub-chronic dosing of a compound (example 41) on body weight in male diet-induced obese (DIO) rats.

Results:

Chronic administration of the compound of Example 41 (5 and 10 mg/kg, q48 hr, s.c.) in male DIO rats induced a significant decrease in body weight gain versus vehicle-treated animals following a 3-week treatment period (FIG. 23).

Acute db/db Mouse Studies

Female db/db mice (C57BL/KsJ-Lep$^{db/db}$, Jackson Laboratories, USA) were at 6 weeks of age when received. The mice were housed in a temperature and humidity controlled environment with a 12 h light:12 h dark cycle, and given access to food (Purina rodent chow 5008) and water ad libitum. The mice (12-weeks old) were pre-bled 4 days prior to study, and those within a narrow range of fasted blood glucose levels were selected for the study in order to minimize variability between vehicle control and drug-treated groups. The mice were administered vehicle (s.c.) or the compound of Example 41 (0.3, 1 and 10 mg/kg, s.c.) 28 hr prior to the oral glucose tolerance test (N=10 mice/group). Blood samples were collected from tail clips following a 6 hr fast, for determination of baseline values (t=0 min). The mice were then gavaged with an oral bolus of glucose (1 g/kg), and additional blood samples were collected at regular intervals (t=30, 60 and 120 min) for glucose measurement. To analyze the effects of the compound of Example 41 on oral glucose tolerance the absolute difference in blood glucose from baseline (fasting blood glucose) was calculated for each time point. The area under the curve ($AUC_{0-120\ min}$) was determined using the trapezoid method.

Data Analysis:

All data shown are the mean±standard deviation (s.d.). Statistical evaluation of the data was carried out using one-way ANOVA, followed by Dunnett's test to determine where statistically significant differences existed between vehicle and drug treated groups. Differences were considered statistically significant at $P<0.05$. Data analysis was carried out with GraphPad software (GraphPad Prism).

Figure 24:
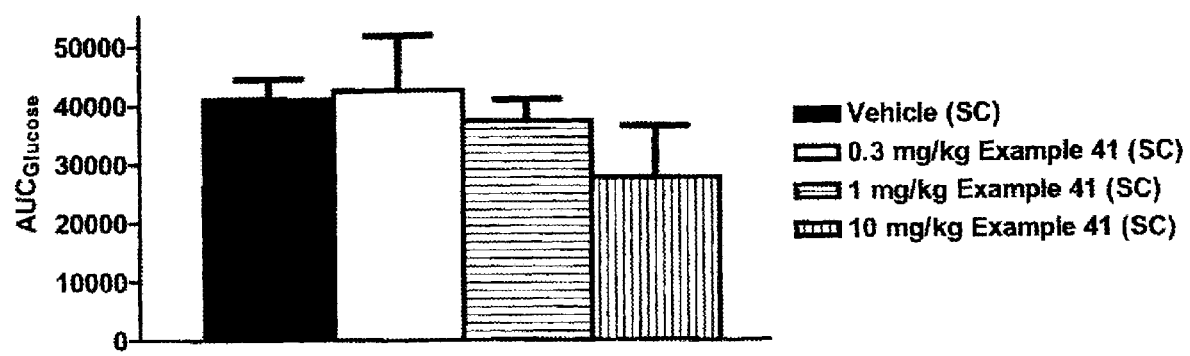
FIG. 24 shows the acute effect of a compound (example 41) on an oral glucose tolerance test (OGTT) in female db/db mice.

Results:

An acute administration of the compound of Example 41 (1 and 10 mg/kg, s.c.) to female db/db mice significantly decreased glucose excursion in response to an oral glucose challenge (FIG. 24).

Chronic db/db Mouse Studies

Female db/db mice (C57BL/KsJ-Lep$^{db/db}$, Jackson Laboratories, USA) were at 6 weeks of age when received. The mice were housed in a temperature and humidity controlled environment with a 12 h light:12 h dark cycle, and given access to food (Purina rodent chow 5008) and water ad libitum. The mice (9 week old) were pre-bled 4 days prior to drug treatment, and those within a narrow range of fasted blood glucose levels were selected for the study in order to minimize variability between vehicle control and drug-treated groups. The mice were dosed with vehicle (s.c.) or the compound of Example 41 (1, 3 and 10 mg/kg, s.c.) once every two days for 3 weeks (N=10 mice/group). Basal fasting (2 to 6 hr) blood glucose measurements were conducted weekly. On study day 20, an oral glucose tolerance test was performed following a 6 hr fast. Blood samples were collected from tail clips for determination of baseline values (t=0 min). The mice were then gavaged with an oral bolus of glucose (1 g/kg), and additional blood samples were collected at regular intervals (t=30, 60, and 120 min) for glucose measurement. To analyze the effects of the compound of Example 41 on oral glucose tolerance the absolute difference in blood glucose from baseline (fasting blood glucose, t=0 min) was calculated for each time point. The area under the curve ($AUC_{0-120\ min}$) was determined using the trapezoid method.

Data Analysis:

All data shown are the mean±standard deviation (s.d.). Statistical evaluation of the data was carried out using one-way ANOVA, followed by Dunnett's test to determine where statistically significant differences existed between vehicle and drug treated groups. Differences were considered statistically significant at $P<0.05$. Data analysis was carried out with GraphPad software (GraphPad Prism).

Figure 25:
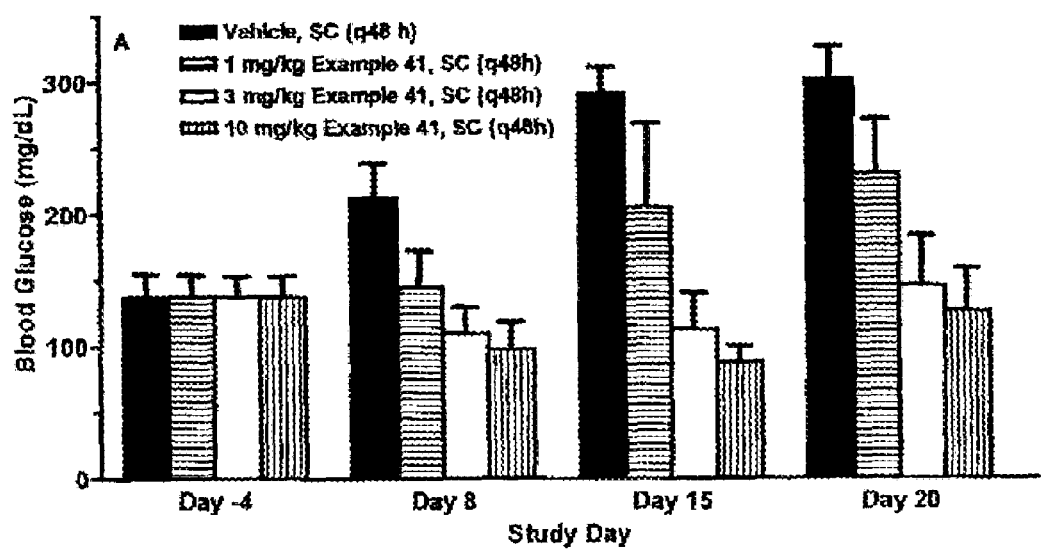
FIG. 25 shows the effect of sub-chronic dosing of a compound (example 41) on basal blood glucose (A) and oral glucose tolerance test (B) in female db/db mice.
Figure 25:
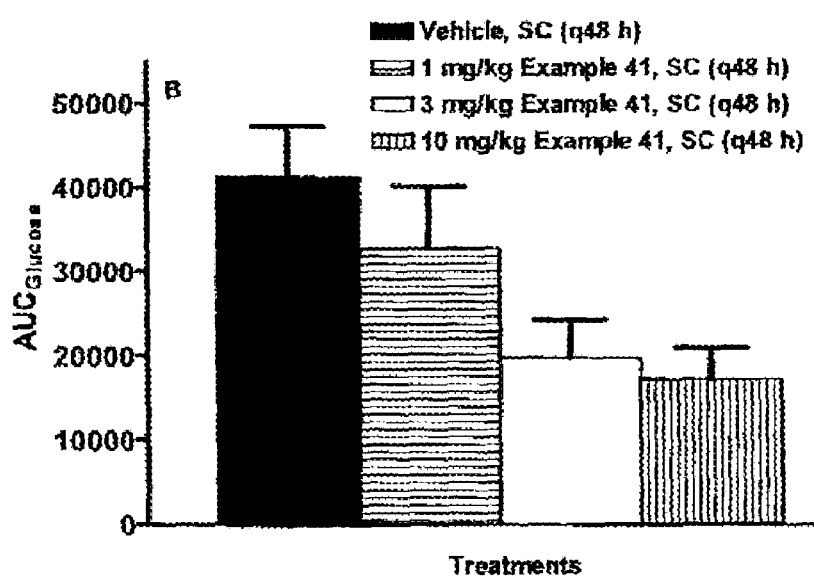

Results:

Chronic administration of the compound of Example 41 (1, 3 and 10 mg/kg, q48 hr, s.c.) to female db/db mice reduced basal blood glucose levels (day 8, 15 and 21) versus vehicle-treated animals during the 3-week treatment period (FIG. 25A). As shown in FIG. 25B, on day 20 the compound of Example 41 (both at 3 and 10 mg/kg, q48 hr, s.c.) significantly decreased glucose excursion in response to an oral glucose challenge.

It is to be understood that the invention is not limited to the particular embodiments of the invention described above, as variations of the particular embodiments may be made and still fall within the scope of the appended claims.

What is claimed is:

1. A neuropeptide-2 receptor agonist, wherein said agonist is (PEG 30,000)-SPA-IK-Pqa-RHYLNWVTRQ(N-methyl)RY-NH$_2$ (SEQ ID NO:32) or (PEG30,000)-SSA-INle-Pqa-RHYLNWVTRQ(N-methyl)RY-NH$_2$ (SEQ ID NO:36), or a pharmaceutically acceptable salt thereof.

2. A pharmaceutical composition, comprising a therapeutically effective amount of a neuropeptide-2 receptor agonist according to claim 1, or a pharmaceutically acceptable salt thereof, and a pharmaceutically acceptable carrier.

3. A method of treating a metabolic disease or disorder, comprising administering to a patient in need of said treatment a therapeutically effective amount of a neuropeptide-2 receptor agonist according to claim 1 or a pharmaceutically acceptable salt thereof.

* * * * *

SEQUENCE LISTING

```
<160> NUMBER OF SEQ ID NOS: 41

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                                    -continued
        peptide
<220> FEATURE:
<221> NAME/KEY: MOD_RES
<222> LOCATION: (3)
<223> OTHER INFORMATION: Pqa

<400> SEQUENCE: 2

Ile Lys Xaa Arg His Tyr Leu Asn Leu Val Thr Arg Gln Arg Tyr
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 3

Ile Lys Xaa Arg His Tyr Leu Asn Leu Val Thr Arg Gln Arg Tyr
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: m-Tyr

<400> SEQUENCE: 4

Ile Lys Xaa Arg His Tyr Leu Asn Leu Val Thr Arg Gln Arg Tyr
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 3-iodo-Tyr
```

-continued

```
<400> SEQUENCE: 5

Ile Lys Xaa Arg His Tyr Leu Asn Leu Val Thr Arg Gln Arg Tyr
  1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 3,5 di F-Tyr

<400> SEQUENCE: 6

Ile Lys Xaa Arg His Tyr Leu Asn Leu Val Thr Arg Gln Arg Tyr
  1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 2,6 di F-Tyr

<400> SEQUENCE: 7

Ile Lys Xaa Arg His Tyr Leu Asn Leu Val Thr Arg Gln Arg Tyr
  1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 2,6 di Me-Tyr

<400> SEQUENCE: 8
```

Ile Lys Xaa Arg His Tyr Leu Asn Leu Val Thr Arg Gln Arg Tyr
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 4-methoxy-Phe

<400> SEQUENCE: 9

Ile Lys Xaa Arg His Tyr Leu Asn Leu Val Thr Arg Gln Arg Phe
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 10

Ile Lys Xaa Arg His Tyr Leu Asn Leu Val Thr Arg Gln Arg Phe
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 4-amino-Phe

<400> SEQUENCE: 11

Ile Lys Xaa Arg His Tyr Leu Asn Leu Val Thr Arg Gln Arg Phe
1               5                   10                  15

<210> SEQ ID NO 12
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 4 F-Phe

<400> SEQUENCE: 12

Ile Lys Xaa Arg His Tyr Leu Asn Leu Val Thr Arg Gln Arg Phe
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 4(CH2OH)-Phe

<400> SEQUENCE: 13

Ile Lys Xaa Arg His Tyr Leu Asn Leu Val Thr Arg Gln Arg Phe
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 4-trifluoro methyl-Phe

<400> SEQUENCE: 14

Ile Lys Xaa Arg His Tyr Leu Asn Leu Val Thr Arg Gln Arg Phe
 1               5                  10                  15

<210> SEQ ID NO 15
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 3 F-Phe

<400> SEQUENCE: 15

Ile Lys Xaa Arg His Tyr Leu Asn Leu Val Thr Arg Gln Arg Phe
 1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 2,3,4,5,6 Penta F-Phe

<400> SEQUENCE: 16

Ile Lys Xaa Arg His Tyr Leu Asn Leu Val Thr Arg Gln Arg Phe
 1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 3,4 dichloro-Phe

<400> SEQUENCE: 17

Ile Lys Xaa Arg His Tyr Leu Asn Leu Val Thr Arg Gln Arg Phe
 1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

```
                peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: Cha

<400> SEQUENCE: 18

Ile Lys Xaa Arg His Tyr Leu Asn Leu Val Thr Arg Gln Arg Xaa
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 19

Ile Lys Xaa Arg His Tyr Leu Asn Leu Val Thr Arg Gln Arg Trp
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 1-Nal

<400> SEQUENCE: 20

Ile Lys Xaa Arg His Tyr Leu Asn Leu Val Thr Arg Gln Arg Xaa
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
```

```
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 2-Nal

<400> SEQUENCE: 21

Ile Lys Xaa Arg His Tyr Leu Asn Leu Val Thr Arg Gln Arg Xaa
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (15)
<223> OTHER INFORMATION: (C-alpha-methyl)-Tyr

<400> SEQUENCE: 22

Ile Lys Xaa Arg His Tyr Leu Asn Leu Val Thr Arg Gln Arg Tyr
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 23

Ile Lys Xaa Arg His Tyr Leu Asn Trp Val Thr Arg Gln Arg Tyr
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Nle
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 24
```

Ile Xaa Xaa Arg His Tyr Leu Asn Trp Val Thr Arg Gln Arg Tyr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg
<220> FEATURE:
<221> NAME/KEY: MOD_RES
<222> LOCATION: (15)
<223> OTHER INFORMATION: 2,6 difluoro-Tyr

<400> SEQUENCE: 25

Ile Lys Xaa Arg His Tyr Leu Asn Trp Val Thr Arg Gln Arg Tyr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 26

Ile Lys Xaa Arg His Tyr Leu Asn Trp Val Thr Arg Gln Arg Tyr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Pentoyl-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

```
<400> SEQUENCE: 27

Ile Lys Xaa Arg His Tyr Leu Asn Trp Val Thr Arg Gln Arg Tyr
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Trimethylacetyl-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 28

Ile Lys Xaa Arg His Tyr Leu Asn Trp Val Thr Arg Gln Arg Tyr
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cyclohexylacetyl-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 29

Ile Lys Xaa Arg His Tyr Leu Asn Trp Val Thr Arg Gln Arg Tyr
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Benzoyl-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 30
```

Ile Lys Xaa Arg His Tyr Leu Asn Trp Val Thr Arg Gln Arg Tyr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Adamantoyl-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 31

Ile Lys Xaa Arg His Tyr Leu Asn Trp Val Thr Arg Gln Arg Tyr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 32

Ile Lys Xaa Arg His Tyr Leu Asn Trp Val Thr Arg Gln Arg Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(PEG-30,000 SPA)
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 33

Ile Lys Xaa Arg His Tyr Leu Asn Trp Val Thr Arg Gln Arg Tyr
1               5                   10                  15

<210> SEQ ID NO 34
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 34

Ile Lys Xaa Arg His Tyr Leu Asn Trp Val Thr Arg Gln Arg Tyr
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(PEG-40,000 BTC)
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 35

Ile Lys Xaa Arg His Tyr Leu Asn Trp Val Thr Arg Gln Arg Tyr
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Nle
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 36

Ile Xaa Xaa Arg His Tyr Leu Asn Trp Val Thr Arg Gln Arg Tyr
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)
<223> OTHER INFORMATION: Nle
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 37

Ile Xaa Xaa Arg His Tyr Leu Asn Trp Val Thr Arg Gln Arg Tyr
  1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (2)
<223> OTHER INFORMATION: Lys(PEG-30,000 SPA)
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 38

Ile Lys Xaa Arg His Tyr Leu Asn Trp Val Thr Arg Gln Arg Tyr
  1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (2)
<223> OTHER INFORMATION: Lys(PEG-30,000 SSA)
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 39

Ile Lys Xaa Arg His Tyr Leu Asn Trp Val Thr Arg Gln Arg Tyr
  1               5                  10                  15

<210> SEQ ID NO 40
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 40

Ile Lys Xaa Arg His Tyr Leu Asn Trp Val Thr Arg Gln Arg Tyr
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(PEG-30,000 SSA)
<220> FEATURE:
<221> NAME/KEY: MOD_RES
<222> LOCATION: (3)
<223> OTHER INFORMATION: Pqa
<220> FEATURE:
<221> NAME/KEY: MOD_RES
<222> LOCATION: (14)
<223> OTHER INFORMATION: (NMe)Arg

<400> SEQUENCE: 41

Ile Lys Xaa Arg His Tyr Leu Asn Trp Val Thr Arg Gln Arg Tyr
 1               5                  10                  15
```